United States Patent
Ross et al.

(10) Patent No.: US 10,919,877 B2
(45) Date of Patent: Feb. 16, 2021

(54) MULTIFUNCTIONAL INHIBITORS OF MEK/PI3K AND MTOR/MEK/PI3K BIOLOGICAL PATHWAYS AND THERAPEUTIC METHODS USING THE SAME

(71) Applicant: THE REGENTS OF THE UNIVERSITY OF MICHIGAN, Ann Arbor, MI (US)

(72) Inventors: Brian D. Ross, Ann Arbor, MI (US); Marcian Van Dort, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/313,923

(22) PCT Filed: Jul. 6, 2017

(86) PCT No.: PCT/US2017/040866
§ 371 (c)(1),
(2) Date: Dec. 28, 2018

(87) PCT Pub. No.: WO2018/009638
PCT Pub. Date: Jan. 11, 2018

(65) Prior Publication Data
US 2019/0224207 A1   Jul. 25, 2019

Related U.S. Application Data

(60) Provisional application No. 62/454,163, filed on Feb. 3, 2017, provisional application No. 62/359,001, filed on Jul. 6, 2016.

(51) Int. Cl.
 *C07D 401/14* (2006.01)
 *A61P 35/00* (2006.01)
 *A61K 41/00* (2020.01)

(52) U.S. Cl.
 CPC ........ *C07D 401/14* (2013.01); *A61K 41/0057* (2013.01); *A61P 35/00* (2018.01)

(58) Field of Classification Search
 CPC .............................. C07D 401/14; A61P 35/00
 See application file for complete search history.

(56) References Cited

U.S. PATENT DOCUMENTS

| | | | |
|---|---|---|---|
| 7,897,792 B2 | 3/2011 | Iikura et al. |
| 9,284,315 B2 | 3/2016 | Wu et al. |
| 9,611,258 B2 | 4/2017 | Ross et al. |
| 2010/0249099 A1 | 9/2010 | Rewcastle et al. |
| 2011/0009398 A1 | 1/2011 | Sakai et al. |
| 2011/0009405 A1 | 1/2011 | Rewcastle et al. |
| 2011/0053907 A1 | 3/2011 | Rewcastle et al. |
| 2011/0092700 A1 | 4/2011 | Iikura et al. |
| 2011/0166191 A1 | 7/2011 | Zhang et al. |
| 2013/0040912 A1 | 2/2013 | Cmiljanovic et al. |

FOREIGN PATENT DOCUMENTS

| | | |
|---|---|---|
| EP | 0629617 A1 | 12/1994 |
| WO | WO-02/06213 A2 | 1/2002 |
| WO | WO-2004/083167 A1 | 9/2004 |
| WO | WO-2006/122806 A2 | 11/2006 |
| WO | WO-2008/032162 A1 | 3/2008 |
| WO | WO-2009/155121 A2 | 12/2009 |
| WO | WO-2010/003816 A1 | 1/2010 |
| WO | WO-2012/068106 A2 | 5/2012 |

OTHER PUBLICATIONS

STN Registry entry for CAS RN 2578-88-3, Entered STN Nov. 16, 1984, Accessed Nov. 12, 2019.*
Bagrodia et al., Mechanisms of intrinsic and acquired resistance to kinase-targeted therapies, Pigment Cell Melanoma Res., 25(6):819-31 (2012).
Baines et al., Inhibition of Ras for cancer treatment: the search continues, Future Med. Chem., 3(14):1787-808 (Oct. 2011).
Bulinski et al., Overexpression of MAP4 inhibits organelle motility and trafficking in vivo, J. Cell Sci., 110(Pt. 24):3055-64 (1997).
Carracedo et al., Inhibition of mTORC1 leads to MAPK pathway activation through a PI3K-dependent feedback loop in human cancer, J. Clin Invest., 118(9):3065-74 (2008).
Castellano et al., RAS Interaction with PI3K: More Than Just Another Effector Pathway, Genes Cancer, 2(3):261-74 (Mar. 2011).
Cho et al., *Mycobacterium tuberculosis*—induced expression of Leukotactin-1 is mediated by the PI3-K/PDK1/Akt signaling pathway, Mol Cells, 29(1):35-9 (Jan. 2010).
Cole et al., Suppression of pro-metastasis phenotypes expression in malignant pleural mesothelioma by the PI3K inhibitor LY294002 or the MEK inhibitor UO126, Anticancer Res., 26(2A):809-21 (Mar.-Apr. 2006).
Engelman et al., Effective use of PI3K and MEK inhibitors to treat mutant Kras G12D and PIK3CA H1047R murine lung cancers, Nat. Med., 14(12):1351-6 (2008).
Engelman et al., The evolution of phosphatidylinositol 3-kinases as regulators of growth and metabolism, Nat. Rev. Genet., 7(8):606-19 (Aug. 2006).
Falchook et al., Activity of the oral MEK inhibitor trametinib in patients with advanced melanoma: a phase 1 dose-escalation trial, Lancet Oncol., 13(8):782-9 (2012).
Fratti et al., Role of phosphatidylinositol 3-kinase and Rab5 effectors in phagosomal biogenesis and mycobacterial phagosome maturation arrest, J. Cell Biol., 154(3):631-44 (Aug. 2001).

(Continued)

*Primary Examiner* — Alicia L Otton
(74) *Attorney, Agent, or Firm* — Marshall, Gerstein & Borun LLP

(57) ABSTRACT

Multifunctional inhibitors of mTOR, MEK, and PI3K and compositions containing the same are disclosed. Methods of using the multifunctional inhibitors in the treatment of diseases and conditions wherein inhibition of one or more of mTOR, MEK, and PI3K provides a benefit, like cancers, also are disclosed.

8 Claims, 6 Drawing Sheets

(56) References Cited

OTHER PUBLICATIONS

Girotti et al., Inhibiting EGF receptor or SRC family kinase signaling overcomes BRAF inhibitor resistance in melanoma, Cancer Discov., 3(2):158-67 (Feb. 2013).
Hatzivassiliou et al., RAF inhibitors prime wild-type RAF to activate the MAPK pathway and enhance growth, Nature, 464(7287):431-5 (Mar. 2010).
Huang et al., Inhibition of mycobacterial infection by the tumor suppressor PTEN, J. Biol. Chem., 287(27):23196-202 (Jun. 2012).
Infante et al., Safety, pharmacokinetic, pharmacodynamic, and efficacy data for the oral MEK inhibitor trametinib: a phase 1 dose-escalation trial, Lancet Oncol., 13(8):773-81 (2012).
International Application No. PCT/US2017/040866, International Preliminary Report on Patentability, dated Jan. 8, 2019.
International Application No. PCT/US2017/040866, International Search Report and Written Opinion, dated Nov. 20, 2017.
International Application No. PCT/US2017/040866, Invitation to Pay Additional Fees, dated Sep. 26, 2017.
Jemal et al., Cancer statistics, 2010, CA Cancer J. Clin., 60(5):277-300 (Sep.-Oct. 2010).
Karreth et al., C-Raf inhibits MAPK activation and transformation by B-Raf(V600E), Mol. Cell, 36(3):477-86 (Nov. 2009).
Kim et al., Phase II study of the MEK1/MEK2 inhibitor Trametinib in patients with metastatic BRAF-mutant cutaneous melanoma previously treated with or without a BRAF inhibitor, J. Clin. Oncol., 31(4):482-9 (2013).
Kuijl et al., Intracellular bacterial growth is controlled by a kinase network around PKB/AKT1, Nature, 450(7170):725-30 (Nov. 2007).
Liau et al., HMGA1 is a determinant of cellular invasiveness and in vivo metastatic potential in pancreatic adenocarcinoma, Cancer Res., 66(24):11613-22 (Dec. 2006).
Liu et al., The rLrp of *Mycobacterium tuberculosis* inhibits proinflammatory cytokine production and downregulates APC function in mouse macrophages via a TLR2-mediated PI3K/Akt pathway activation-dependent mechanism, Cell Mol. Immunol.,13(6):729-46 (Nov. 2016).
Liu et al., Targeting the phosphoinositide 3-kinase pathway in cancer, Nat. Rev. Drug Discov., 8(8):627-44 (Aug. 2009).
Lorusso et al., Phase I and pharmacodynamic study of the oral MEK inhibitor CI-1040 in patients with advanced malignancies, J. Clin. Oncol., 23(23):5281-93 (2005).
Ma et al., Asymmetric dipolar cycloaddition reactions: a practical, convergent synthesis of chiral pyrrolidines, Tetrahedron: Asymmetry, 8(6):883-7 (1997).
Matsuoka et al., Tamoxifen inhibits tumor cell invasion and metastasis in mouse melanoma through suppression of PKC/MEK/ERK and PKC/PI3K/Akt pathways, Exp. Cell Res., 315(12):2022-32 (Jul. 2009).
McCubrey et al., Emerging Raf inhibitors, Expert. Opin. Emerg. Drugs, 14(4):633-48 (Dec. 2009).
Mirzoeva et al., Basal subtype and MAPK/ERK kinase (MEK)—phosphoinositide 3-kinase feedback signaling determine susceptibility of breast cancer cells to MEK inhibition, Cancer Res., 69(2):56572 (2009).
Montagut et al., Targeting the RAF-MEK-ERK pathway in cancer therapy, Cancer Lett., 283(2):125-34 (2009).
Muhlradt et al., Epothilone B stabilizes microtubuli of macrophages like taxol without showing taxol-like endotoxin activity, Cancer Res., 57(16):3344-6 (1997).
Nicolaou et al., Synthesis of epothilones A and B in solid and solution phase, Nature, 387(6630):268-72 (1997).
Nishimura et al., Phospshoinositide 3-kinase (PI3K)/mammalian target of rapamycin (mTOR) dual inhibitors: discovery and structure-activity relationships of a series of quinoline and quinoxaline derivatives, J. Med. Chem., 54(13):4735-51 (Jul. 2011).
Panda et al., Differential effects of vinblastine on polymerization and dynamics at opposite microtubule ends, J. Biol. Chem., 271(47):29807-12 (1996).
Panda et al., Stabilization of microtubule dynamics by estramustine by binding to a novel site in tubulin: a possible mechanistic basis for its antitumor action, Proc. Natl. Acad. Sci. USA, 94(20):10560-4 (1997).
Pasquale, Eph receptors and ephrins in cancer: bidirectional signalling and beyond, Nat. Rev. Cancer, 10(3):165-80 (Mar. 2010).
Poulikakos et al., RAF inhibitors transactivate RAF dimers and ERK signalling in cells with wild-type BRAF, Nature, 464(7287):427-30 (Mar. 2010).
Rand et al., Matrix metalloproteinase-1 is regulated in tuberculosis by a p38 MAPK-dependent, p-aminosalicylic acid-sensitive signaling cascade, J. Immunol., 182(9):5865-72 (May 2009).
Sawyers, Imatinib GIST keeps finding new indications: successful treatment of dermatofibrosarcoma protuberans by targeted inhibition of the platelet-derived growth factor receptor, J. Clin. Oncol., 20(17):3568-9 (2002).
Sebolt-Leopold et al., Targeting the mitogen-activated protein kinase cascade to treat cancer, Nat. Rev. Cancer, 4(12):937-47 (Dec. 2004).
Sebolt-Leopold, Advances in the development of cancer therapeutics directed against the RAS-mitogen-activated protein kinase pathway, Clin. Cancer Res., 14(12):3651-6 (Jun. 2008).
Shao et al., BH3-only protein silencing contributes to acquired resistance to PLX4720 in human melanoma, Cell Death Differ., 19(12):2029-39 (Dec. 2012).
Shimizu et al., The clinical effect of the dual-targeting strategy involving PI3K/Akt/mTOR and RAS/MEK/ERK pathways in patients with advanced cancer, Clin. Cancer Res., 18(8):2316-25 (2012).
Singh et al., Regulation of matrix metalloproteinase-1, -3, and -9 in *Mycobacterium tuberculosis*—dependent respiratory networks by the rapamycin-sensitive PI3K/p70(S6K) cascade, FASEB J., 28(1):85-93 (Jan. 2014).
Smalley et al., Inhibition of BRAF and BRAF+MEK drives a metastatic switch in melanoma, Mol. Cell Oncol., 2(4):e1008291 (Mar. 2015).
Sos et al., Identifying genotype-dependent efficacy of single and combined PI3K- and MAPK-pathway inhibition in cancer, Proc. Natl. Acad. Sci. USA, 106(43):18351-6 (2009).
Van Dort et al., Discovery of Bifunctional Oncogenic Target Inhibitors against Allosteric Mitogen-Activated Protein Kinase (MEK1) and Phosphatidylinositol 3-Kinase (PI3K), J. Med. Chem., 59(6):2512-22 (Mar. 2016).
Vasquez et al., Nanomolar concentrations of nocodazole alter microtubule dynamic instability in vivo and in vitro, Mol. Biol. Cell, 8(6):973-85 (1997).
Venkatesan et al., Bis(morpholino-1,3,5-triazine) derivatives: potent adenosine 5'-triphosphate competitive phosphatidylinositol-3-kinase/mammalian target of rapamycin inhibitors: discovery of compound 26 (PKI-587), a highly efficacious dual inhibitor, J. Med. Chem., 53(6):2636-45 (Mar. 2010).
Wee et al., PI3K pathway activation mediates resistance to MEK inhibitors in KRAS mutant cancers, Cancer Res., 69(10):4286-93 (2009).
Yu et al., Response and determinants of cancer cell susceptibility to PI3K inhibitors: combined targeting of PI3K and Mek1 as an effective anticancer strategy, Cancer Biol. Ther., 7(2):307-15 (2008).
Al-Lazikani, B., et al., Combinatorial Drug Therapy for Cancer in the Post-Genomic Era, *Nature Biotechnology*, 2012, vol. 30, No. 7, pp. 679-692.
Apsel, Beth, et al., "Targeted Polypharmacology: Discovery of Dual Inhibitors of Tyrosine and Phosphoinositide Kinases," *Nature Chemical Biology*, 2008, vol. 4, No. 11, pp. 691-699.
Atefi, M., et al., "Reversing Melanoma Cross-Resistance to BRAF and MEK Inhibitors by Co-Targeting the AKT/mTOR Pathway," *PLoS one*, 2011, vol. 6, No. 12, p. e28973.
Cancer [online], [retrieved on Jul. 6, 2007]. Retrieved from the internet, URL http://www.nlm.nih.gov/medlineplus/cancer.html.
Cancer [online], [retrieved on Jul. 6, 2007]. Retrieved from the internet, URL; http://en.wikipedia.org/wiki/Cancer.
Golub et al., Molecular Classification of Cancer: Class Discovery and Class Prediction by Gene Expression monitoring, *Science*, 286:531-6 (1999).
Kaiser, J., "Combining Targeted Drugs to Stop Resistant Tumors," *Science*, 2011, vol. 331, No. 6024, pp. 1542-1545.

(56) References Cited

OTHER PUBLICATIONS

Lala et al., Role of nitric oxide in tumor progression: lessons from experimental tumors, *Cancer Metastasis Rev.*, 17:91-106 (1998).
Park, H., "Discovery of MEK/PI3K Dual Inhibitor Via Structure-Based Virtual Screening," *Bioorganic & Medicinal Chemistry Letters*, 2012, vol. 22, No. 15, pp. 4946-4950.
Rewcastle, G. W., et al., "Synthesis and Biological Evaluation of Novel Analogues of the Pan Class I Phosphatidylinositol 3-Kinase (PI3K) Inhibitor 2-(Difluoromethyl)-1-[4,6-di(4-Morpholinyl)-1,3,5-Triazin-2-yl]-1H-Benzimidazole (ZSTK474)," *Journal of Medicinal Chemistry*, 2011, vol. 54, No. 20, pp. 7105-7126.
Roberts, P. J., "Combined PI3K/mTOR and MEK Inhibition Provides Broad Antitumor Activity in Faithful Murine Cancer Models," *Clinical Cancer Research*, 2012, vol. 18, No. 19, pp. 5290-5303.
International Search Report in International Patent Application No. PCT/US2014/023860, dated Jul. 7, 2014.
Supplementary European Search Report, European patent application No. EP14779150, dated Jul. 20, 2016.
European Patent Application No. 17740578, Office Action, dated Jul. 23, 2020.

\* cited by examiner

MULTIFUNCTIONAL INHIBITORS OF MEK/PI3K AND MTOR/MEK/PI3K BIOLOGICAL PATHWAYS AND THERAPEUTIC METHODS USING THE SAME

CROSS REFERENCE TO RELATED APPLICATIONS

This is a U.S. national phase of International Application No. PCT/US2017/040866, filed Jul. 6, 2017, which claims the benefit of U.S. Provisional Patent Application No. 62/454,163, filed Feb. 3, 2017 and U.S. Provisional Patent Application No. 62/359,001, filed Jul. 6, 2016.

STATEMENT OF GOVERNMENTAL INTEREST

This invention was made with government support under grants CA085878 and CA197701 awarded by the U.S. National Institutes of Health. The government has certain rights in the invention

FIELD OF THE INVENTION

The present invention relates to multifunctional inhibitors, including bifunctional inhibitors, trifunctional inhibitors, and tetrafunctional inhibitors of mTOR, MEK, and PI3K, and to therapeutic methods of treating conditions and diseases wherein inhibition of one or more of mTOR, MEK, and PI3K provides a benefit. The present multifunctional inhibitors are useful as agents for cancer therapy, either alone or in combination with radiation and/or chemotherapeutics.

BACKGROUND OF THE INVENTION

Aberrant hyperactivation of KRAS plays a prominent role in tumor initiation and progression in a broad spectrum of human cancers. KRAS mutations comprise 86% of all RAS mutations and are associated with the highest frequency, roughly 22%, of all human malignancies (1). The incidence of KRAS mutations is especially high in pancreatic and colorectal malignancies, where it occurs at a frequency of greater than 90% and greater than 40%, respectively. Pancreatic and colorectal cancers are among the most lethal of all cancers and are the fourth and third leading cause of cancer deaths in the United States (2). Approximately 80% of all pancreatic cancer cases present with locally advanced or metastatic disease, which precludes surgical intervention. Currently, there are no curative options for the treatment of KRAS-activated cancers. Treatment options for KRAS mutant patients with metastatic colorectal cancer who have failed first-line chemotherapy with a fluoropyrimidine and oxaliplatin are also limited.

Tumor cell invasion, motility, and metastasis is a significant cause of cancer patient mortality. The process of tumor metastasis results due to a complex series of processes (36). Studies have reported that the PI3K/Akt pathway is significantly involved in tumor progression and metastasis (37). Moreover, MEK as well as PI3K inhibitors have been reported to be effective in downregulating pro-metastasis phenotypes in tumor cells (38). Inhibitors mediating the blockade of MAPK kinase (MEK), which is downstream of BRAF in the MAPK pathway and has been associated with improved progression-free and overall survival in BRAF V600 melanoma patients (comprising both V600E and V600K mutations) (39, 40). Taken together inhibition of the mitogen activated protein kinase (Ras/Raf/MEK/ERK) and phosphoinositide 3-kinase/protein kinase B (PI3K/AKT) pathways has been established with reduced motile and invasive (metastatic) capabilities (41, 42). Thus molecularly targeted agents directed against Ras/Raf/MEK/ERK and PI3K/Akt signaling pathways are important for the inhibition of growth and metastasis of tumor cells. Inhibition of tumor cell migration, invasion, and metastasis through dual suppression of the Ras/Raf/MEK/ERK and PI3K/Akt pathways is anticipated to play a key role in improving cancer therapy regimens. Compounds which simultaneously target Ras/Raf/MEK/ERK and PI3K/Akt pathways should provide for improved inhibition of invasive phenotypes and prometastatic processes for treatment of primary and metastatic disease leading to decreased patient mortality.

Efforts to develop drugs that directly target mutant KRAS remain challenging because specificity issues are problematic. Consequently, efforts at pharmacologic intervention of KRAS signaling have focused intensively in recent years on downstream targets in the two central RAS effector pathways, RAF/MEK/ERK and PI3K/AKT/mTOR (3, 4). RAF and MEK have spawned a number of drug discovery programs that have resulted in attractive clinical candidates (5-7). Clinical activity of BRAF inhibitors likely will be restricted to patients with BRAF mutated tumors because the absence of a BRAF mutation is associated with induction, rather than inhibition, of MAPK signaling in response to this targeted approach (8-10). In contrast, MEK inhibitors have been shown to exert antiproliferative effects in roughly half of the KRAS mutant tumors tested (11). It is encouraging that the MEK inhibitor CI-1040, as well as trametinib, have both elicited objective responses in Phase 1 testing (12, 13). MEK inhibition therefore is a viable approach for the treatment of KRAS activated cancers, but in a monotherapy setting, MEK inhibition is unlikely to produce the degree of activity needed to significantly impact outcome in this refractory patient population.

One strategy to improve MEK inhibitor single agent activity is the additional targeting of PI3K signaling. This combination strategy is based on in vitro and in vivo evidence suggesting that KRAS mutant tumors require dual inhibition of both the MAPK and PI3K pathways to achieve maximal inhibition of tumor growth (11, 14-16). Release of negative feedback loops has been shown to lead to activation of the alternate pathway when either one is inhibited (16, 17). Activation of the PI3K pathway, commonly due to PI3KCA mutations or PTEN loss, represents a major resistance mechanism to MEK inhibitor therapy in KRAS mutant cancers. Combined inhibition of both pathways leads to a significant increase in apoptosis and tumor shrinkage (18).

Because the RAS/RAF/MEK/ERK signal transduction pathway is activated in a significant percentage of the most aggressive and deadly forms of human cancers, several small molecule inhibitors targeting this pathway have either been FDA approved or are in active clinical development. Unfortunately, despite the clinical efficacy of a commercially-available BRAF inhibitor, i.e., PLX4032 or Vemurafenib, in treating tumors bearing both BRAF and KRAS activating mutations, the drug is ineffective against tumors with native BRAF due to paradoxical induction of ERK signaling.

mTOR, MEK, and PI3K inhibitors therefore are known in the art. For example, Iikura et al. U.S. Pat. No. 7,897,792 discloses a class of coumarin-based MEK inhibitors. PI3K inhibitors are disclosed, for example, in U.S. Patent Nos. 2010/0249099; 2011/0009405; and 2011/0053907. The combined use of PI3K and MEK inhibitors to treat lung cancer is disclosed, for example, in Engelman et al., *Nature Medicine*, Vol. 14, Number 14, pages 1351-56 (2008).

mTOR inhibitors also are known in the art, for example in WO 2006/122806, WO 2010/003816, U.S. Pat. No. 9,284,315, and WO 2012/068106. In some embodiments, a prior art inhibitor is a dual mTOR and PI3K inhibitor.

Modulation of distal components of the PI3K path also has been implicated in a wide variety of other disease processes including infections and immune/inflammatory diseases characterized by tissue destruction (27). For example, *Mycobacterium tuberculosis* (Mtb) is a major world-wide health problem. Intracellular signaling cascades including for example the p38 and ERK mitogen-activated protein kinases are known to be important in matrix metalloproteinase (MMP) regulation (28). Phosphatidyl inositol 3-kinase (PI3K) is increasingly recognized as a key signaling cascade that is implicated in the regulation of diverse inflammatory responses (29, 30, 31). PI3K signaling is vital for TNF-α and IL-10 secretion from monocytes while Mtb-induced chemokine up-regulation can be inhibited by PI3K inhibitors (32). PIP3, the downstream product of PI3K activity, is also required for mycobacterial phagosome maturation (33). AKT inhibition can produce a global suppressive effect on secretion and gene expression of MMPs and intracellular growth of Mtb is prevented by the inhibition of AKT (34), and pharmacological inhibition of AKT has been found to reduce mycobacterial infection levels (35). Compounds targeting the signaling pathways related to these signaling processes may be efficacious for interruption of signal transduction mechanisms in mycobacterial infection along with providing for a reduction in inflammatory tissue damage.

The cellular signaling pathway mTOR is a component of the phosphatidylinositol 3-kinase (PI3K) cell survival pathway that plays a significant role in regulation of cell growth and proliferation. Aberrant PI3K pathway activation is considered to be involved in many types of cancer leading to associated resistance to therapy. The PI3K/AKT/mTOR pathway is involved in the regulation of metabolism, cell growth and survival, cell-cycle progression, and transcription and translation. AKT resides downstream of phosphoinositide 3-kinase (PI3K) signaling, which is activated upon binding of ligands (such as insulin or other growth factors) to receptor tyrosine kinases (RTKs) on the cell surface. Activated AKT phosphorylates a range of substrates, including PRAS40, BAD, and FOXO3. The cell signaling pathway mTOR acts upstream and downstream of Akt and thus serves as a critical signaling junction in the PI3K pathway. The kinase mTOR assembles into two distinct complexes inside the cell (mTORC1 and mTORC2), and are located on both sides of the AKT signaling hub. The rapamycin-sensitive complex with raptor (mTORC1) resides downstream of AKT while the rapamycin-insensitive complex with rictor (mTORC2) can fully activate AKT by direct phosphorylation at Ser473. Thus, it is well established that mTOR is able to form two primary multiprotein complexes known as mTORC1 and mTORC2. These complexes serve to regulate cellular protein syntheses, which are key requirements for cellular homeostasis including growth and proliferation. mTOR therefore is a very relevant cancer signaling pathway downstream from surface receptors, and a significant need exists for improved drugs capable of targeting mTOR.

Ligand-bound activation of a transmembrane receptor leads to the activation of PI3K which subsequently phosphorylates Akt, which is dephosphorylated by PTEN. Due to enhanced downstream signaling of the PI3K/Akt/mTOR pathway cancer along with autoimmune diseases including inflammatory processes are in part responsible for these diseases and exert numerous downstream biological effects, including the translation of mRNA by phosphorylating downstream targets, such as 4E-BP1 and p70 S6 kinase, the suppression of autophagy through Atg13 and ULK1, ribosome biogenesis, and activation of transcription that leads to increased mitochondrial activity or adipogenesis. Therefore, mTOR is a downstream target of EGFR/PI3K/Akt and MET signaling along with significant cross talk with MEK signaling, and accordingly is considered a key target for the therapeutic treatment of various types of diseases.

Dysregulation of the PI3K/AKT/mTOR and MEK pathways leads to unchecked cellular growth and proliferation. However, a need still exists in the art for compounds and methods to treat cancers and other diseases and conditions by inhibition of mTOR, MEK, and PI3K. Despite the discovery of small molecular inhibitors of mTOR, MEK, and PI3K, the design of potent, inhibitors of mTOR, MEK, and PI3K remains a significant challenge in modern drug discovery. Accordingly, a need still exists in the art for multifunctional mTOR, MEK, and PI3K inhibitors having physical and pharmacological properties that permit use of the multifunctional inhibitors in therapeutic applications. The present invention provides single-agent multifunctional compounds designed to bind to mTOR, MEK, and PI3K, and to inhibit mTOR, MEK, and PI3K activity.

SUMMARY OF THE INVENTION

The present invention is directed to a single compound that co-targets the MAP kinase and PI3K pathways, and to methods of treating a cancer by administering such a compound to an individual in need thereof. The present compounds have been developed to co-target these important signaling pathways in order to combat diseases associated with their pathway dysregulation.

More particularly, the present invention is directed to novel multifunctional compounds that are capable of inhibiting two or three key signal transduction pathways (i.e., mTOR, MEK, and PI3K) implicated in tumor growth, progression, and metastasis. Individual mTOR, PI3K, and MEK inhibitors, chemically modified to accommodate linkers, while maintaining high binding affinity towards their respective enzyme targets, have been conjugated to provide the present bifunctional, trifunctional, and tetrafunctional mTOR/MEK/PI3K inhibitors. The present compounds inhibit KRAS-driven tumor progression by simultaneously targeting two or three critical regulatory nodes, mTOR, MEK, and PI3K, and in so doing intercept the cross-talk that occurs between their respective pathways.

The present invention therefore is directed to multifunctional inhibitors of mTOR, MEK, and PI3K enzymes, to compositions comprising the inhibitors, and to methods of using the inhibitors in a therapeutic treatment of conditions and diseases wherein inhibition of mTOR, MEK, and PI3K activity provides a benefit. The present compounds are potent inhibitors of mTOR activation, MEK activation, and PI3K activation, and are useful in the treatment of cancers, and particularly KRAS mutant tumors.

The present invention is directed to multifunctional compounds capable of inhibiting MEK and PI3K activity having the following structural formulas:

(a)
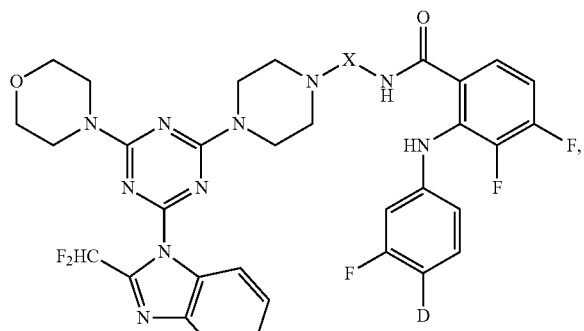

D is I, —C≡CH, or —C≡C—R, R is alkyl or aryl, and X is selected from the group consisting of

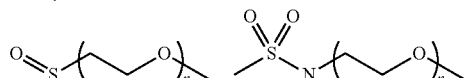
n is 1, 2, 3, 4, or 5

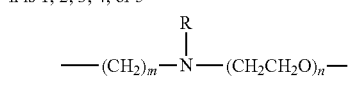
R = H, alkyl, or aryl
m, n independently are 1, 2, 3, 4, or 5

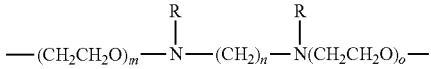
R independently is H, alkyl, or aryl
m, n, o independently are 1, 2, 3, 4, or 5

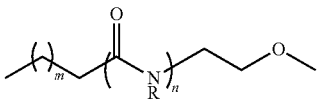
R is H, alkyl, or aryl
where m is 0, 1, 2, 3, 4, or 5
and n is 1, 2, 3, 4, or 5
or any combination of m and n

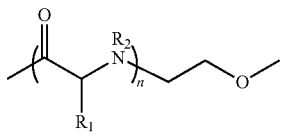
$R_1$, $R_2$ independently are, H, alkyl, or aryl
n is 1, 2, 3, 4, or 5

-continued

D is I, —C≡CH, or —C≡C—R where R is alkyl or aryl $R_3$ is H, alkyl, aryl —$(CH_2)_p$—OH, or —$(CH_2)_p$—$NR_4$ where p = 1-6 and $R_4$ = H, alky, aryl and X is selected from the group consisting of

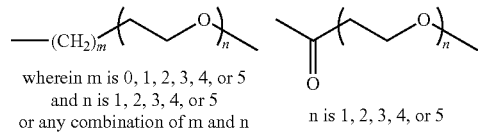
wherein m is 0, 1, 2, 3, 4, or 5
and n is 1, 2, 3, 4, or 5
or any combination of m and n
n is 1, 2, 3, 4, or 5

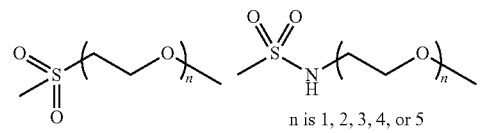
n is 1, 2, 3, 4, or 5

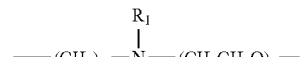
n is 1, 2, 3, 4, or 5

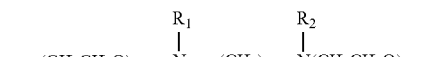
$R_1$ = H, alkyl, or aryl
m, n independently are 1, 2, 3, 4, or 5

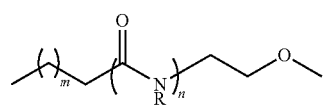
$R_1$ = H, alkyl, or aryl
m, n, o independently are 1, 2, or 3,

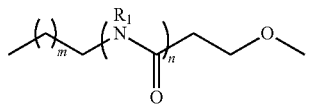
$R_1$ = H, alkyl, or aryl
m is 0, 1, 2, 3, 4, or 5, and n is 1, 2, 3, 4, or 5
or any combination of m and n

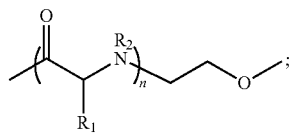
$R_1$ = H, alkyl, or aryl
m is 0, 1, 2, 3, 4, or 5, and n is 1, 2, 3, 4, or 5
or any combination of m and n

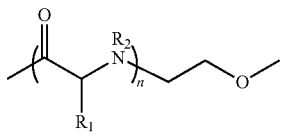
$R_1$, $R_2$ independently are, H, alkyl, or aryl
n is 1, 2, 3, 4, or 5

(b)
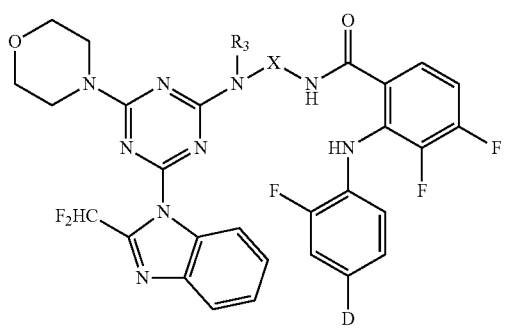

(c)
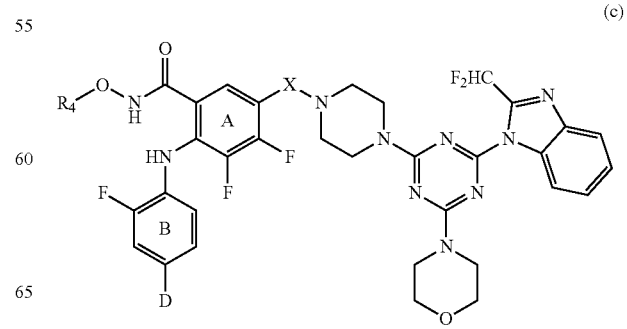

7

-continued

[Structure showing compound with R4-O-NH-C(=O) group attached to ring A with F substituents, connected through X to piperazine-triazine-benzimidazole-morpholine system, with ring B having D and F substituents]

where R$_4$ = R-(-)—CH$_2$CHOH(CH$_2$OH); —CH$_2$CH$_2$OH; or —CH$_2$CH$_2$—NH$_2$;

D is I, —C≡CH, or —C≡C—R, R is alkyl or aryl, and X is selected from the group consisting of —(O⁀⁀⁀)$_n$—     —(O⁀⁀⁀)$_n$—C(=O)— n is 1, 2, 3, 4, or 5 n is 1, 2, 3, 4, or 5

R$_1$
—O(CH$_2$)$_m$—N—(CH$_2$)$_n$—

R$_1$ is H, alkyl, or aryl
m and n independently are 1, 2, 3, 4, or 5

R$_1$         R$_1$
—(CH$_2$CH$_2$O)m—N—(CH$_2$)n—N(CH$_2$)o—;

R$_1$ independently is H, alkyl, or aryl
m, n, and o independently are 1, 2, 3, 4, or 5

(d)

[Structure showing bis-morpholine-triazine-benzimidazole(CHF$_2$) system connected via CH to X-NH-C(=O)-benzene ring with F,F,NH-phenyl-D substituents]

D is I, —C≡CH, or —C≡C—R, R is alkyl or aryl, and X is selected from the group consisting of —(CH$_2$)$_m$—(O⁀⁀⁀)$_n$—     —C(=O)—(O⁀⁀⁀)$_n$— wherein m is 0, 1, 2, 3, 4, or 5
and n is 1, 2, 3, 4, or 5
or any combination of m and n n is 1, 2, 3, 4, or 5

CH$_3$-S(=O)$_2$-(O⁀⁀⁀)$_n$—     CH$_3$-S(=O)$_2$-NH-(O⁀⁀⁀)$_n$— n is 1, 2, 3, 4, or 5

R
—(CH$_2$)$_m$—N—(CH$_2$CH$_2$O)$_n$—

R = H, alkyl, or aryl
m, n independently are 1, 2, 3, 4, or 5

8

-continued

R$_1$         R$_1$
—(CH$_2$CH$_2$O)$_m$—N—(CH$_2$)$_n$—N(CH$_2$CH$_2$O)$_o$—

R$_1$ independently is H, alkyl, or aryl
m, n, o independently are 1, 2, 3, 4, or 5

[Structure: alkyl chain with C(=O)-N(R$_1$)-(CH$_2$)$_n$-O-CH$_3$]

R$_1$ is H, alkyl, or aryl
where m is 0, 1, 2, 3, 4, or 5
and n is 1, 2, 3, 4, or 5

[Structure: C(=O)-CH(R$_1$)-N(R$_2$)-(CH$_2$)$_n$-O—];

R$_1$, R$_2$ independently are, H, alkyl, or aryl
n is 1, 2, 3, 4, or 5

(e)

[Structure showing morpholine-triazine(benzimidazole-CHF$_2$)-X-N(R$_5$)-W-N(R$_6$)-Z-S(=O)$_2$-NH-phenyl(F,F)-NH-phenyl(Y,D)]

Y is F, Cl
D is I or —C≡CR, where R = H, alkyl or aryl
R$_5$, R$_6$, independently, are H, alkyl, aryl, or taken together to from a 5- or 6- membered ring;
X, W, and Z, independently, are carbonyl or (CR$_1$R$_2$)$_n$
where R$_5$, R$_6$, independently, are H, alkyl, or aryl, and n = 0, 1, 2, 3, 4, or 5;
x is R
—(CH$_2$)$_m$—N—(CH$_2$)$_n$—

R = H, alkyl, or aryl
where m, n, independently, are 1, 2, 3, 4, or 5

R
—(CH$_2$CH$_2$O)$_m$—N—(CH$_2$)$_n$—; and

R = H, alkyl, or aryl
where m, n, independently, are 1, 2, 3, 4, or 5

(f)

[Structure showing morpholine-triazine-piperazine-X-NH-C(=O)-benzene(F,F)-NH-phenyl(F,D), with triazine also bearing benzimidazole-CHF$_2$]

wherein D is I, —C≡CH, or —C≡C—R, R is alkyl or aryl, and X is selected from the group consisting of:

-continued

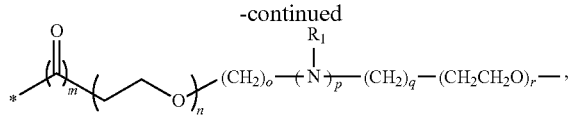

$R_1$, independently, is H, alkyl, or aryl, wherein, independently,
m = 0, 1; n = 0-6; o = 0-6; p = 0, 1; q = 0-6; r = 2-6

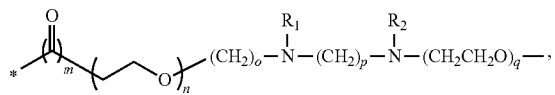

wherein, independently, m = 0, 1; n = 0-6; o = 0-6; p = 1-6;
q = 2-6, and $R_1$, $R_2$, independently, are H, alkyl, or aryl

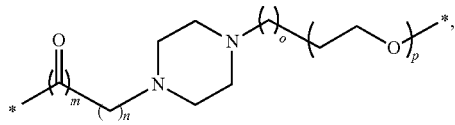

wherein, independently, m = 0, 1; n = 0-6; o = 0-6;
p = 2-6

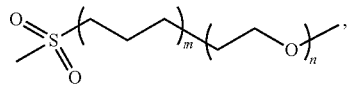

wherein, independently,
m = 0-6; n = 2-6

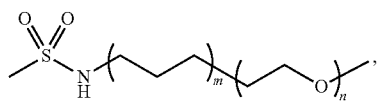

wherein independently, m = 0-6; n = 2-6

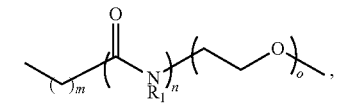

$R_1$, independently, is H, alkyl, or aryl, wherein,
independently, m = 0-6; n = 1-6; o = 2-6

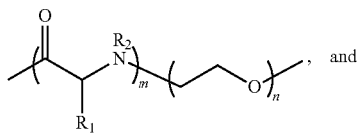
and $R_1$, $R_2$, independently, are H, alkyl, or aryl,
wherein, independently, m = 1-6; n = 2-6; o = 2-6

wherein, independently, m = 0, 1; n = 1-6; o = 2-6 or a pharmaceutically acceptable salt thereof.

In another embodiment, the present invention is directed to trifunctional compounds capable of inhibiting mTOR, MEK, and PI3K activity having a following structural formulas:

(a)

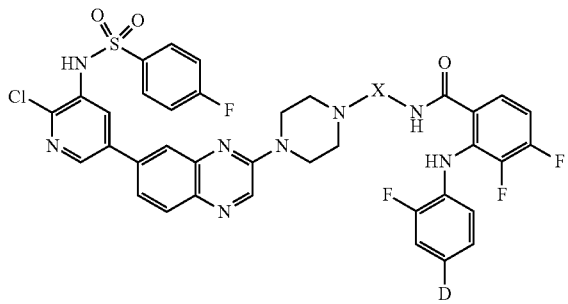

wherein D is I, —C≡CH, or —C≡C—R, R = alkyl or aryl, and X is selected from the group consisting of:

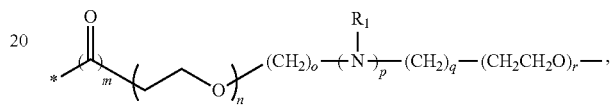

$R_1$, independently, is H, alkyl, or aryl, wherein, independently,
m = 0, 1; n = 0-6; o = 0-6; p = 0, 1; q = 0-6; r = 2-6

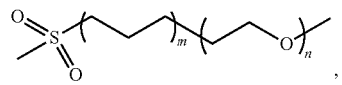

wherein, independently, m = 0-6; n = 2-6

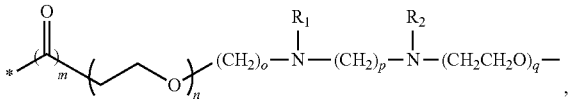

wherein, independently, m = 0, 1; n = 0-6; o = 0-6;
p = 1-6; q = 2-6 and $R_1$, $R_2$, independently, are H, alkyl, or aryl

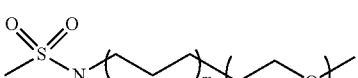

wherein independently, m = 0-6; n = 2-6

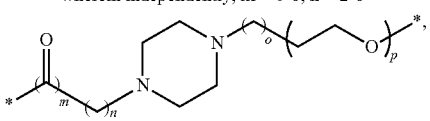

wherein, independently, m = 0, 1; n = 0-6; o = 0-6;
p = 2-6

$R_1$, independently, is H, alkyl, or aryl, wherein,
independently, m = 0-6; n = 1-6
o = 2-6

-continued

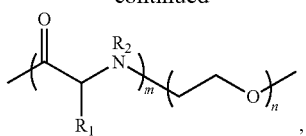

R₁, R₂, independently, are H, alkyl, or aryl
wherein, independently, m = 1-6; n = 2-6

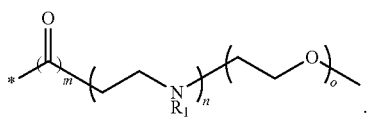

R₁, independently, is H, alkyl, or aryl,
wherein, independently, m = 0, 1; n = 1-6; o = 2-6

(b)

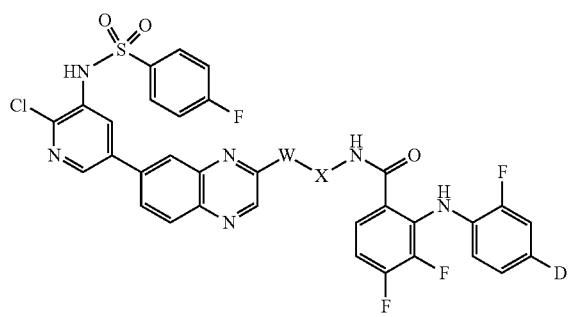

where W is (  ) or 

and R is H, alkyl or aryl and m = 0, 1-6;
D = I, —C≡CH, —C≡C—R
where R = alkyl or aryl, wherein X is selected from the group
consisting of:

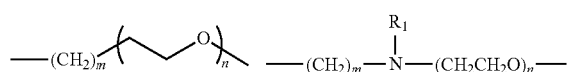

where m = 0, 1-6; n = 1-6;
or any combination of m and n

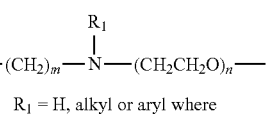

R₁ = H, alkyl or aryl where
m, n independently are 1-6

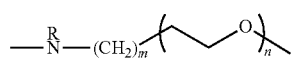

where R is H, alkyl, or aryl and m = 0, 1-6;
n = 1-6; or any combination of m and n

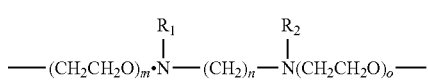

R₁, R₂ are independently H, alkyl or aryl
and m, n, o independently are 1-6

(c)

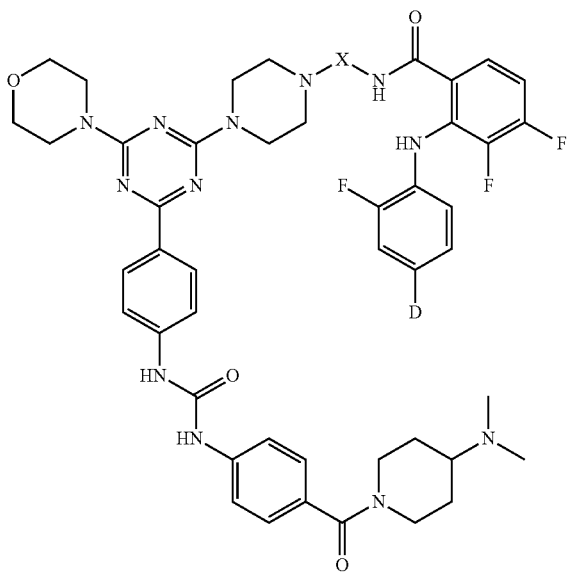

wherein D is I, —C≡CH, or —C≡C—R,
R = alkyl or aryl, and X is selected from the group
consisting of:

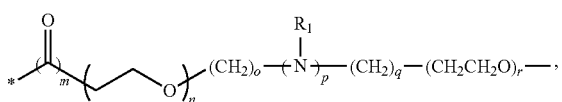

R₁, independently, is H, alkyl, or aryl, wherein, independently,
m = 0, 1; n = 0-6; o = 1-6; p = 0, 1; q = 0-6; r = 2-6

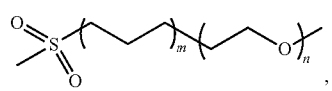

wherein, independently,
m = 0-6; n = 2-6

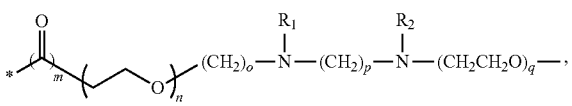

wherein, independently, m = 0, 1; n = 0-6; o = 1-6; p = 1-6;
q = 2-6 and R₁, R₂, independently, are H, arkyl, or aryl

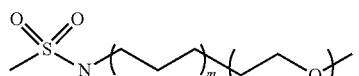

wherein independently,
m = 0-6; n = 2-6

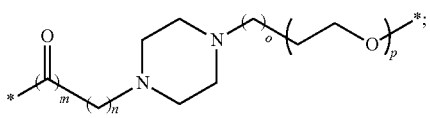

wherein, independently, m = 0, 1; n = 0-6; o = 0-6;
p = 2-6

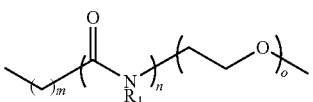

R₁, independently, is H, alkyl, or aryl, wherein,
independently, m = 0-6; n = 1-6; o = 2-6

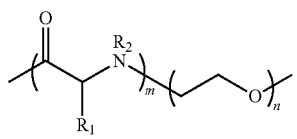

R₁, R₂, independently, are H, alkyl, or aryl,
wherein, independently, m = 1-6; n = 2-6

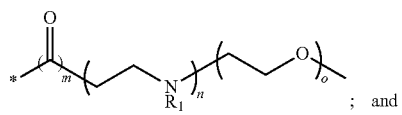
; and wherein, independently, m = 0, 1; n = 1-6; o = 2-6

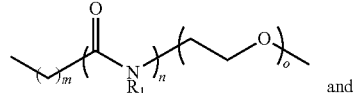
and

R₁, independently, is H, alkyl, or aryl, wherein
independently m = 1-6; n = 1-6; o - 2-6

;

R₁, independently, is H, alkyl, or aryl,
wherein independently m = 1-6; n = 2-6 or a pharmaceutically acceptable salt thereof.

In one embodiment, the present invention provides a method of treating a condition or disease by administering a therapeutically effective amount of a present multifunctional compound to an individual in need thereof. The disease or condition of interest is treatable by inhibition of mTOR and/or MEK and/or PI3K, for example, a cancer.

Another embodiment of the present invention is to provide a composition comprising (a) a present multifunctional inhibitor and (b) an excipient and/or pharmaceutically acceptable carrier useful in treating diseases or conditions wherein inhibition of one or more of mTOR, MEK, and PI3K provides a benefit.

Another embodiment of the present invention is to utilize a composition comprising a present multifunctional compound and a second therapeutically active agent in a method of treating an individual for a disease or condition wherein inhibition of at least one of mTOR, MEK, and PI3K provides a benefit.

In a further embodiment, the invention provides for use of a composition comprising a present multifunctional inhibitor and an optional second therapeutic agent for the manufacture of a medicament for treating a disease or condition of interest, e.g., a cancer.

Still another embodiment of the present invention is to provide a kit for human pharmaceutical use comprising (a) a container, (b1) a packaged composition comprising a present multifunctional inhibitor, and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

These and other embodiments and features of the present invention will become apparent from the following detailed description of the preferred embodiments.

(d)

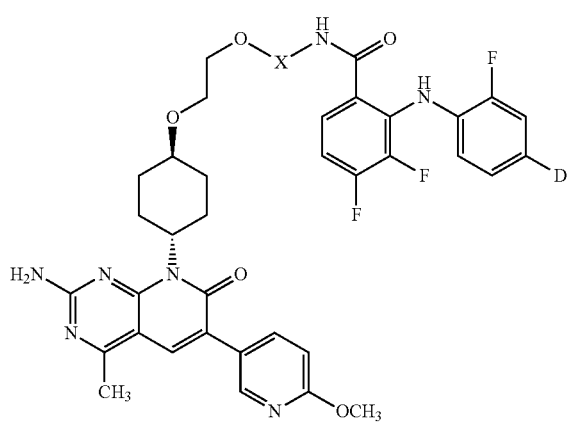

wherein D is I, —C≡CH, or —C≡C—R,
R = alkyl or aryl, and X is selected from the group
consisting of:

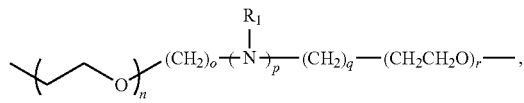

R₁, independently, is H, alkyl, or aryl wherein, independently,
n = 0-6; o = 1-6; p = 0, 1; q = 0-6; r = 2-6

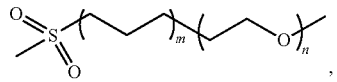

wherein, independently, m = 0-6; n = 2-6

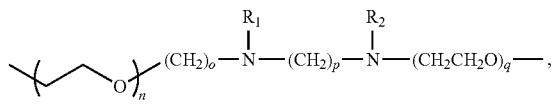

wherein, independently, n = 0-6; o = 1-6; p = 1-6;
q = 2-6; and R₁, R₂, independently, is H, alkyl, or aryl

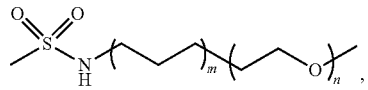

wherein, independently, m = 0-6; n = 2-6

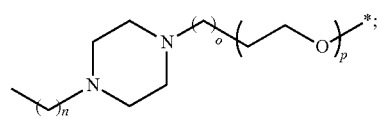

wherein, independently, n = 1-6; o = 0-6;
p = 2-6

DETAILED DESCRIPTION OF THE PREFERRED EMBODIMENTS

Figure 1:
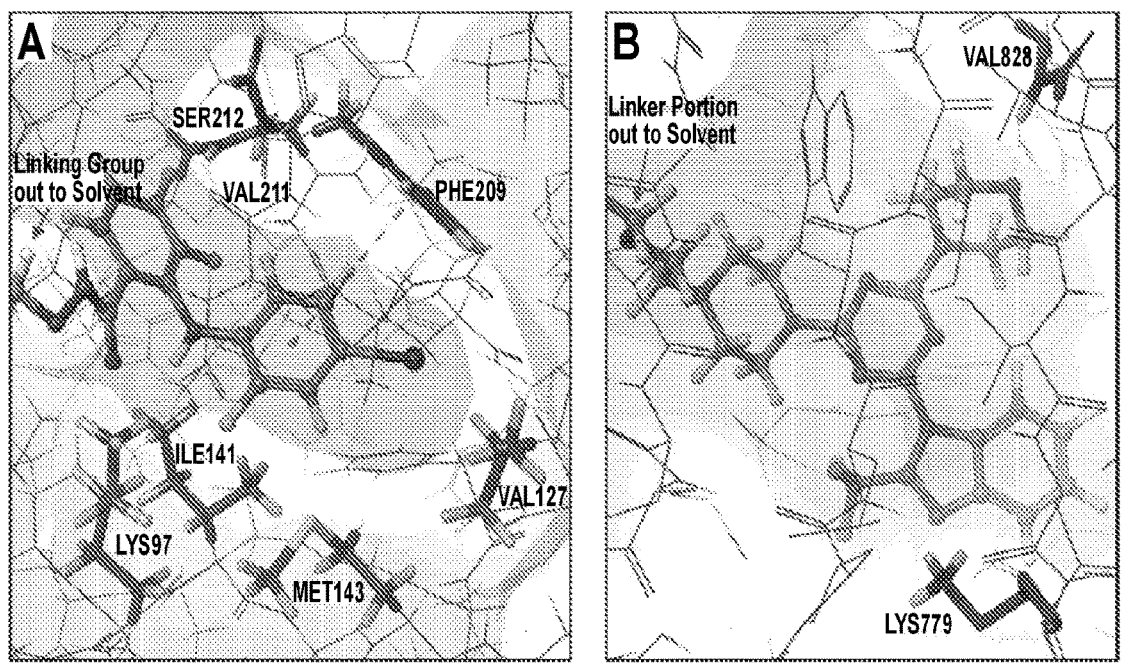
FIG. 1 shows the docked structure of compound 14 at MEK1 allosteric pocket (A) and at PI3Kα (B)

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "PI3K" as used herein means a Class I (including Class Ia and Class Ib), Class II, or Class III phosphonoinositide-3-kinase, as defined in U.S. Patent Publication No. 2011/0009405, incorporated herein by reference in its entirety.

The term "MEK" as used herein means mitogen-activated protein kinase.

The term "mTOR" as used herein means mechanistic target of rapamycin.

The term "a disease or condition wherein inhibition of mTOR and/or PI3K and/or MEK provides a benefit" pertains to a condition in which at least one of mTOR, PI3K, and MEK, and/or an action of at least one of mTOR, PI3K, and MEK, is important or necessary, e.g., for the onset, progress, expression of that disease or condition, or a disease or a condition which is known to be treated by an mTOR, PI3K, or MEK inhibitor. An example of such a condition includes, but is not limited to, a cancer. One of ordinary skill in the art is readily able to determine whether a compound treats a disease or condition mediated by one or more of mTOR, PI3K, and MEK for any particular cell type, for example, by assays which conveniently can be used to assess the activity of particular compounds.

The term "second therapeutic agent" refers to a therapeutic agent different from a present multifunctional inhibitor and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, compounds of the present invention are potent inhibitors of MEK and PI3K or mTOR, MEK, and PI3K and can be used in treating diseases and conditions wherein inhibition of mTOR and/or MEK and/or PI3K provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce mTOR, MEK, and PI3K signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a present multifunctional inhibitor can be administered at the same time or sequentially in any order at different points in time as a second therapeutic agent. A present multifunctional inhibitor and the second therapeutic agent can be administered separately, in any appropriate form and by any suitable route. When a present multifunctional inhibitor and the second therapeutic agent are not administered concurrently, it is understood that they can be administered in any order to a subject in need thereof. For example, a present multifunctional inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a present multifunctional inhibitor and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

Research has established that targeting mTOR, MEK, and PI3K using small molecule inhibitors is a viable cancer therapeutic strategy. However, cancers with KRAS mutation are known to be constitutively activated, refractory to standard of care, and a marker for poor prognosis. Two KRAS effector pathways, MAPK and PI3K, are important harbingers of proliferation and survival, respectively, and are mechanism of resistance for each other. Pre-clinical studies of cancers have shown that multiple inhibition of effector pathways have synergistic effects, which provides a rationale for combination therapies in a clinical setting.

The clinical relevance of these findings is currently being investigated in combination trials with MEK inhibitors administered with PI3K or AKT inhibitors (19). However, a non-promiscuous "single agent combination" drug offers a number of envisioned advantages over a rationally designed cocktail approach. First, off-target effects are compounded when combining two separate agents regardless of the selectivity of the individual components. Some off-target activities have proven advantageous for the treatment of unintended patient populations. For example, the "selective" abl kinase inhibitor imatinib has proven efficacious for the treatment of c-kit-driven GIST, as well as certain PDGFR-driven malignancies (20). However, in the greater number of instances, collateral damage in the form of non-mechanistic based toxicities occurs when unintended kinase targets are inhibited. Second, differing pharmacokinetic profiles between individual agents can be problematic when combining them in the clinic, which can be further compounded by differing drug-drug interaction liabilities. Issues of patient compliance and drug costs further support the design of single chemical entities to impair signaling through multiple nodes. Logistical hurdles also are encountered when conducting combination trials with two unapproved agents. While clinical data with the MEK inhibitor trametinib looks encouraging (21, 22), it is less likely that a PI3K or AKT inhibitor will be approved in the foreseeable future. Tumor cells are displaying a wide array of mechanisms to restore flux through the PI3K/AKT/mTOR pathway when challenged with a PI3K inhibitor, thereby limiting their single agent effectiveness and hindering their regulatory approval path (23). Favorable efficacy derived from horizontal, i.e. parallel, inhibitor of PI3K/AKT and MEK/ERK signaling, compared to single step targeting, has been borne out in early clinical data (19).

The present compounds are chemically-linked multifunctional inhibitors to specifically target both the MAPK and PI3K pathways. A single molecule having this combined pathway inhibition capability increases efficacy and safety over individual mono-targeting inhibitors. Administration of a single drug, as opposed to two drugs, also increases patient compliance with a prescribed treatment regimen.

The present invention is directed to new class of multifunctional inhibitors of MEK and PI3K or mTOR, MEK, and PI3K. The multifunctional MEK/PI3K inhibitors of the present invention therefore are useful in the treatment of cancers and precancers in subjects in need of such treatment. Also provided are methods of treating a subject comprising administering a therapeutically effective amount of a present compound to a subject in need of such treatment.

In one embodiment, the present invention is directed to compounds having the following bifunctional inhibitory activity against MEK and PI3K:

(a)

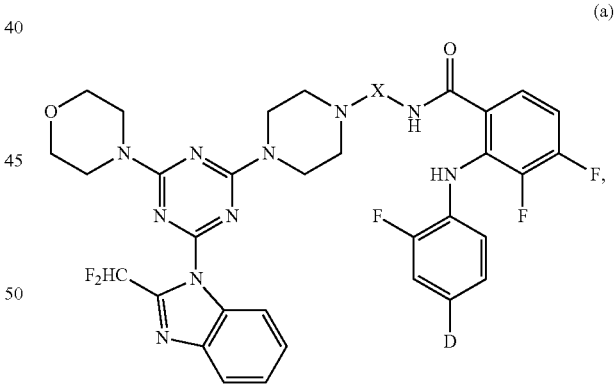

D is I, —C≡CH, or —C≡C—R, R is alkyl or aryl, and X is selected from the group consisting of

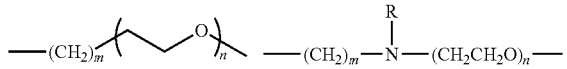

wherein m is 0, 1, 2, 3, 4, or 5 and n is 1, 2, 3, 4, or 5 or any combination of m and n R = H, alkyl, or aryl
m, n independently are 1, 2, 3, 4, or 5

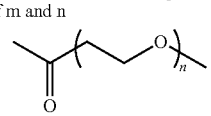

n is 1, 2, 3, 4, or 5

-continued

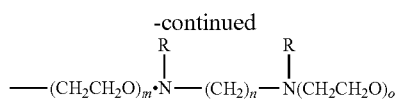

R independently is H, alkyl, or aryl
m, n, o independently are 1, 2, 3, 4, or 5

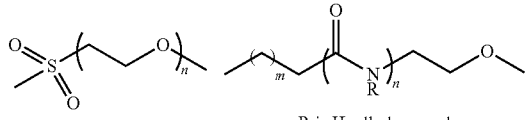

n is 1, 2, 3, 4, or 5

R is H, alkyl, or aryl
where m is 0, 1, 2, 3, 4, or 5
and n is 1, 2, 3, 4, or 5
or any combination of m and n

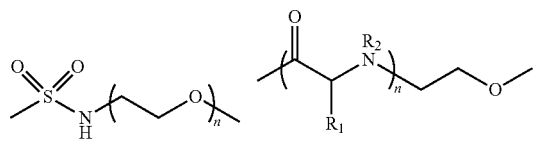

n is 1, 2, 3, 4, or 5

$R_1$, $R_2$ independently are, H, alkyl, or aryl
n is 1, 2, 3, 4, or 5

(b)

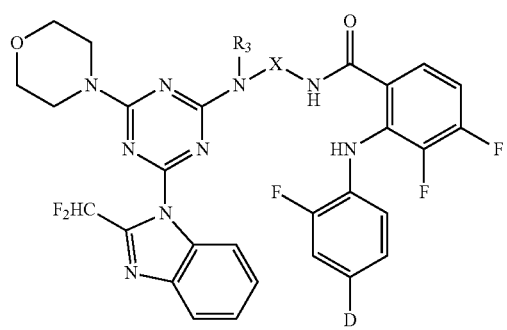

D = I, —C≡CH, —C≡C—R where R = alkyl or aryl
$R_3$ is H, alkyl, aryl, —(CH$_2$)$_p$—OH, or
—(CH$_2$)$_p$—NR$_4$ where p = 1-6 and $R_4$ = H, alky, aryl
and X is selected from the group consisting of

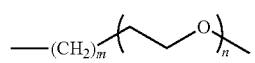

m is 0, 1, 2, or 3, and n is 1, 2, 3, 4, or 5
or any combination of m and n

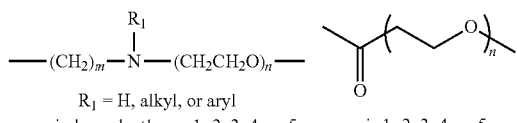

$R_1$ = H, alkyl or aryl
m, n independently are 1, 2, 3, 4, or 5 n is 1, 2, 3, 4, or 5

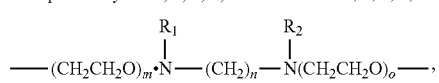

$R_1$ = H, alkyl, or aryl
m, n, o independently are 1, 2, or 3

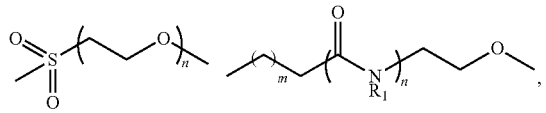

n is 1, 2, 3, 4, or 5

$R_1$ = H, alkyl, or aryl
m, n, o independently are 1, 2, or 3

-continued

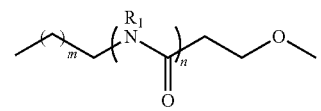

n is 1, 2, 3, 4, or 5

$R_1$ = H, alkyl, or aryl
m is 0, 1, 2, 3, 4, or 5, and
n is 1, 2, 3, 4, or 5 or any
combination of m and n

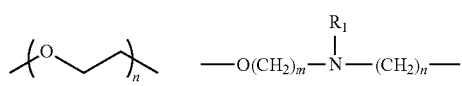

$R_1$, $R_2$ independtly are H, alkyl, aryl
n is 1, 2, 3, 4, or 5

(c)

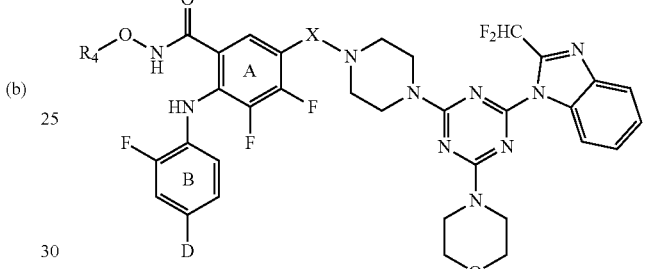

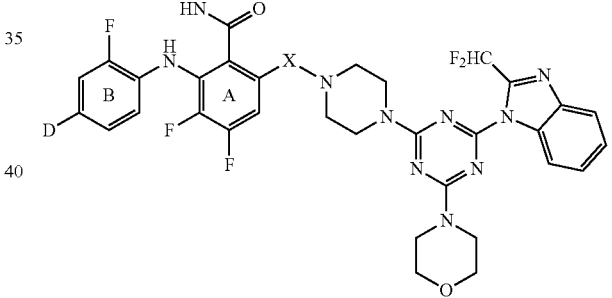

where $R_4$ = R-(-)-CH$_2$CHOH(CH$_2$OH);
—CH$_2$CH$_2$OH; or —CH$_2$CH$_2$—NH$_2$;
D is I, —C≡CH, or —C≡C—R;
R is alkyl or aryl, and X is selected from the
group consisting of

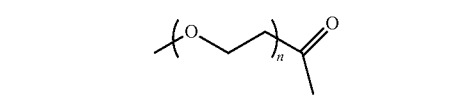

n is 1, 2, 3, 4, or 5

$R_1$ is H, alkyl, or aryl
m and n independently are 1, 2, 3, 4, or 5

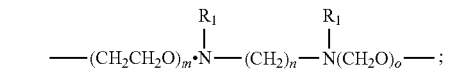

n is 1, 2, 3, 4, or 5

$R_1$ independently is H, alkyl, or aryl
m, n, and o independently are 1, 2, 3, 4, or 5

-continued (d)

[Structure: morpholine-triazine-difluoromethylbenzimidazole with X linker to C(=O)NH-benzamide with fluorines and NH-aryl(F, D)]

D is I, —C≡CH, or —C≡C—R, R is alkyl or aryl,
X is selected from the group consisting of —(CH$_2$)$_m$(O)$_n$—
where m is 0, 1, 2, 3, 4, or 5
and n is 1, 2, 3, 4, or 5
or any combination of m and n —(CH$_2$)$_m$—N(R)—(CH$_2$CH$_2$O)$_n$—
R = H, alkyl, or aryl
m, n independently are 1, 2, 3, 4, or 5

—C(=O)—(CH$_2$CH$_2$O)$_n$—
n is 1, 2, 3, 4, or 5

—(CH$_2$CH$_2$O)$_m$·N(R$_1$)—(CH$_2$)$_n$—N(R$_1$)(CH$_2$CH$_2$O)$_o$—
R$_1$ independently is H, alkyl, or aryl
m, n, o independently are 1, 2, 3, 4, or 5

[SO$_2$-(CH$_2$CH$_2$O)$_n$ structure]
n is 1, 2, 3, 4, or 5

[C(=O)-(CH$_2$)$_m$-C(=O)-N(R$_1$)-CH$_2$CH$_2$-N(R$_1$)-OCH$_3$ structure]
R$_1$ is H, alkyl, or aryl
where m is 0, 1, 2, 3, 4, or 5
and n is 1, 2, 3, 4, or 5

[MeSO$_2$-NH-(CH$_2$CH$_2$O)$_n$ structure]
n is 1, 2, 3, 4, or 5

[C(=O)-CH(R$_1$)-N(R$_2$)-(CH$_2$CH$_2$-OCH$_3$)$_n$ structure];
R$_1$, R$_2$ independently are H, alkyl, or aryl
n is 1, 2, 3, 4, or 5

(e)

[Structure: morpholine-triazine-difluoromethylbenzimidazole with X-N(R$_5$)-W-N(R$_6$)-Z-SO$_2$-NH-aryl(F, D) and NH-aryl(Y, F)]

Y is F, Cl
D is I or —C≡CR, where R = H, alkyl or aryl
R$_5$, R$_6$, independently, are H, alkyl, aryl, or taken together to form a 5- or 6- membered ring;
X, W, and Z, independently, are carbonyl or (CR$_1$R$_2$)$_n$
where R$_5$, R$_6$, independently, are H, alkyl, or aryl, and
n = 0, 1, 2, 3, 4, or 5;
x is —(CH$_2$)$_m$—N(R)—(CH$_2$)$_n$—
R = H, alkyl, aryl
where m, n, independently,
are 1, 2, 3, 4, or 5

—(CH$_2$CH$_2$O)$_m$—N(R)—(CH$_2$)$_n$—; and
R = H, alkyl, aryl
where m, n, independently,
are 1, 2, 3, 4, or 5

(f)

[Structure: morpholine-triazine-difluoromethylbenzimidazole with piperazine-X-NH-C(=O)-benzamide with fluorines and HN-aryl(F, F, D)]

wherein D is I, —C≡CH, or —C≡C—R,
R is alkyl or aryl, and X is selected from the group consisting of:

*—C(=O)—(CH$_2$)$_m$—(O)$_n$—(CH$_2$)$_o$—(N(R$_1$))$_p$—(CH$_2$)$_q$—(CH$_2$CH$_2$O)$_r$—,
R$_1$, independently, is H, alkyl, or aryl, wherein, independently,
m = 0, 1; n = 0-6; o = 0-6; p = 0, 1; q = 0-6; r = 2-6

[SO$_2$-(CH$_2$)$_m$-O-(CH$_2$CH$_2$O)$_n$ structure],
wherein, independently,
m = 0-6; n = 2-6

*—C(=O)—(CH$_2$)$_m$—(O)$_n$—(CH$_2$)$_o$—N(R$_1$)—(CH$_2$)$_p$—N(R$_2$)—(CH$_2$CH$_2$O)$_q$—,
wherein, independently, m = 0, 1; n = 0-6; o = 0-6; p = 1-6;
q = 2-6, and R$_1$, R$_2$, independently, are H, alkyl, or aryl

[MeSO$_2$-NH-(CH$_2$)$_m$-O-(CH$_2$CH$_2$O)$_n$ structure],
wherein independently,
m = 0-6; n = 2-6

*—C(=O)—(CH$_2$)$_m$—piperazine—(CH$_2$)$_n$—(CH$_2$CH$_2$O)$_o$—(O)$_p$—*,
wherein, independently, m = 0, 1; n = 0-6; o = 0-6;
p = 2-6

-continued

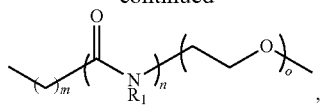

R₁, independently, is H, alkyl, or aryl, wherein, independently, m = 0-6; n = 1-6; o = 2-6

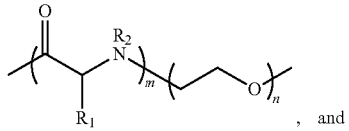

, and

R₁, R₂, independently, are H, alkyl, or aryl, wherein, independently, m = 1-6; n = 2-6

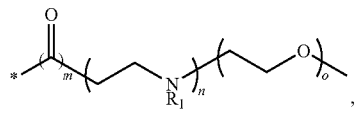

wherein, independently, m = 0, 1; n = 1-6; o = 2-6 or a pharmaceutically acceptable salt thereof.

In the above structures, the most preferred ranges are disclosed for the variable m, n, o, p, q, and r. In additional embodiments, m is 0-20, preferably 1-10; n is 0-20, preferably)-10; o is 0-20, preferably 1-15 or 2-10; p is 1-20, preferably 2-15 or 1-10; and q is 0-20, preferably 1-15 or 2-10. The above range includes each individual value within the recited range and all subranges within the disclosed ranges.

In another embodiment, the present invention is directed to trifunctional compounds capable of inhibiting mTOR, MEK, and PI3K activity having a following structural formula:

(a)

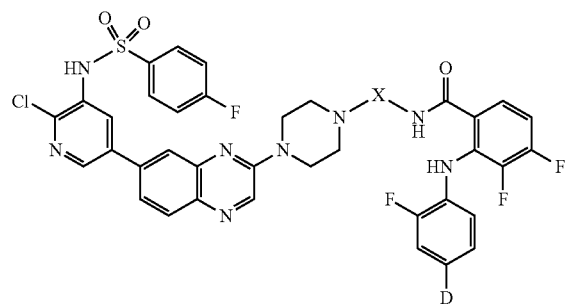

wherein D is I, —C≡CH, or —C≡C—R,
R = alkyl or aryl, and X is selected from the group consisting of:

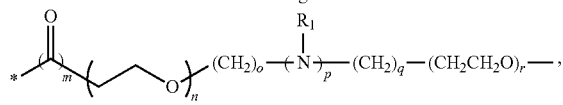

R₁, independently, is H, alkyl, or aryl, wherein, independently,
m = 0, 1; n = 0-6; o = 0-6; p = 0, 1; q = 0-6; r = 2-6

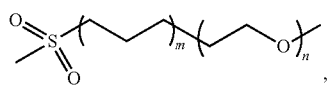

wherein, independently,
m = 0-6; n = 2-6

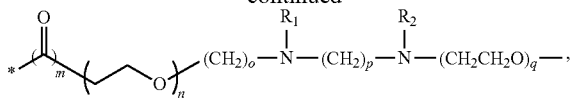

wherein, independently, m = 0, 1; n = 0-6; o = 0-6; p = 1-6;
q = 2-6 and R₁, R₂, independently, are H, alkyl, or aryl

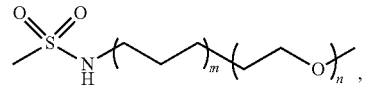

wherein independently,
m = 0-6; n = 2-6

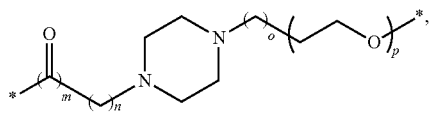

wherein, independently, m = 0, 1; n = 0-6; o = 0-6;
p = 2-6

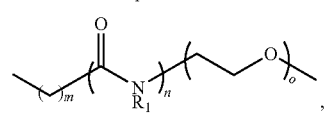

R₁, independently, is H, alkyl, or aryl, wherein,
independently, m = 0-6; n = 1-6 o = 2-6

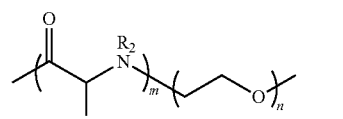

, and

R₁, R₂, independently, are H, alkyl, or aryl
wherein, independently, m = 1-6; n = 2-6

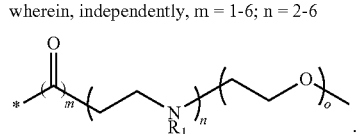

R₁, independently, is H, alkyl, or aryl,
wherein, independently, m = 0, 1; n = 1-6; o = 2-6

(b)

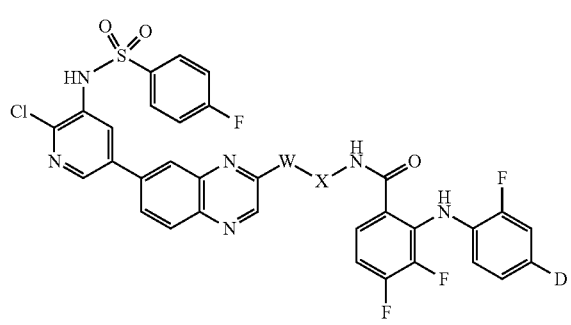

where W is ( —N⟨piperidine⟩ ) or ⟨N(R)(CH₂)ₘ⟩ and R is H, alkyl or aryl and m = 0, 1-6;
D = I, —C≡CH, —C≡C—R,
where R = alkyl or aryl, wherein X is selected from the group consisting of:

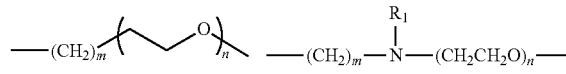

where m = 0, 1-6; n = 1-6;
or any combination of m and n

R₁ = H, alkyl or aryl where
m, n independently are 1-6

-continued

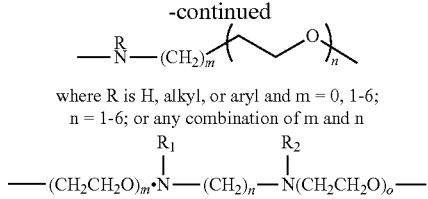

where R is H, alkyl, or aryl and m = 0, 1-6;
n = 1-6; or any combination of m and n —(CH₂CH₂O)$_m$•N(R$_1$)—(CH₂)$_n$—N(R$_2$)(CH₂CH₂O)$_o$—

R$_1$, R$_2$ are independently H, alkyl or aryl
and m, n, o independently are 1-6

(c)

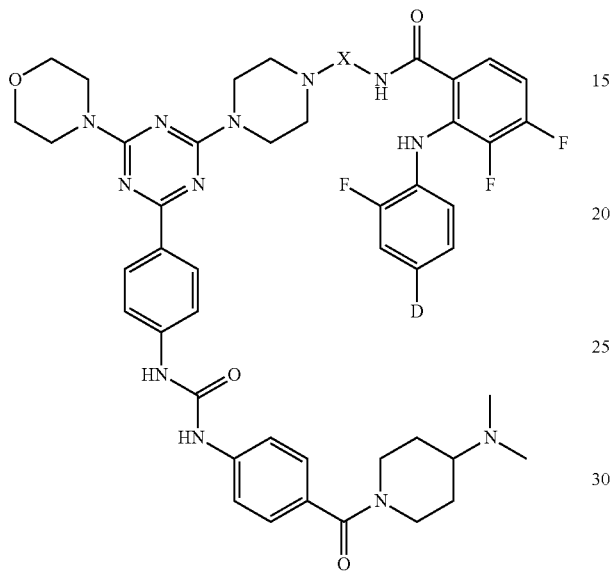

wherein D is I, —C≡CH, or —C≡C—R,
R = alkyl or aryl, and X is selected from the group
consisting of:

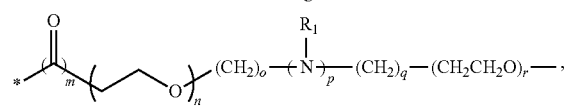

R$_1$, independently, is H, alkyl, or aryl, wherein, independently,
m = 0, 1; n = 0-6; o = 1-6; p = 0, 1; q = 0-6; r = 2-6

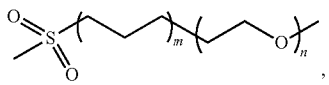

wherein, independently,
m = 0-6; n = 2-6

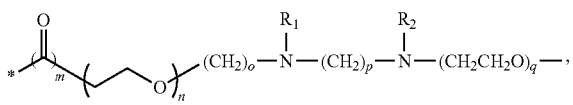

wherein, independently, m = 0, 1; n = 0-6; o = 1-6; p = 1-6;
q = 2-6 and R$_1$, R$_2$, independently, are H, alkyl, or aryl

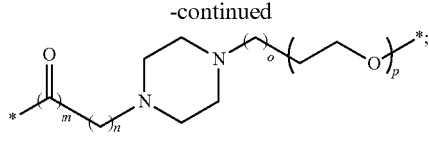

wherein independently,
m = 0-6; n = 2-6

-continued

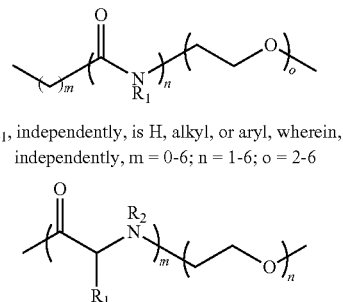

wherein, independently, m = 0, 1; n = 0-6; o = 0-6;
p = 2-6

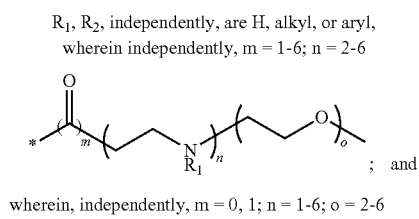

R$_1$, independently, is H, alkyl, or aryl, wherein,
independently, m = 0-6; n = 1-6; o = 2-6

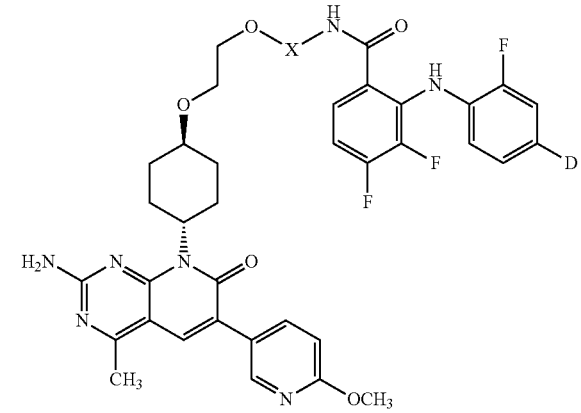

R$_1$, R$_2$, independently, are H, alkyl, or aryl,
wherein independently, m = 1-6; n = 2-6

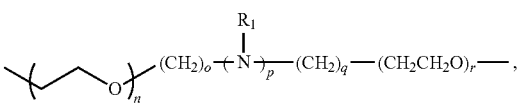

; and wherein, independently, m = 0, 1; n = 1-6; o = 2-6

(d)

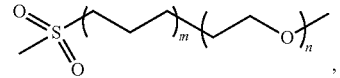

wherein D is I, —C≡CH, or —C≡C—R,
R = alkyl or aryl, and X is selected from the group
consisting of:

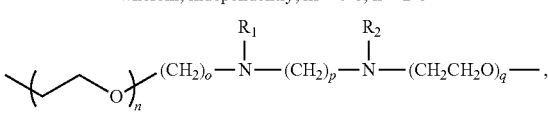

R$_1$, independently, is H, alkyl, or aryl wherein, independently,
n = 0-6; o = 1-6; p = 0, 1; q = 0-6; r = 2-6

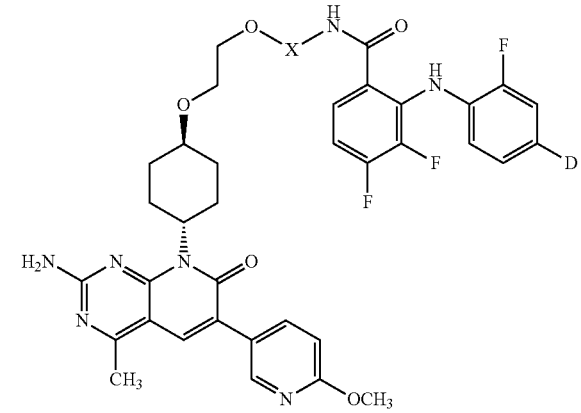

wherein, independently, m = 0-6; n = 2-6

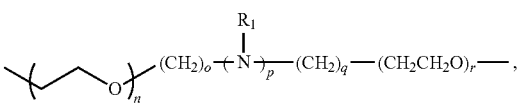

wherein, independently, n = 0-6; o = 1-6; p = 1-6;
q = 2-6; and R$_1$, R$_2$, independently, is H, alkyl, or aryl -continued

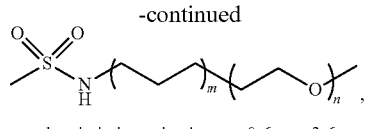

wherein independently, m = 0-6; n = 2-6

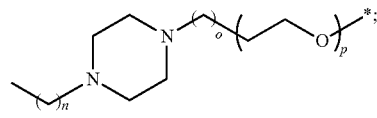

wherein, independently, n = 1-6; o = 0-6;
p = 2-6

and $R_1$, independently, is H, alkyl, or aryl, wherein independently m = 1-6; n = 1-6; o - 2-6

;

$R_1$, independently, is H, alkyl, or aryl,
wherein independently m = 1-6; n = 2-6 or a pharmaceutically acceptable salt thereof.

The present invention encompasses bifunctional compounds, trifunctional compounds, and tetrafunctional compounds that inhibit at least two of mTOR, MEK, and PI3K, and that are useful in the treatment of a variety of diseases and conditions. In particular, the present multifunctional compounds are used in methods of treating a disease or condition wherein inhibition of mTOR and/or MEK and/or PI3K provides a benefit, for example, cancers. The method comprises administering a therapeutically effective amount of a present multifunctional compound to an individual in need thereof. The present methods also encompass administering a second therapeutic agent to the individual in addition to the present multifunctional compound. The second therapeutic agent is selected from drugs known as useful in treating the disease or condition afflicting the individual in need thereof, e.g., a chemotherapeutic agent and/or radiation known as useful in treating a particular cancer.

As used herein, the term "alkyl" refers to straight chained and branched saturated $C_{1-10}$ hydrocarbon groups including, but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethylbutyl. The term $C_n$ means the alkyl group has "n" carbon atoms. The term $C_{n-m}$ means that alkyl groups can have from "n" to "m" carbon atoms. The term "alkylene" refers to an alkyl group having a substituent. An alkyl, e.g., methyl, or alkylene, e.g., —$CH_2$—, group can be substituted with halo, trifluoromethyl, trifluoromethoxy, hydroxy, alkoxy, nitro, cyano, alkylamino, or amino groups, for example.

As used herein, the term "halo" is defined as fluoro, chloro, bromo, and iodo.

The term "hydroxy" is defined as —OH.
The term "alkoxy" is defined as —OR, wherein R is alkyl.
The term "amino" is defined as —$NH_2$, and the term "alkylamino" is defined as —$R_2$, wherein at least one R is alkyl and the second R is alkyl or hydrogen.
The term "nitro" is defined as —$NO_2$.
The term "cyano" is defined as —CN.
The term "carbamoyl" is defired as —C(=O)$NR_2$.
The term "trifluoromethyl" is defined as —$CF_3$.
The term "trifluoromethoxy" is defined as —$OCF_3$.
As used herein, groups such as

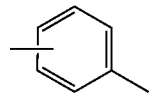

is an abbreviation for

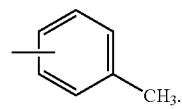

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, in which one of the rings is aromatic and the other ring(s) can be saturated, partially unsaturated, or aromatic, for example, dihydronaphthyl, indenyl, indanyl, or tetrahydronaphthyl (tetralinyl).

The term "heteroaryl" refers to 3- to 10-membered ring structures, preferably 3- to 7-membered rings, whose ring structures include one to four heteroatoms. Examples of heteroaryl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinolone, phthalazine, naphthyridine, quinoxaline, quinazoline, cinnoline, pteridine, carbazole, phenanthridine, acridine, pyrimidine, phenathroline, and the like.

An aryl or heteroaryl group can be substituted at one or more position with substiutents, for example, halogen, alkyl, aralkyl, cycloalkyl, hydroxyl, amino, nitro, sulfhydryl, imino, amido, phosphate, phosphinate, carbonyl, carboxyl, silyl, alkylthio, sulfonyl, ketone, aldehyde, ester, a heterocyclyl, an aryl or heteroaryl moiety, trifluoromethyl, cyano, and the like.

Additionally, salts, hydrates, and solvates of the present compounds also are included in the present invention and can be used in the methods disclosed herein. The invention further includes all possible stereoisomers and geometric isomers of the present multifunctional compounds. The present invention includes both racemic compounds and optically active isomers. When a present multifunctional compound or trifunctional compound is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of a present multifunctional compound is possible, the invention is intended to include all tautomeric forms of the compound.

Compounds of the invention can exist as salts. Pharmaceutically acceptable salts of the compounds of the invention often are preferred in the methods of the invention. As used herein, the term "pharmaceutically acceptable salt" refers to a salt or zwitterionic form of the present multifunctional compounds. Salts of the present multifunctional compounds can be prepared during the final isolation and purification of the compounds or separately by reacting the compound with an acid having a suitable cation. The pharmaceutically acceptable salts of the present multifunctional compounds can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isothionate, salicylate, methanesulfonate, mesitylenesulfonate, naphthylenesulfonate, nicotinate, 2-naphthalenesulfonate, oxalate, palmoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include the present multifunctional compounds as well as pharmaceutically acceptable salts, hydrates, or solvates thereof.

The term "prodrug," as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, toxicity, lack of specificity, or limited bioavailability.

Prodrugs often offer advantages of solubility, tissue compatibility, or delayed release in the mammalian organism. (See e.g., Bundgard, "Design of Prodrugs", pp. 7-9, 21-24, Elsevier, Amsterdam (1985); and Silverman, "The Organic Chemistry of Drug Design and Drug Action", pp. 352-401, Academic Press, San Diego, Calif. (1992)). Exemplary prodrugs comprise an active drug molecule itself and a chemical masking group (e.g., a group that reversibly suppresses the activity of the drug). Some preferred prodrugs are variations or derivatives of compounds that have groups cleavable under metabolic conditions. Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Common prodrugs include acid derivatives such as esters prepared by reaction of parent acids with a suitable alcohol (e.g., a lower alkanol), amides prepared by reaction of the parent acid compound with an amine, or basic groups reacted to form an acylated base derivative (e.g., a lower alkylamide).

Additional PI3K inhibitors that can be linked to an MEK inhibitor and/or mTOR inhibitor include

| Compound | Structure | IC$_{50}$ (nM) | | | |
|---|---|---|---|---|---|
| | | PI3Kα | PI3Kβ | PI3Kγ | PI3Kδ |
| ST-177 | 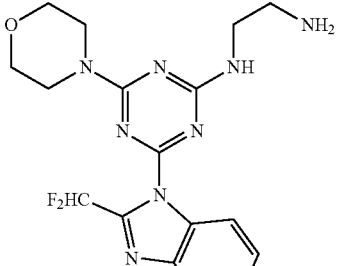 | 292 ± 31 | 2117 ± 444 | 771 ± 63 | 291 ± 32 |
| ST-5-02 | 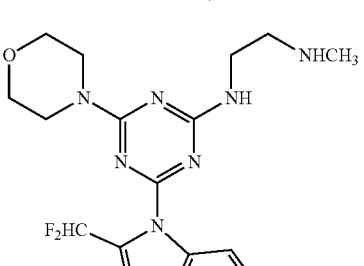 | 248 ± 24 | 2900 ± 375 | 681 ± 90 | 135 ± 19 |

-continued
| Compound | Structure | IC$_{50}$ (nM) | | | |
| --- | --- | --- | --- | --- | --- |
| | | PI3Kα | PI3Kβ | PI3Kγ | PI3Kδ |
| ST-187 | 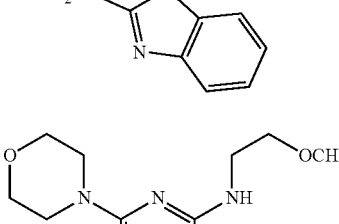 | 9.9 ± 1.2 | 71 ± 8 | 54 ± 1 | 8.1 ± 1.7 |
| ST-178 | 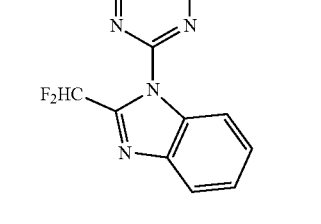 | 20 ± 3 | 208 ± 15 | 64 ± 5 | 17 ± 1 |
| ZSTK474 | 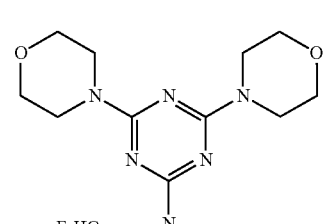 | 5.0 ± 0.8 | 15.2 ± 1.4 | 20.8 ± 0.6 | 3.9 ± 0.6 |
| ST-5-03 | 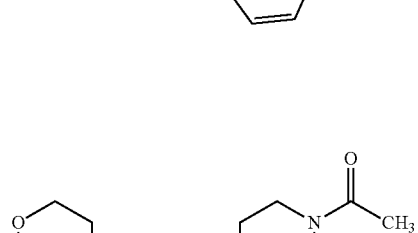 | 8.2 ± 0.7 | 14.3 ± 2.5 | 21 ± 1 | 2.9 ± 0.6 |

-continued

| Compound | Structure | IC$_{50}$ (nM) | | | |
|---|---|---|---|---|---|
| | | PI3Kα | PI3Kβ | PI3Kγ | PI3Kδ |
| ST-167 | 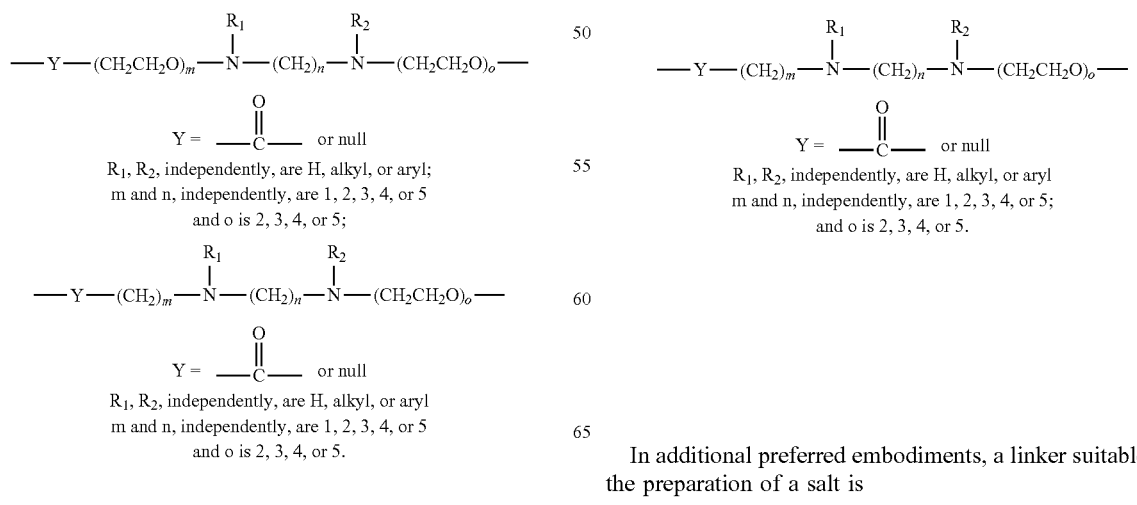 | 11.5 ± 0.1 | 214 ± 49 | 140 ± 6.6 | 1.3 ± 0.2 |
| ST-5-21 | 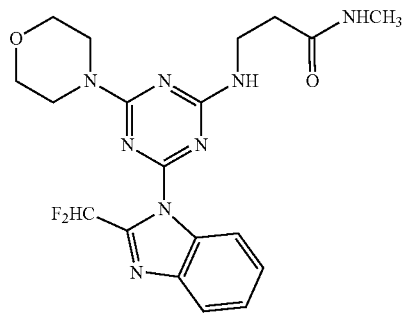 [SMILES: CNC(=O)CCNc1nc(N2CCOCC2)nc(-n2c(C(F)F)nc3ccccc32)n1] | 20 ± 0.4 | 431 ± 83 | 67 ± 2.8 | 26 ± 4.9 |
| ST-5-25 | 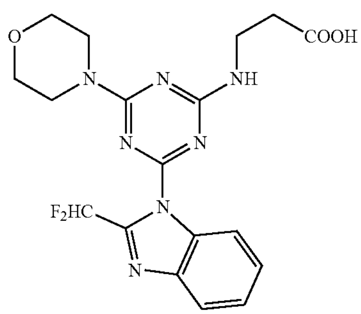 [SMILES: O=C(O)CCNc1nc(N2CCOCC2)nc(-n2c(C(F)F)nc3ccccc32)n1] | 12.4 ± 0.7 | 787 ± 106 | 22.3 ± 0.7 | 60 ± 3.4 |

Preferred linkers for attachment of mTOR, MEK, and PI3K inhibitors for the preparation of salts are:

$$\text{—Y—(CH}_2\text{CH}_2\text{O)}_m\text{—}\underset{R_1}{\text{N}}\text{—(CH}_2\text{)}_n\text{—}\underset{R_2}{\text{N}}\text{—(CH}_2\text{CH}_2\text{O)}_o\text{—}$$

$$Y = \overset{O}{\underset{}{—C—}} \text{ or null}$$

R$_1$, R$_2$, independently, are H, alkyl, or aryl;
m and n, independently, are 1, 2, 3, 4, or 5
and o is 2, 3, 4, or 5;

$$\text{—Y—(CH}_2\text{)}_m\text{—}\underset{R_1}{\text{N}}\text{—(CH}_2\text{)}_n\text{—}\underset{R_2}{\text{N}}\text{—(CH}_2\text{CH}_2\text{O)}_o\text{—}$$

$$Y = \overset{O}{\underset{}{—C—}} \text{ or null}$$

R$_1$, R$_2$, independently, are H, alkyl, or aryl
m and n, independently, are 1, 2, 3, 4, or 5
and o is 2, 3, 4, or 5.

$$\text{—Y—(CH}_2\text{)}_m\text{—}\underset{R_1}{\text{N}}\text{—(CH}_2\text{)}_n\text{—}\underset{R_2}{\text{N}}\text{—(CH}_2\text{CH}_2\text{O)}_o\text{—}$$

$$Y = \overset{O}{\underset{}{—C—}} \text{ or null}$$

R$_1$, R$_2$, independently, are H, alkyl, or aryl
m and n, independently, are 1, 2, 3, 4, or 5
and o is 2, 3, 4, or 5.

In additional preferred embodiments, a linker suitable for the preparation of a salt is

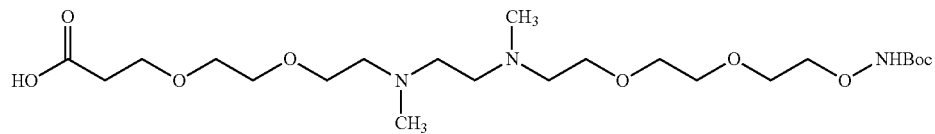 [SMILES: CN(CCOCCOCCONC(=O)OC(C)(C)C)CCN(C)CCOCCOCCC(=O)O]

t-Boc-aminoxy-PEG2-N',N''-dimethylethane-1,2-diamine-PEG2 acid (ST-179)

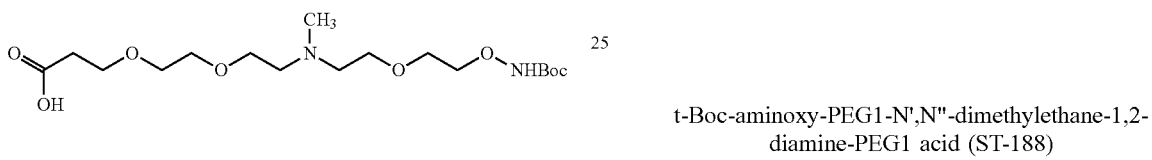

t-Boc-aminoxy-PEG1-N-methylamine-PEG1 acid (ST-5-09)

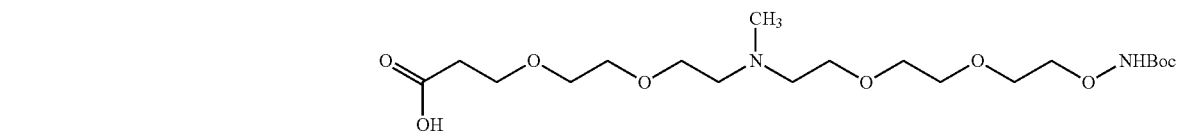 [SMILES: CN(CCOCCOCCONC(=O)OC(C)(C)C)CCOCCOCCC(=O)O]

t-Boc-aminoxy-PEG1-N-methylamine-PEG2 acid (ST-5-10)

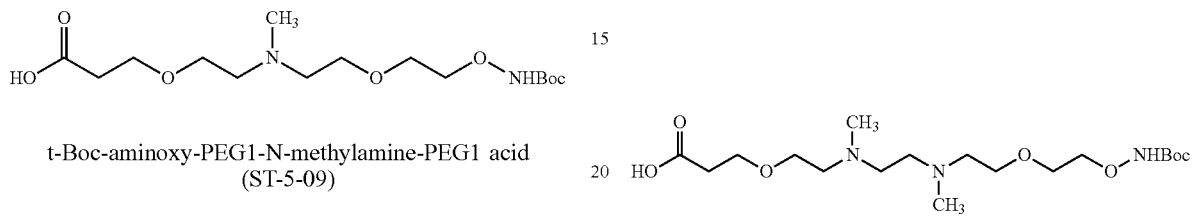

t-Boc-aminoxy-PEG1-N',N''-dimethylethane-1,2-diamine-PEG1 acid (ST-188)

t-Boc-aminoxy-PEG2-N-methylamine-PEG2 acid (ST-5-11)

In one embodiment of compound (e), the linker

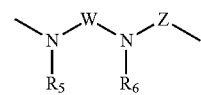

is

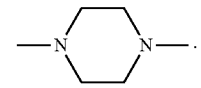

To yet further enhance drug bioavailability, the linker can be 2-[2,3-bis(2-hydroxyethoxy)propxy]ethanol, a ternary linker, or pentaerythritol, a quaternary linker, for linking MEK, PI3K, and mTOR inhibitors via ester bonds.

Specific compounds of the present invention capable of inhibiting mTOR, PI3K, and MEK include, but are not limited to, compounds having the structures set forth below.

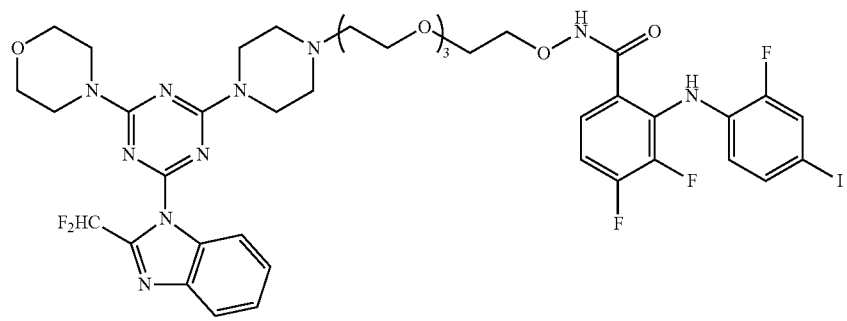
ST-162
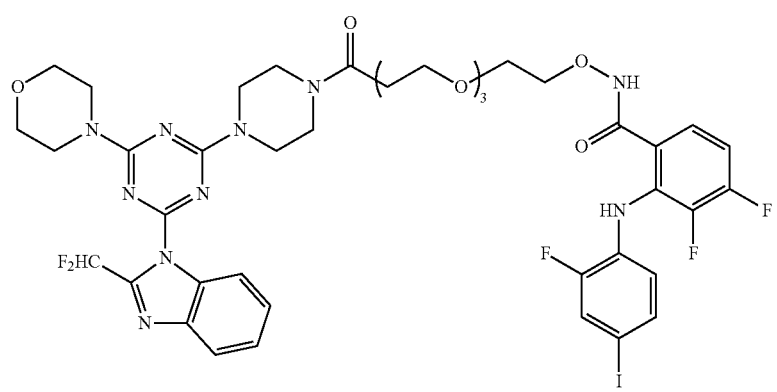
ST-168
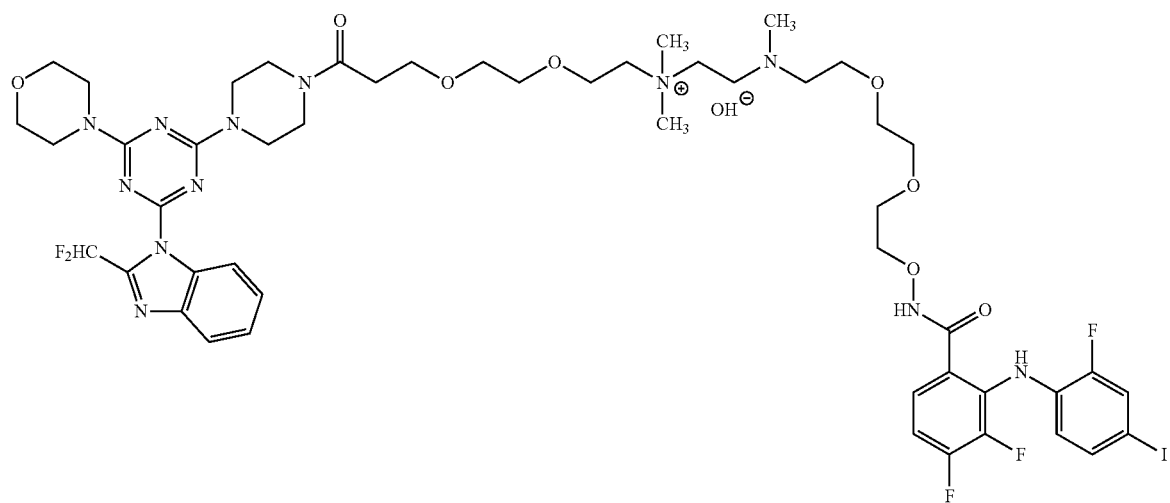
Structure A

Structure B
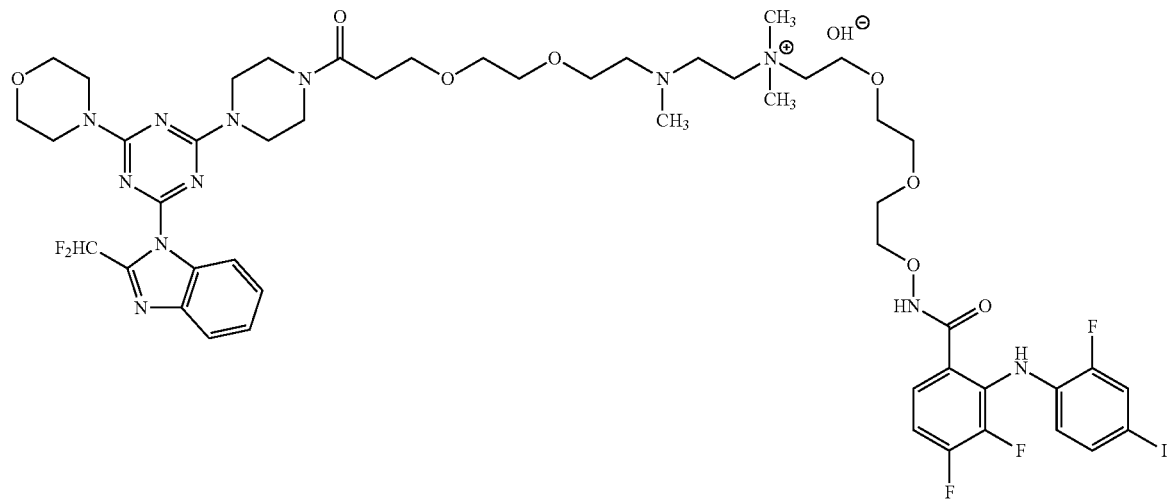
ST-180
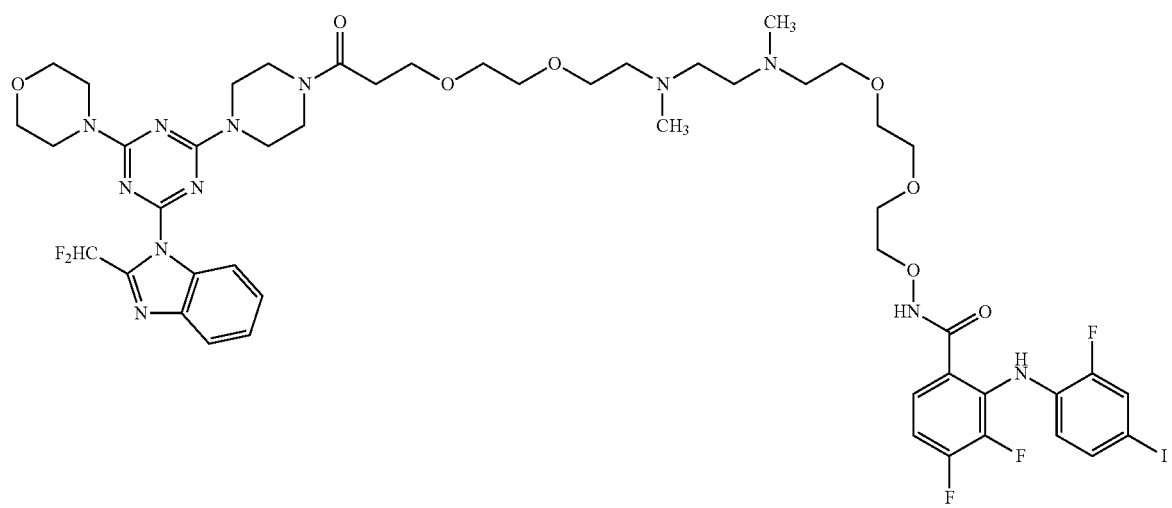
ST-189
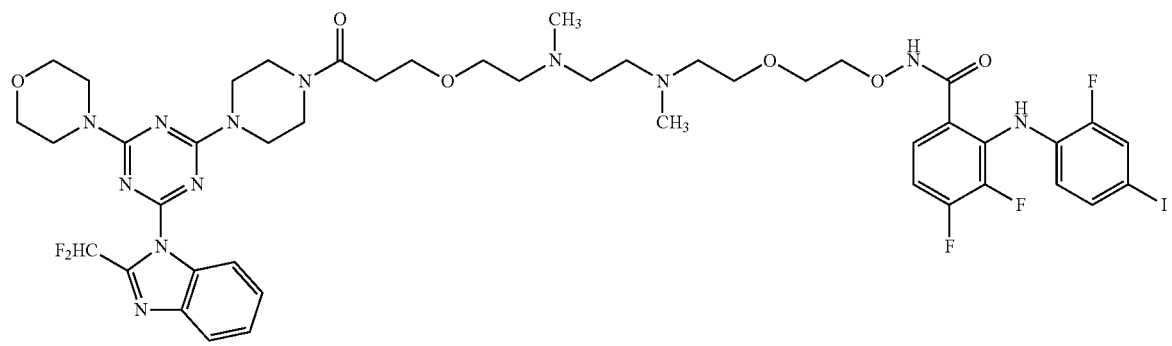

ST-181
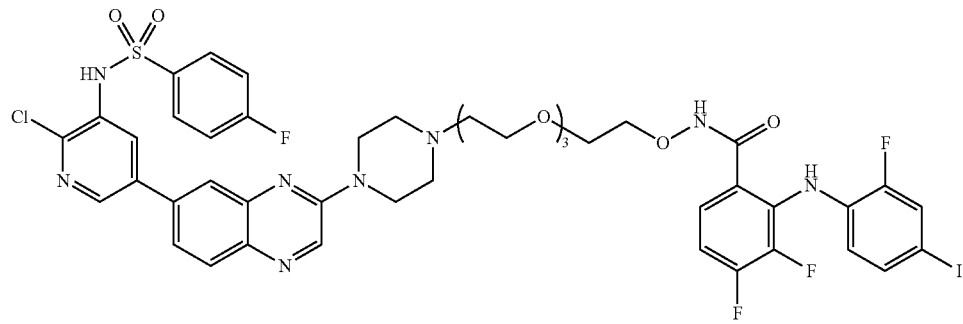
ST-182
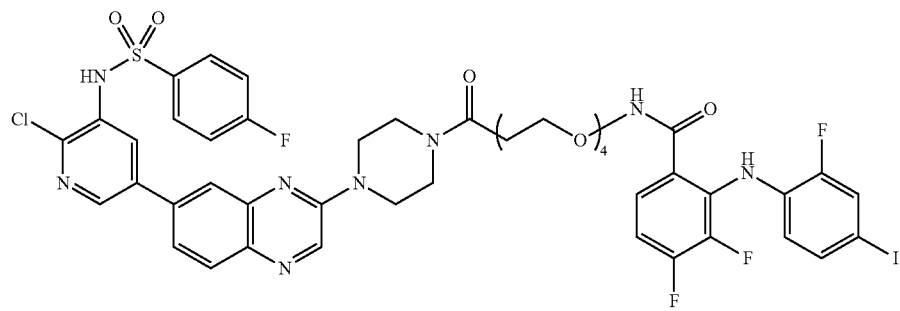
ST-183
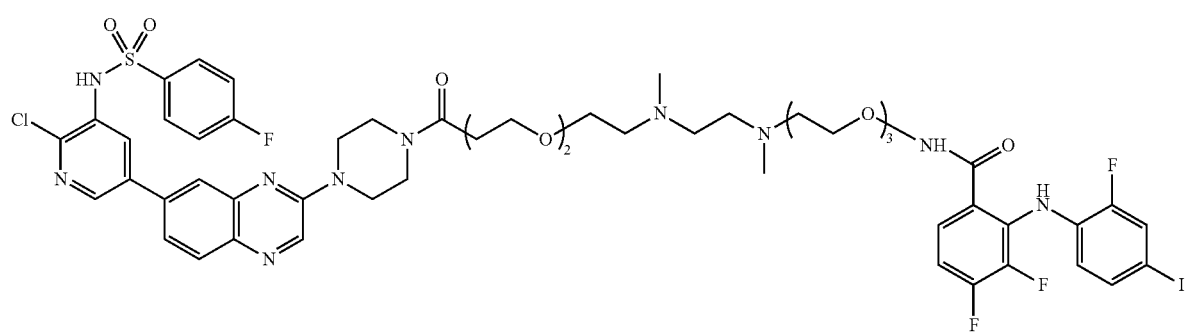
ST-5-35
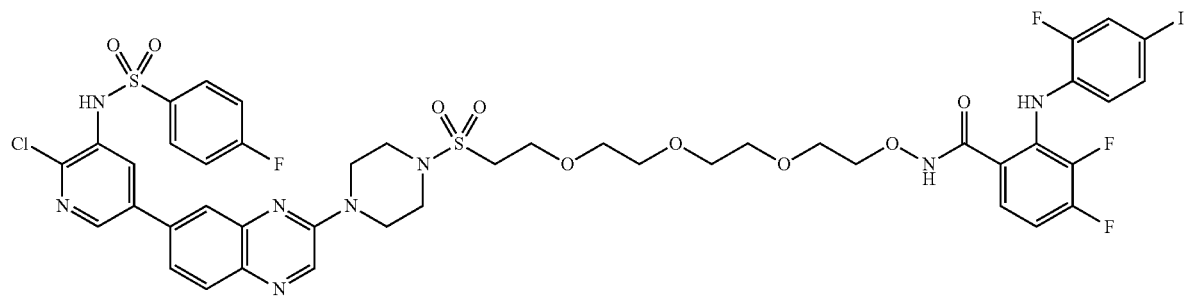
ST-5-36
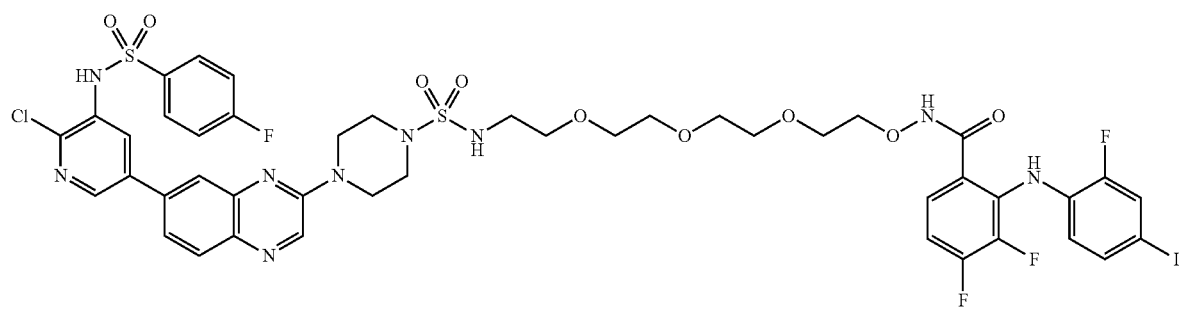

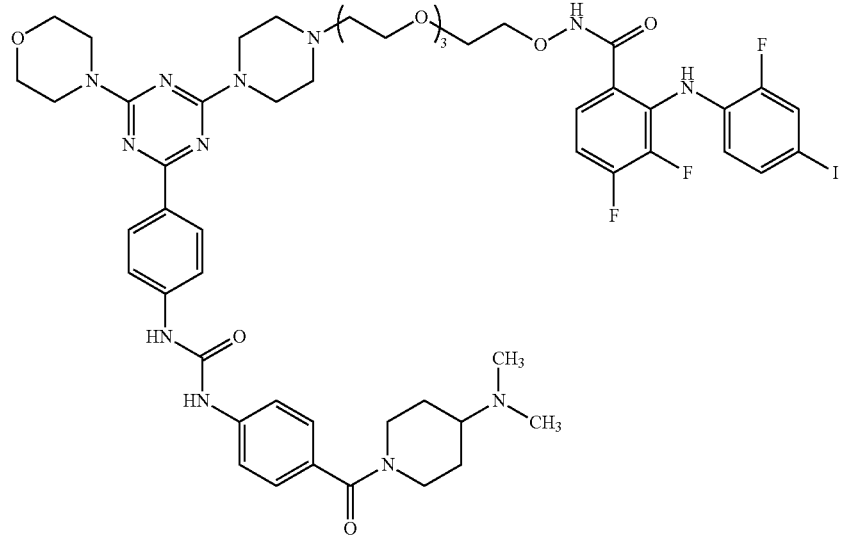
ST-184
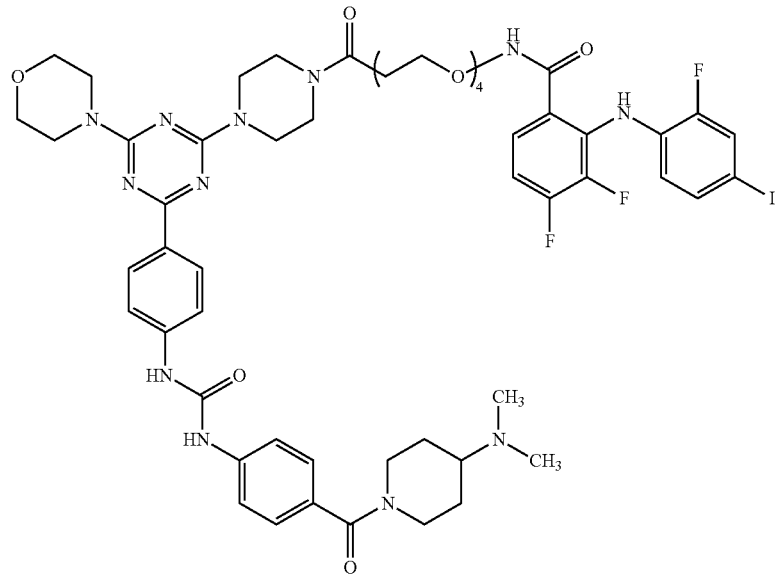
ST-185

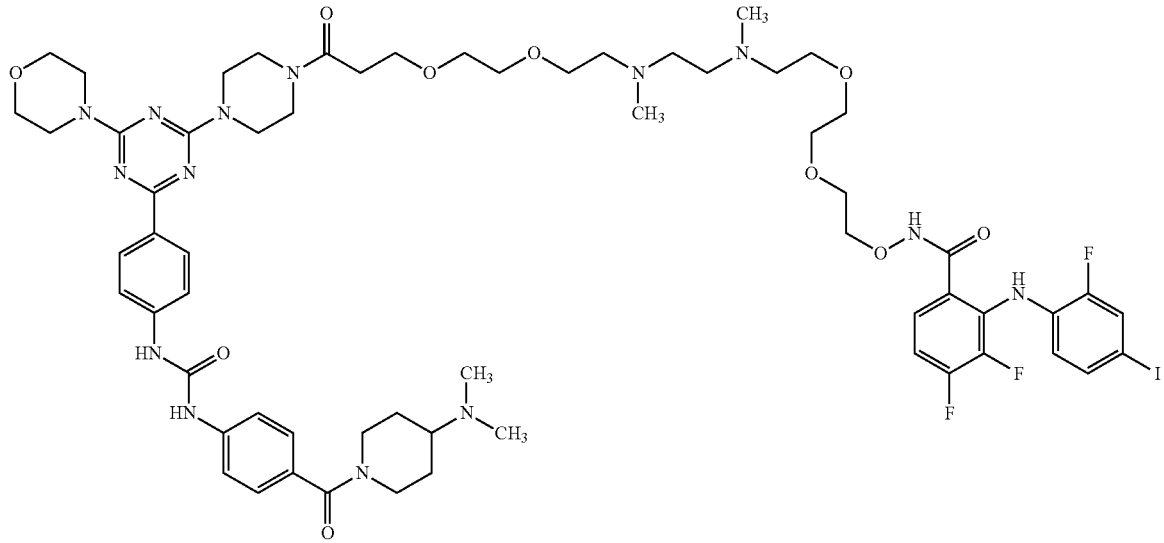

ST-186

The present invention includes (a) development of individual mTOR, PI3K, and MEK inhibitors that are chemically modified with conjugating linkers to maintain high-binding affinity towards their respective enzyme targets; and (b) conjugation of these chemical entities in a final synthetic step to provide the prototype single chemical entity multifunctional inhibitor compounds ST-180 through ST-186, ST-189, and ST5-05. This strategy could also be used to link alternate MEK inhibitors such as Trametinib, Selumetinib, Pimersertib, SMK-17, for example. Other MEK inhibitors are disclosed in Chapter 8, FIGS. 8.10 and 8.11: Sebolt-Leopold, et al. (2009), *Road to PD0325901 and Beyond: The MEK Inhibitor Quest, in Kinase Inhibitor Drugs* (Eds. R. Li and J. A. Stafford), John Wiley & Sons, Inc., Hoboken, N.J., USA.

Alternate PI3K inhibitors include, for example, GDC 0941, GDC 0980, BKM-120, BEZ235, PIK-90, and Duvelisib.

Alternate mTOR inhibitors include, for example, rapamycin, AZD8055, KU0063794, Torkinib (PP242), and Voxtalisib.

The present invention therefore provides multifunctional mTOR and/or MEK and/or PI3K inhibitors, as exemplified by the present compounds, for the treatment of diseases and conditions wherein inhibition of at least one, and preferably at least two, of mTOR, MEK, and PI3K has a beneficial effect. In one embodiment, the present invention relates to a method of treating an individual suffering from a disease or condition wherein inhibition of mTOR or MEK or PI3K, and preferably all, provides a benefit comprising administering a therapeutically effective amount of a present multifunctional compound to an individual in need thereof. It is envisioned that a present multifunctional compound exhibits a greater activity against KRAS mutant tumors than either an mTOR, MEK, or PI3K inhibitor monotherapy.

The method of the present invention can be accomplished by administering a present multifunctional compound as the neat compound or as a pharmaceutical composition. Administration of a pharmaceutical composition, or neat present multifunctional compound, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a present multifunctional compound and, optionally, a second therapeutic agent useful in the treatment of diseases and conditions wherein inhibition of mTOR and/or MEK and/or PI3K provides a benefit, packaged separately or together, and an insert having instructions for using these active agents.

In many embodiments, a present multifunctional compound is administered in conjunction with a second therapeutic agent useful in the treatment of a disease or condition wherein inhibition of one or more of mTOR, MEK, and PI3K provides a benefit. The second therapeutic agent is different from the present multifunctional compound. A present multifunctional compound and the second therapeutic agent can be administered simultaneously or sequentially to achieve the desired effect. In addition, the present multifunctional compound and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A present multifunctional compound and the second therapeutic agent can be administered together as a single-unit dose or separately as multi-unit doses, wherein the present multifunctional compound is administered before the second therapeutic agent or vice versa. One or more dose of the present multifunctional compound and/or one or more dose of the second therapeutic agent can be administered. The present multifunctional compounds therefore can be used in conjunction with one or more second therapeutic agents, for example, but not limited to, anticancer agents.

The diseases and conditions that can be treated in accordance to the invention include, for example, cancers. A variety of cancers can be treated including, but not limited to: carcinomas, including bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, renal, and skin (including squamous cell carcinoma); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma, hematopoietic tumors of myeloid lineage, including acute and chronic myelogenous leukemias, myelodysplastic syndrome, myeloid leukemia, and promyelocytic leukemia; tumors of the central and peripheral nervous system, including astrocytoma, neuroblastoma, glioma, and schwannomas; tumors of mesenchymal origin, including fibrosarcoma, rhabdomyoscarcoma, and osteosarcoma; and other tumors, including melanoma, xenoderma pigmentosum, keratoactanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

Additional forms of cancer treatable by the dual MEK/PI3K inhibitors of the present invention include, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, non-small cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, myelofibrosis, myeloid malignancy including acute myelogenous leukemia (AML), myelodysplastic syndrome (MDS), chronic myeloid leukemia (CML), and Kaposi's sarcoma.

The present multifunctional compounds are particularly useful in the treatment of pancreatic and colorectal cancers, and tumor metastatic disease Route of administration also can be by direct intraocular injection of the compounds for tumor treatments of the eye, for example including uveal melanoma and retinoblastoma. The present multifunctional inhibitors also can be delivered topically, orally, or intravenously, or by intraocular implant, to improve ocular drug bioavailability. As cell signaling pathways can have significant "cross-talk" and thus many different molecular interactions with other biological pathways, targeting the PI3K/Akt/mTOR and Raf/MEK/ERK pathways can be beneficial for eye diseases, including glaucoma, cataract, age-related macular degeneration, amblyopia, and diabetic retinopathy.

Additional diseases and conditions, including cancers, inflammatory diseases, allergic diseases, inflammatory bowel diseases, vasculitis, Behcet's syndrome, psoriasis, inflammatory dermatoses, asthma, respiratory allergic diseases, autoimmune diseases, graft rejection, fever, cardiovascular disorders, cerebrovascular disorders, fibrosis, connective tissue disease, sarcoidosis, genital and reproductive disorders, gastrointestinal disorders, neurologic disorders, sleep disorders, pain, renal disorders, and infectious diseases, including HIV, chronic pain including neuropathic pain (pain caused by damage to or malfunction of the nerves themselves) and nociceptive pain (nociceptors are receptors in the nervous system that activate during injury) and chronic pain associated with clinical diagnosis as for example, fibromyalgia, inflammation, musculoskeletal malfunction that can be treated by administration of a present mTOR and/or MEK and/or PI3K inhibitor are disclosed in U.S. Patent Publication No. 2011/0053907; U.S. Pat. No. 7,897,792; U.S. Patent Publication No. 2011/0009405, and U.S. Patent Publication No. 2010/0249099, each incorporated herein by reference in its entirety.

In the present method, a therapeutically effective amount of one or more of a present multifunctional inhibitor, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A present multifunctional compound can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a present multifunctional compound is administered in an effective amount to achieve its intended purpose. The exact formulation, route of administration, and dosage is determined by an individual physician in view of the diagnosed condition or disease. Dosage amount and interval can be adjusted individually to provide levels of a present multifunctional compound that is sufficient to maintain therapeutic effects.

Toxicity and therapeutic efficacy of the present multifunctional compounds can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g., inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a present multifunctional compound required for use in therapy varies with the nature of the condition being treated, the length of time that activity is desired, and the age and the condition of the patient, and ultimately is determined by the attendant physician. Dosage amounts and intervals can be adjusted individually to provide plasma levels of the multifunctional inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present multifunctional inhibitor can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A present multifunctional compound used in a method of the present invention can be administered in an amount of about 0.005 to about 500 milligrams per dose, about 0.05 to about 250 milligrams per dose, or about 0.5 to about 100 milligrams per dose. For example, a present multifunctional compound can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a present multifunctional inhibitor, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

In the treatment of a cancer, a present multifunctional compound can be administered with a chemotherapeutic agent and/or radiation.

Embodiments of the present invention employ electromagnetic radiation of: gamma-radiation ($10^{-20}$ to $10^{-13}$ m), X-ray radiation ($10^{-12}$ to $10^{-3}$ m), ultraviolet light (10 nm to 400 nm), visible light (400 nm to 700 nm), infrared radiation (700 nm to 1 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present multifunctional inhibitor, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

The chemotherapeutic agent can be any pharmacological agent or compound that induces apoptosis. The pharmacological agent or compound can be, for example, a small organic molecule, peptide, polypeptide, nucleic acid, or antibody. Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, a multifunctional inhibitor of the present invention can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct anti-neoplastic modalities." Additional chemotherapeutic agents useful in the invention include hormones and antagonists thereof, radioisotopes, antibodies, natural products, and combinations thereof.

Examples of chemotherapeutic agents useful in a method of the present invention are listed in the following table.

TABLE 1

Alkylating agents
Nitrogen mustards mechlorethamine
cyclophosphamide
ifosfamide
melphalan
chlorambucil
uracil mustard
temozolomide
Nitrosoureas carmustine (BCNU)
lomustine (CCNU)
semustine (methyl-CCNU)
chlormethine
streptozocin
Ethylenimine/Methyl-melamine triethylenemelamine (TEM)
triethylene thiophosphoramide
(thiotepa)
hexamethylmelamine
(HMM, altretamine)
Alkyl sulfonates busulfan
pipobroman
Triazines dacarbazine (DTIC)
Antimetabolites
Folic Acid analogs methotrexate
trimetrexate
pemetrexed
(Multi-targeted antifolate)
Pyrimidine analogs 5-fluorouracil
fluorodeoxyuridine
gemcitabine
cytosine arabinoside
(AraC, cytarabine)
5-azacytidine
2,2'-difluorodeoxy-cytidine
floxuridine
pentostatine
Purine analogs 6-mercaptopurine
6-thioguanine
azathioprine
2'-deoxycoformycin
(pentostatin)
erythrohydroxynonyl-adenine (EHNA)
fludarabine phosphate
2-chlorodeoxyadenosine
(cladribine, 2-CdA)
Type I Topoisomerase Inhibitors camptothecin
topotecan
irinotecan TABLE 1-continued Biological response modifiers G-CSF
GM-CSF
Differentiation Agents retinoic acid derivatives
Hormones and antagonists
Adrenocorticosteroids/antagonists prednisone and equivalents
dexamethasone
ainoglutethimide
Progestins hydroxyprogesterone caproate
medroxyprogesterone acetate
megestrol acetate
Estrogens diethylstilbestrol
ethynyl estradiol/equivalents
Antiestrogen tamoxifen
Androgens testosterone propionate
fluoxymesterone/equivalents
Antiandrogens flutamide
gonadotropin-releasing
hormone analogs
leuprolide
Natural products
Antimitotic drugs
Taxanes paclitaxel
Vinca alkaloids
vinblastine (VLB)
vincristine
vinorelbine
vindesine
Taxotere ® (docetaxel)
estramustine
estramustine phosphate
Epipodophylotoxins etoposide
teniposide
Antibiotics actimomycin D
daunomycin (rubidomycin)
doxorubicin (adriamycin)
mitoxantroneidarubicin
bleomycin
splicamycin (mithramycin)
mitromycin-C
dactinomycin
aphidicolin
epirubicin
idarubicin
daunorubicin
mithramycin
deoxy co-formycin
Enzymes L-asparaginase
L-arginase
Radiosensitizers metronidazole
misonidazole
desmethylmisonidazole
pimonidazole
etanidazole
nimorazole

TABLE 1-continued

RSU 1069
EO9
RB 6145
Nonsteroidal antiandrogens

SR4233
flutamide
nicotinamide
5-bromodeozyuridine
5-iododeoxyuridine
bromodeoxycytidine
Miscellaneous agents
Platinium coordination complexes cisplatin
carboplatin
oxaliplatin
anthracenedione
mitoxantrone
Substituted urea hydroxyurea
Methylhydrazine derivatives N-methylhydrazine (MIH)
procarbazine
Adrenocortical suppressant mitotane (o,p'-DDD)
ainoglutethimide
Cytokines interferon (α, β, γ)
interleukin-2
Photosensitizers hematoporphyrin derivatives
PHOTOFRIN®
benzoporphyrin derivatives
Npe6
tin etioporphyrin (SnET2)
pheoboride-a
bacteriochlorophyll-a
naphthalocyanines
phthalocyanines
zinc phthalocyanines
Radiation X-ray
ultraviolet light
gamma radiation
visible light
infrared radiation
microwave radiation Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicines (NSC 757), colchicines derivatives (e.g., NSC 33410), dolastatin 10 (NSC 376128), maytansine (NSC 153858), rhizoxin (NSC 332598), paclitaxel (NSC 125973), TAXOL® derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, eopthilone B, and discodermolide (see Service, (1996) Science, 274:2009) estramustine, nocodazole, MAP4, and the like. Examples of such agents are also described in Bulinski (1997) *J. Cell Sci.* 110:3055 3064; Panda (1997) *Proc. Natl. Acad. Sci. USA* 94:10560-10564; Muhlradt (1997) *Cancer Res.* 57:3344-3346; Nicolaou (1997) *Nature* 397:268-272; Vasquez (1997) *Mol. Biol. Cell.* 8:973-985; and Panda (1996) *J. Biol. Chem.* 271:29807-29812.

Cytostatic agents that may be used include, but are not limited to, hormones and steroids (including synthetic analogs): 17-α-ethinylestadiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminogluthimide, estramustine, medroxyprogesteroneacetate, leuprolide, flutamide, toremifene, zoladex.

Other cytostatic agents are antiangiogenics, such as matrix metalloproteinase inhibitors, and other VEGF inhibitors, such as anti-VEGF antibodies and small molecules such as ZD6474 and SU668. Anti-Her2 antibodies also may be utilized. An EGFR inhibitor is EKB-569 (an irreversible inhibitor). Also included are antibody C225 immunospecific for the EGFR and Src inhibitors.

Also suitable for use as a cytostatic agent is CASODEX® (bicalutamide, Astra Zeneca) which renders androgen-dependent carcinomas non-proliferative. Yet another example of a cytostatic agent is the antiestrogen TAMOXIFEN® which inhibits the proliferation or growth of estrogen dependent breast cancer. Inhibitors of the transduction of cellular proliferative signals are cytostatic agents. Representative examples include epidermal growth factor inhibitors, Her-2 inhibitors, PI3 inhibitors, Src kinase inhibitors, and PDGF inhibitors.

Compounds could also be administered in combination with opioids or cannabinoids, NSAIDS, steroids for chronic pain relief. Additional second therapeutic agents that can be administered with a present multifunctional inhibitor of the present invention are well known in the art, for example as disclosed in U.S. Patent Publication 2011/0053907; and U.S. Patent Publication No. 2011/0009405, and U.S. Patent Publication No. 2010/0249099, each incorporated herein by reference in its entirety.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of present multifunctional compounds.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the present multifunctional compound is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a present multifunctional compound. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present multifunctional compound.

When a therapeutically effective amount of a present multifunctional compound is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

The present multifunctional compounds can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding a present multifunctional inhibitor to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A present multifunctional inhibitor can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a present multifunctional inhibitor can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A present multifunctional inhibitor also can be formulated in rectal compositions, such as suppositories or retention enemas, e.g., containing conventional suppository bases. In addition to the formulations described previously, the present multifunctional inhibitor also can be formulated as a depot preparation. Such long-acting formulations can be administered by implantation (for example, subcutaneously or intramuscularly) or by intramuscular injection. Thus, for example, the present multifunctional inhibitors can be formulated with suitable polymeric or hydrophobic materials (for example, as an emulsion in an acceptable oil) or ion exchange resins.

In particular, the present multifunctional inhibitors can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The present multifunctional compounds also can be injected parenterally, for example, intravenously, intramuscularly, subcutaneously, or intracoronarily. For parenteral administration, the multifunctional inhibitors are best used in the form of a sterile aqueous solution which can contain other substances, for example, salts or monosaccharides, such as mannitol or glucose, to make the solution isotonic with blood. Compounds could also be administered using an inhaler as a spray to reach the lung tissue or by administration as a nasal spray.

A present multifunctional inhibitor and the second therapeutic agent can be administered together as a single-unit dose or separately as multi-unit doses, wherein the multifunctional inhibitor is administered before the second therapeutic agent or vice versa. It is envisioned that one or more dose of a present multifunctional inhibitor and/or one or more dose of a second therapeutic agent can be administered.

In one embodiment, a present multifunctional inhibitor and a second therapeutic agent are administered simultaneously. In related embodiments, a present multifunctional inhibitor and second therapeutic agent are administered from a single composition or from separate compositions. In a further embodiment, a present multifunctional inhibitor and second therapeutic agent are administered sequentially.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a present multifunctional compound and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

Prior mTOR, MEK, and PI3K inhibitors possessed properties that hindered their development as therapeutic agents. In accordance with an important feature of the invention, present multifunctional compounds were synthesized and evaluated as dual inhibitors for mTOR and/or MEK and/or PI3K. It is envisioned that the present multifunctional compounds are more efficacious and less toxic than a combination therapy using an MEK inhibitor, a PI3K inhibitor, and an mTOR inhibitor.

Synthesis of Compounds

The present compounds are a result of conjugating, or linking, an MEK inhibitor with an mTOR/PI3K inhibitor or a PI3K inhibitor to arrive at the multifunctional inhibitors of the present invention. Benzhydroxamate type MEK inhibitors are synthesized, for example, as disclosed in WO 2002/006213, incorporated herein by reference. SMK-17 type MEK inhibitors are synthesized, for example, as disclosed in WO 2004/083167, incorporated herein by reference. Triazine-based PI3K inhibitors are synthesized as disclosed in U.S. Patent Publication Nos. 2011/0053907, 2011/0009405, and 2010/0249099, each incorporated herein by reference in its entirety. mTOR inhibitors are synthesized as disclosed in A M Venketasan et al., *J. Med. Chem.* 53: 2636, 2010; N. Nishimur et al., *J. Med. Chem.* 54: 4735-51, 2011; and WO 2008/032162, each incorporated herein by reference.

Materials and Methods

Chemical syntheses involving air or moisture sensitive reagents and solvents were conducted under a positive pressure of nitrogen in oven-dried glassware. All other chemical reagents and anhydrous solvents were obtained from Aldrich Chemical Co., Milwaukee, Wis., and used without additional purification. Key compound intermediates 1,3,5-triazine analogs (2a, 2b) (7) and 3,4-difluoro-2-(2-fluoro-4-iodophenylamino)benzoic acid pentafluorophenyl ester (21) (compound 3) were synthesized as previously reported. 16,16-Dimethyl-15-oxo-3,6,9,12,14-pentaoxa-13-azaheptadecyl 4-methylbenzenesulfonate (t-Boc-aminoxy PEG4 tosylate) and 4-chlorobutane-1-sulfonyl chloride were purchased from Broadpharm, San Diego, Calif., and Enamine Ltd., Monmouth Jct., NJ, respectively. All other chemical reagents and anhydrous solvents were obtained from Aldrich Chemical Co., Milwaukee, Wis., and used without additional purification.

Column chromatography was performed on silica gel 60 (230-400 mesh ASTM) purchased from EMD Millipore, Billerica, Mass. Thin-layer chromatography (TLC) was performed using Analtech silica gel GF Uniplates (250 µm). TLC plates were visualized after development with ultraviolet (UV) light or by spraying with phosphomolybdic acid reagent with subsequent heating. $^1$H NMR spectra were recorded on Varian instruments at 400 and 700 MHz, respectively, in $CDCl_3$ or $CD_3OD$ as solvent with tetramethylsilane (TMS) as internal standard. Chemical shifts (δ) and coupling constants (J) are reported in parts per million (ppm) and in hertz (Hz), respectively. High resolution mass spectral analyses were performed using either a VG-70-250-S mass spectrometer for electron impact (EI) and chemical ionization (DCI) modes, a Waters Autospec Ultima instrument with an electrospray interface for electrospray ionization (ESI) mode, or a Waters Tofspec-2E run in reflectron mode. HPLC was performed using a Waters Breeze HPLC system (Waters Corporation, Milford, Mass.) equipped with a Waters 2487 dual wavelength absorbance detector. HPLC analysis was conducted at ambient temperature on a Waters XSELECT CSH C-18 column (4.6 mm×250 mm), 5 µm particle, with 0.1% TFA in $H_2O$ (A) and 0.1% TFA in $CH_3CN$ (B) solvent mixtures at a flow rate of 1 mL/min with UV absorbance monitored at 254 and 280 nm. HPLC runs were conducted using a 25 min solvent gradient of either 30% B to 90% B (method I), 60% B to 90% B (method II), or 10% B to 90% B (method III). All biologically tested compounds were demonstrated to have >95% chemical purity by reversed-phase gradient HPLC analysis.

| Abbreviations Used | |
|---|---|
| Akt | protein kinase B |
| MEK | allosteric mitogen-activated protein kinase |
| PI3K | phosphatidylinositol 3-kinase |
| mTor | mammalian target of rapamycin |
| br s | broad signal |
| cLogP | calculated log P |
| $CH_3CN$ | acetonitrile |
| DCM | dichloromethane |
| DMF | N,N-dimethylformamide |
| DIEA | N,N-diisopropylethylamine |
| DMSO | dimethylsulfoxide |
| $Et_3N$ | trimethylamine |
| HPBCD | (2-hydroxypropyl)-β-cyclodextrin |
| MEK | methyl ethyl ketone |
| rt | room temperature |
| TFA | trifluoroacetic acid |
| THF | tetrahydrofuran |
| $PdCl_2dPPf$ | [1,1'-bis(diphenylphosphino)ferrocene]palladium (II) dichloride |
| HAc | acetic acid |
| EDCI | 1-(3-dimethylaminopropyl)-3-ethylcarbodimide |
| HOBT | 1-hydroxybenzotriazole |
| $P(Ph)_3$ | triphenylphosphine |
| DEAD | diethyl azodicarboxylate |
| LHMDS | lithium hexamethyldisilazide |
| TBAF | tetra-n-butylammonium fluoride |
| PyBOP | (benzotriazol-1-yl-oxytripyrrolidinophosphonium hexafluorophosphate) |

The MEK and PI3K inhibitors can be conjugated using the non-limiting approaches set forth in Scheme 1 to Scheme 4.

Scheme 1$^a$

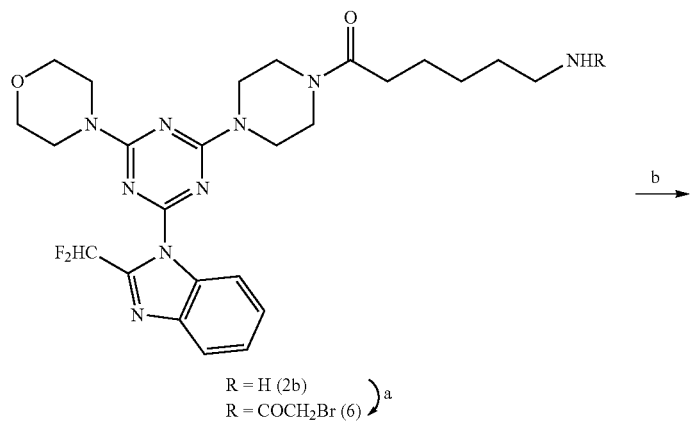

-continued
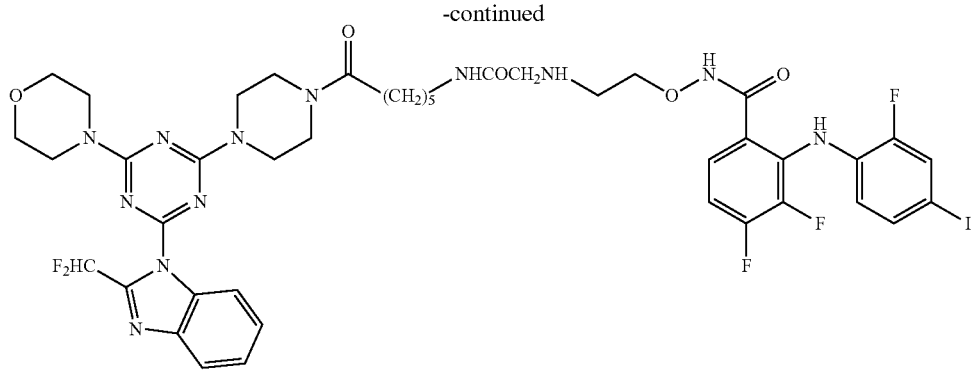
(7)
[a]Reagents and conditions: (a) BrCH$_2$COBr, Et$_3$N, CH$_2$Cl$_2$, 0° C. to rt, 3 h, 80%; (b) 5, NaI, K$_2$CO$_3$, DMF, rt, 4 h, 24%.

Scheme 2[a]
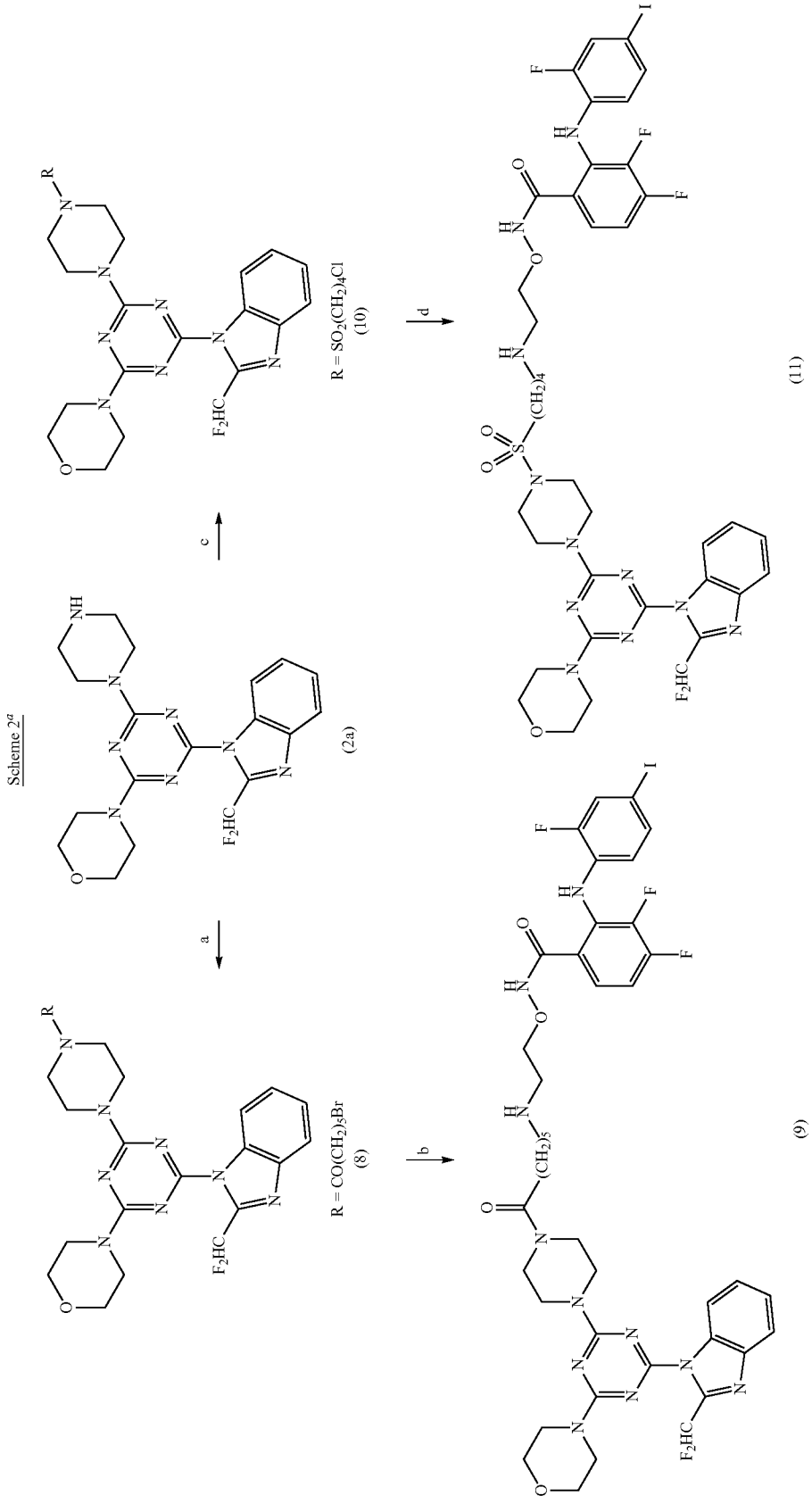
[a]Reagents and conditions: (a) Br(CH$_2$)$_5$COCl, K$_2$CO$_3$, MEK, 0° C. to rt, 3 h, 96%; (b) 5, NaI, K$_2$CO$_3$, CH$_3$CN, reflux, 4 h, 37%; (c) Cl(CH$_2$)$_4$SO$_2$Cl, Et$_3$N, CH$_2$Cl$_2$, 0° C. to rt, 18 h, 92%; (d) 5, NaI, K$_2$CO$_3$, CH$_3$CN, reflux, 18 h, 30%.

Scheme 3: Synthesis of 14 (ST-162)
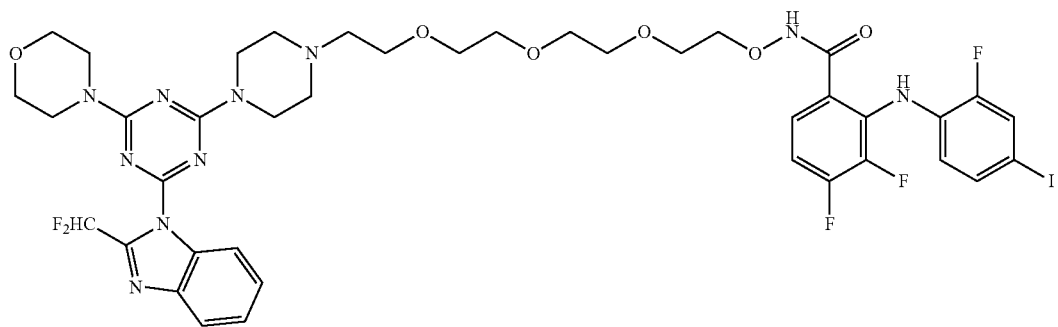
MEK1 IC$_{50}$: 0.015 nM
PI3K IC$_{50}$: 191 nm
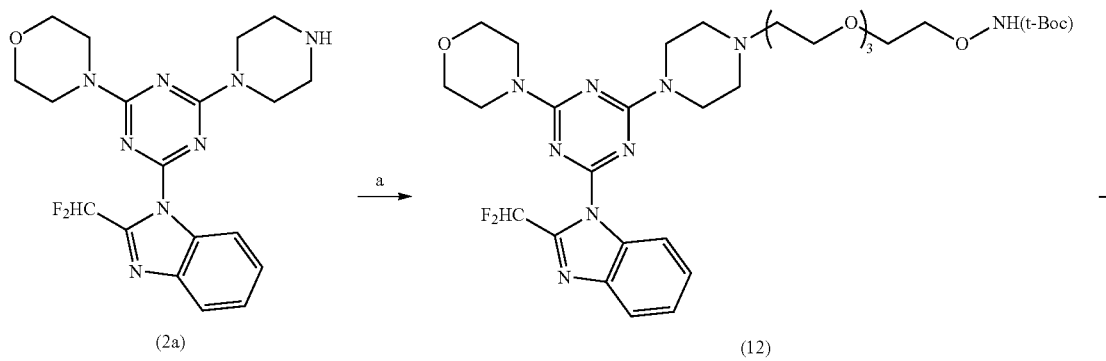
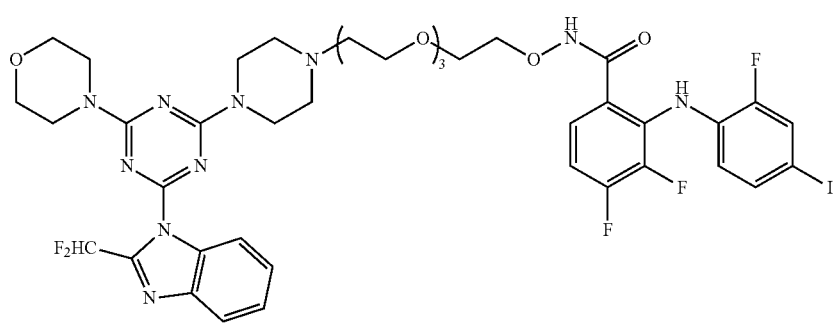
$^a$Reagents and conditions: (a) TosO—(CH$_2$CH$_2$O)$_4$NH(t-Boc), K$_2$CO$_3$, toluene, reflux, 24 h, 71%; (b) TFA, CH$_2$Cl$_2$, 0-5° C., 2 h, 82%; (c) 3, DIEA, DMF, rt, 18 h, 55%.

Synthetic Chemistry.

Key intermediates 2a, 2b, and 3 (FIG. 3) used in the preparation of the target bifunctional inhibitor compounds were synthesized as previously reported (7,21). MEK1 inhibitor 5 was synthesized by treatment of 3 with (2-aminoxyethyl)carbamic acid tert-butyl ester[22] in DMF in the presence of DIEA to give intermediate 4 followed by trifluoroacetic acid catalyzed cleavage of the Boc protecting group (FIG. 3). The synthesis of inhibitor derivative 7 was conducted as shown in Scheme 1. Initially, 2b was treated with bromoacetyl bromide in the presence of triethylamine to give the corresponding 2-bromoacetamide derivative 6 which was reacted with 5 to give inhibitor analog 7 in 18.5% overall yield. Inhibitor analogs 9 and 11 were obtained from the common piperazine substituted 1,3,5-triazine intermediate 2a as shown in Scheme 2. Triazine 2a was initially treated with 6-bromohexanoyl chloride in the presence of potassium carbonate to afford the corresponding 6-bromohexanamide analog 8 which provided inhibitor analog 9 in 37% yield following reaction with the MEK inhibitor 5 in refluxing acetonitrile. Inhibitor analog 11 was prepared from 2a in 27.5% overall yield by a similar approach via the 4-chlorobutanesulfonamide intermediate 10. Preparation of the pegylated linked bifunctional inhibitor 14 (ST-162) was carried out as shown in Scheme 3. Initially, piperazine substituted 1,3,5-triazine intermediate 2a was heated at reflux with the aminoxyprotected PEG4 tosylate derivative and potassium carbonate in toluene to give intermediate 12 followed by TFA catalyzed removal of the Boc group to give the aminoxy derivative 13. Subsequent reaction of 13 with the activated ester derivative 3 as described previously afforded 14 in 55% yield.

FIG. 3. Key intermediates used in synthesis of MEK/PI3K bifunctional inhibitors.

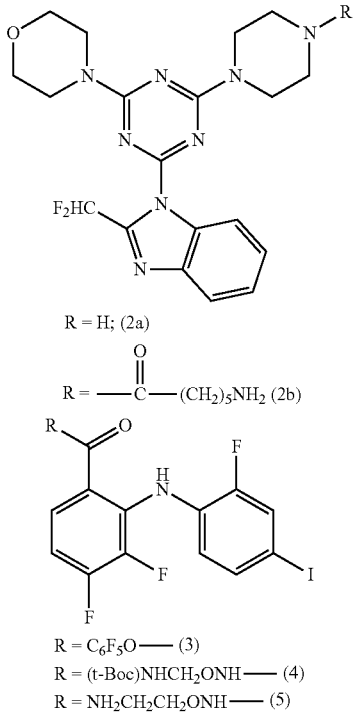

3,4-Difluoro-2-(2-fluoro-4-iodophenylamino)-N-{2-(tert-butoxycarbonylamino) ethoxy}benzamide (4)

A solution of (2-aminoxyethyl)carbamic acid tert-butyl ester[22] (0.945 g, 5.36 mmol) in DMF (6 mL) was added in portions to a solution of 3,4-difluoro-2-(2-fluoro-4-iodophenylamino)benzoic acid pentafluorophenyl ester[21] (3) (3.0 g, 5.36 mmol) in DMF (6 mL) followed by DIEA (1.38 g, 1.87 mL, 10.7 mmol) and stirred at rt for 18 h. The reaction mixture was concentrated to dryness under reduced pressure, diluted with EtOAc (100 mL), and extracted with brine ($2 \times 50$ mL), $H_2O$ (50 mL), dried ($MgSO_4$) and concentrated under reduced pressure. The crude material was purified by silica gel flash chromatography with a gradient of 30-55% EtOAc in hexanes to provide 2.77 g (94%) of the title compound 4 as a white foam. $^1H$ NMR ($CDCl_3$): δ 10.31 (br s, 1H), 8.59 (br s, 1H), 7.41-7.38 (m, 2H), 7.31 (d, 1H, J=8.5 Hz), 6.91-6.84 (m, 1H), 6.61-6.55 (m, 1H), 5.05 (br s, 1H), 3.93 (m, 2H), 3.43-3.39 (m, 2H), 1.45 (s, 9H). HRMS (ESI+): m/z calculated for $C_{20}H_{22}N_3F_3IO_4$ [M+H+], 552.0602. Found: 552.0594.

3,4-Difluoro-2-(2-fluoro-4-iodophenylamino)-N-(2-aminoethoxy)benzamide (5)

Trifluoroacetic acid (17.1 g, 11.5 mL, 150 mmol) was added to a cold solution (0-5° C.) of 4 (2.77 g, 5.0 mmol) in $CH_2OI_2$ (50 mL) under a nitrogen atmosphere and stirred at this temperature for 3 h. Upon completion of reaction, the mixture was diluted with $Et_2O$ (250 mL) and crushed ice (100 g). The pH of the aqueous solution was adjusted to pH 8 by slow addition of aqueous saturated $NaHCO_3$ and the organic layer separated, dried ($Na_2SO_4$), and concentrated under reduced pressure. The crude product was flash chromatographed on silica gel with a gradient of 5-30% $CH_3OH$ in $CH_2OI_2$ containing 1% $NH_4OH$ to give 1.72 g (76%) of the title compound 5 as a white solid. $^1H$ NMR ($CD_3OD$): δ 7.55-7.51 (m, 1H), 7.41 (dd, 1H, J=10.9, 1.9 Hz), 7.32 (dd, 1H, J=8.6, 1.0 Hz), 6.99-6.92 (m, 1H), 6.57-6.51 (m, 1H), 4.05 (t, 2H, J=5.0 Hz), 3.10 (t, 2H, J=5.0 Hz). HRMS (ESI+): m/z calculated for $C_{15}H_{14}N_3F_3IO_2$ [M+H+], 452.0077. Found: 452.0079. HPLC (method I): $t_R$=9.72 min.

2-(Difluoromethyl)-1-[4-(4-morpholinyl)-6-{4-(6-(Nbromoacetylamino) hexanoyl)}piperazino)-1,3,5-triazin-2-yl]-1H-benzimidazole (6)

A solution of the 1,3,5-triazine analog 2b (0.265 g, 0.50 mmol) and $Et_3N$ (0.102 g, 142 µL, 1.0 mmol) in $CH_2OI_2$ (3 mL) was cooled to 0° C. using an ice bath and treated dropwise under a nitrogen atmosphere with a solution of bromoacetyl bromide (0.122 g, 53 µL, 0.60 mmol) in $CH_2OI_2$ (2 mL). The ice bath was removed, and the reaction mixture was allowed to warm to rt and stirred for an additional 3 h. The mixture was diluted with EtOAC (100 mL), the organic layer washed with aqueous 1 N HCl (50 mL), aqueous saturated $NaHCO_3$, (50 mL), brine ($2 \times 50$ mL) and dried ($Na_2SO_4$). The crude product was purified by flash chromatography on silica gel with a gradient of 2-8% $CH_3OH$ in $CH_2OI_2$ to give 0.26 g (80%) of the title compound 6 as a beige amorphous solid. $^1H$ NMR ($CDCl_3$): δ 8.33 (d, 1H, J=8.0 Hz), 7.90 (d, 1H, J=8.0 Hz), 7.55 (t, 1H, J=53.5 Hz), 7.47-7.39 (m, 2H), 6.62 (br s, 1H), 3.88-3.74 (m, 16H), 3.60 (m, 2H), 3.35-3.30 (m, 2H), 2.42-2.39 (m, 2H), 1.75-1.68 (m, 2H), 1.62-1.57 (m, 2H), 1.46-1.38 (m, 2H).

N-(2-((2-(((6-(4-(4-(2-(Difluoromethyl)-1H-benzo[d]imidazol-1-yl)-6-morpholino-1,3,5-triazin-2-yl)piperazin-1-yl)-6-oxohexyl)amino)-2-oxoethyl)amino)ethoxy)-3,4-difluoro-2-((2-fluoro-4-iodophenyl)amino)benzamide (Compound 7)

A solution of the benzhydroxamate analog 5 (0.18 g, 0.40 mmol), anhydrous $K_2CO_3$ (0.061 g, 0.44 mmol), and sodium iodide (0.066 g, 0.44 mmol) in DMF (3 mL) was treated dropwise with a solution of 6 (0.26 g, 0.40 mmol) in DMF (2 mL) and stirred at rt for 18 h. The mixture was diluted with EtOAC (50 mL), the organic layer washed with brine (2×25 mL) and dried ($Na_2SO_4$). The crude product was purified by flash chromatography on silica gel with a gradient of 5-20% $CH_3OH$ in $CH_2OI_2$ containing 1% $NH_4OH$ to give 0.098 g (24%) of the title compound 7 as a cream amorphous solid. $^1$H NMR ($CDCl_3$+1 drop of $CD_3OD$): δ 8.33 (d, 1H, J=7.9 Hz), 7.88 (d, 1H, J=7.8 Hz), 7.55 (t, 1H, J=53.5 Hz), 7.47-7.40 (m, 3H), 7.35-7.25 (m, 2H), 6.79-6.76 (m, 1H), 6.52-6.50 (m, 1H), 4.09 (m, 2H), 3.90-3.71 (m, 16H), 3.58 (m, 2H), 3.34 (s, 2H), 3.20 (m, 2H), 2.93 (m, 2H), 2.37-2.16 (m, 4H), 1.61 (m, 2H), 1.49 (m, 2H), 1.33-1.26 (m, 2H). HRMS (ESI+): m/z calculated for $C_{42}H_{47}N_{12}F_5O_5$ [M+H+], 1021.2752 Found: 1021.2754. HPLC (method I): $t_R$=15.34 min (95.3% chemical purity).

2-(Difluoromethyl)-1-[4-(4-morpholinyl)-6-{4-(6-bromohexanoyl)}piperazino)-1,3,5-triazin-2-yl]-1H-benzimidazole (8)

A stirred suspension of the 1,3,5-triazine analog 2a (0.208 g, 0.5 mmol) and anhydrous $K_2CO_3$ (0.208 g, 1.5 mmol) in methyl ethyl ketone (3.5 mL) was cooled to 0-5° C. using an ice bath and treated dropwise under a nitrogen atmosphere with a solution of 6-bromohexanoyl chloride (0.112 g, 81 μL, 0.525 mmol) in MEK (1.5 mL). The ice bath was removed, and the reaction mixture was stirred at rt for an additional 3 h. The residue obtained after concentration under reduced pressure was partitioned between aqueous saturated $NaHCO_3$ (100 mL) and EtOAC (100 mL). The organic layer was removed, washed successively with brine (50 mL), $H_2O$ (50 mL) and dried ($Na_2SO_4$). The crude product was purified by flash chromatography on silica gel with a gradient of 3-10% acetone in $CH_2OI_2$ to give 0.28 g (96%) of the title compound 8 as a colorless oil. $^1$H NMR ($CDCl_3$): δ 8.33 (d, 1H, J=7.8 Hz), 7.90 (d, 1H, J=7.8 Hz), 7.55 (t, 1H, J=53.5 Hz), 7.47-7.39 (m, 2H), 3.89-3.60 (m, 16H), 3.44 (t, 2H, J=6.6 Hz), 2.41 (m, 2H), 1.95-1.88 (m, 2H), 1.76-1.68 (m, 2H), 1.57-1.49 (m, 2H). HRMS (ESI+): m/z calculated for $C_{25}H_{32}N_8BrF_2O_2$ [M+H+], 593.1794. Found: 593.1795. HPLC (method I): $t_R$=20.38 min.

N-(2-((6-(4-(4-(2-(Difluoromethyl)-1H-benzo[d]imidazol-1-yl)-6-morpholino-1,3,5-triazin-2-yl)piperazin-1-yl)-6-oxohexyl)amino)ethoxy)-3,4-difluoro-2-((2-fluoro-4-iodophenyl)amino)benzamide (Compound 9)

A mixture of 8 (0.158 g, 0.27 mmol), benzhydroxamate analog 5 (0.24 g, 0.53 mmol), anhydrous $K_2CO_3$ (0.042 g, 0.30 mmol), and NaI (0.045 g, 0.30 mmol) in $CH_3CN$ (5 mL) was stirred at reflux for 4 h. The reaction mixture was diluted with EtOAc (100 mL), extracted with brine (100 mL), and dried ($Na_2SO_4$). The crude product was purified by flash chromatography on silica gel with a gradient of 3-20% $CH_3OH$ in $CH_2OI_2$ containing 1% $NH_4OH$ to give 0.096 g (37%) of the title compound 9 as a white amorphous powder. $^1$H NMR ($CDCl_3$): δ 8.32 (d, 1H, J=7.6 Hz), 7.90 (d, 1H, J=8.4 Hz), 7.63 (m, 1H), 7.54 (t, 1H, J=53.5 Hz), 7.46-7.38 (m, 2H), 7.33-7.25 (m, 2H), 6.78 (m, 1H), 6.51 (m, 1H), 4.27 (m, 2H), 3.88-3.41 (m, 16H), 3.14 (m, 2H), 2.88 (m, 2H), 2.24 (m, 2H), 1.66 (m, 2H), 1.54 (m, 2H), 1.31 (m, 2H). HRMS (ESI+): m/z calculated for $C_{40}H_{44}N_{11}F_5O_4$ [M+H+], 964.2537. Found: 964.2550. HPLC (method I): $t_R$=15.71 min (96.7% chemical purity).

2-(Difluoromethyl)-1-[4-(4-morpholinyl)-6-{4-(4-chlorobutane-1-sulfonyl)}piperazino)-1,3,5-triazin-2-yl]-1H-benzimidazole (10)

A solution of the 1,3,5-triazine analog 2a (0.208 g, 0.5 mmol) and $Et_3N$ (0.061 g, 84 μL, 0.6 mmol) in $CH_2OI_2$ (5 mL) was cooled to 0-5° C. under a nitrogen atmosphere using an ice bath. A solution of 4-chlorobutane-1-sulfonyl chloride (0.096 g, 70 μL, 0.5 mmol) in $CH_2OI_2$ (2 mL) was added dropwise, the ice bath was removed, and the reaction mixture was stirred at rt for 18 h. The reaction mixture was treated with $CH_2OI_2$ (50 mL) and washed successively with brine (2×50 mL), $H_2O$ (50 mL) and dried ($Na_2SO_4$). The crude product was purified by flash chromatography on silica gel with a gradient of 1-5% $CH_3OH$ in $CH_2OI_2$ containing 1% $NH_4OH$ to give 0.264 g (92%) of the title compound 10 as a white foam. $^1$H NMR ($CDCl_3$): δ 8.31 (d, 1H, J=7.6 Hz), 7.90 (d, 1H, J=8.2 Hz), 7.53 (t, 1H, J=53.3 Hz), 7.47-7.39 (m, 2H), 4.00 (m, 4H), 3.89 (m, 4H), 3.80 (m, 4H), 3.58 (t, 2H, J=6.0 Hz), 3.40 (m, 4H), 3.00-2.96 (m, 2H), 2.05-1.93 (overlapping m, 4H). HRMS (ESI+): m/z calculated for $O_{23}H_{30}N_8ClF_2O_3S$ [M+H+], 571.1812. Found: 571.1812.

N-(2-((4-((4-(4-(2-(Difluoromethyl)-1H-benzo[d]imidazol-1-yl)-6-morpholino-1,3,5-triazin-2-yl))piperazin-1-yl)sulfonyl)-butyl)amino)ethoxy)-3,4-difluoro-2-((2-fluoro-4-iodophenyl)-amino)benzamide (Compound 11)

A mixture of the 4-chlorobutylsulfonamide analog 10 (0.156 g, 0.273 mmol), benzhydroxamate analog 5 (0.248 g, 0.55 mmol), anhydrous $K_2CO_3$ (0.042 g, 0.30 mmol), and NaI (0.045 g, 0.30 mmol) in $CH_3CN$ (5 mL) was stirred at reflux for 18 h. The mixture was diluted with $CHCl_3$ (100 mL), extracted with brine (2×50 mL), and dried ($Na_2SO_4$). The crude product was purified by flash chromatography on silica gel with a gradient of 5-15% $CH_3OH$ in $CH_2OI_2$ containing 1% $NH_4OH$ to give 0.080 g (30%) of the title compound 11 as a white amorphous powder. $^1$H NMR ($CDCl_3$+1 drop of $CD_3OD$): δ 8.30 (d, 1H, J=7.6 Hz), 7.89 (d, 1H, J=7.4 Hz), 7.53 (t, 1H, J=53.3 Hz), 7.47-7.26 (m, 5H), 6.81-6.79 (m, 1H), 6.52-6.51 (m, 1H), 4.15 (m, 2H), 3.96-3.79 (m, 12H), 3.32 (m, 4H), 3.00 (m, 2H), 2.88 (m, 2H), 2.77 (m, 2H), 1.86 (m, 2H), 1.72 (m, 2H). HRMS (ESI+): m/z calculated for $O_{38}H_{42}N_{11}F_5O_5S$ [M+H+], 986.2050. Found: 986.2043. HPLC (method III): $t_R$=20.09 min (97.9% chemical purity).

2-(Difluoromethyl)-1-[4-(4-morpholinyl)-6-{4-(2-(2-(2-(2-(tert-butylcarbonylaminoxy)ethoxy)ethoxy)ethoxy)ethyl}-piperazino)-1,3,5-triazin-2-yl]-1H-benzimidazole (12)

A mixture of the 1,3,5-triazine analog 2a (0.52 g, 1.25 mmol), t-Boc-aminoxy PEG4 tosylate (0.58 g, 1.25 mmol), and anhydrous K$_2$CO$_3$ (0.345 g, 2.5 mmol) in toluene (8 mL) was stirred at reflux for 24 h. The mixture was diluted with CH$_2$OI$_2$ (100 mL), extracted with brine (100 mL), H$_2$O (100 mL), and dried (Na$_2$SO$_4$). The crude product was purified by flash chromatography on silica gel with a gradient of 2-5% CH$_3$OH in CHCl$_3$ containing 1% NH$_4$OH to give 0.63 g (71%) of the title compound 12 as a pale yellow viscous gum. $^1$H NMR (CDCl$_3$): δ 8.34 (d, 1H, J=7.8 Hz), 7.99 (s, 1H), 7.88 (d, 1H, J=7.8 Hz), 7.58 (t, 1H, J=53.5 Hz), 7.43-7.37 (m, 2H), 4.03-4.01 (m, 2H), 3.91-3.86 (m, 8H), 3.80-3.78 (m, 4H), 3.73-3.63 (m, 12H), 2.66 (t, 2H, J=5.6 Hz), 2.61 (m, 4H), 1.47-1.48 (m, 9H). HRMS (ESI+): m/z calculated for C$_{32}$H$_{48}$N$_9$F$_2$O$_7$: 708.3639. Found: 708.3636. HPLC (method I): t$_R$=9.76 min.

2-(Difluoromethyl)-1-[4-(4-morpholinyl)-6-{4-(2-(2-(2-(2-aminoxy)ethoxy)ethoxy)ethoxy)ethyl}piperazino)-1,3,5-triazin-2-yl]-1H-benzimidazole (13)

A stirred solution of 12 (0.255 g, 0.36 mmol) in CH$_2$OI$_2$ (5 mL) was cooled to 0° C. with an ice bath and treated dropwise with a solution of TFA (2.5 mL) in CH$_2$OI$_2$ (5 mL). The reaction was stirred at 0-5° C. for an additional 2 h, then treated with ice-cold water (100 mL), and the pH of the aqueous layer was adjusted to pH 8 with saturated aqueous NaHCO$_3$. The mixture was extracted twice with EtOAc (100 mL) and the organic extract washed successively with brine (100 mL), H$_2$O (100 mL) and dried (Na$_2$SO$_4$). The crude product was purified by flash chromatography on silica gel with a gradient of 2-4% CH$_3$OH in CH$_2$OI$_2$ containing 1% NH$_4$OH to give 0.18 g (82%) of the title compound 13 as a colorless viscous oil. $^1$H NMR (CDCl$_3$): δ 8.34 (d, 1H, J=7.8 Hz), 7.89 (d, 1H, J=8.0 Hz), 7.58 (t, 1H, J=53.5 Hz), 7.45-7.37 (m, 2H), 5.52 (br s, 2H), 3.89-3.69 (m, 14H), 3.67 (m, 12H), 2.66 (t, 2H, J=5.5 Hz), 2.60 (m, 4H). HRMS (ESI+): m/z calculated for C$_{27}$H$_{40}$N$_3$F2O$_5$ [M+H+], 608.3115. Found: 608.3114. HPLC (method III): t$_R$=10.75 min.

N-(2-(2-(2-(2-(4-(4-(2-(Difluoromethyl)-1H-benzo[d]imidazol-1-yl)-6-morpholino-1,3,5-triazin-2-yl))piperazin-1-yl)ethoxy)-ethoxy)ethoxy)ethoxy)-3,4-difluoro-2-((2-fluoro-4-iodophenyl)amino)benzamide (ST-162; 14)

A mixture of 13 (0.10 g, 1.64 mmol), pentafluorophenyl ester analog 3 (0.092 g, 1.64 mmol), and DIEA (0.042 g 0.58 µL, 0.33 mmol) in DMF (1 mL) was stirred at rt for 24 h. The mixture was diluted with CH$_2$OI$_2$ (100 mL), extracted with brine (2×100 mL), and dried (Na$_2$SO$_4$). The crude product was purified by flash chromatography on silica gel with a gradient of 2-5% CH$_3$OH in CHCl$_3$ containing 1% NH$_4$OH to give 0.088 g (55%) of the title compound 14 as a pale pink crystalline solid. $^1$H NMR (CDCl$_3$+1 drop of CD$_3$OD): δ 8.33 (dd, 1H, J=7.8, 1.4 Hz), 7.86 (dd, 1H, J=7.0, 1.5 Hz), 7.58 (t, 1H, J=53.6 Hz), 7.46-7.26 (m, 5H), 6.86-6.79 (m, 1H), 6.58-6.52 (m, 1H), 4.13-4.11 (m, 2H), 3.87-3.74 (m, 14H), 3.67-3.60 (m, 10H), 2.86 (br s, 1H), 2.64 (t, 2H, J=5.5 Hz), 2.59-2.52 (m, 4H). HRMS (ESI+): m/z calculated for C$_{40}$H$_{45}$N$_{10}$F$_5$1O$_6$ [M+H+], 983.2483. Found: 983.2477. HPLC (method I): t$_R$=14.56 min.

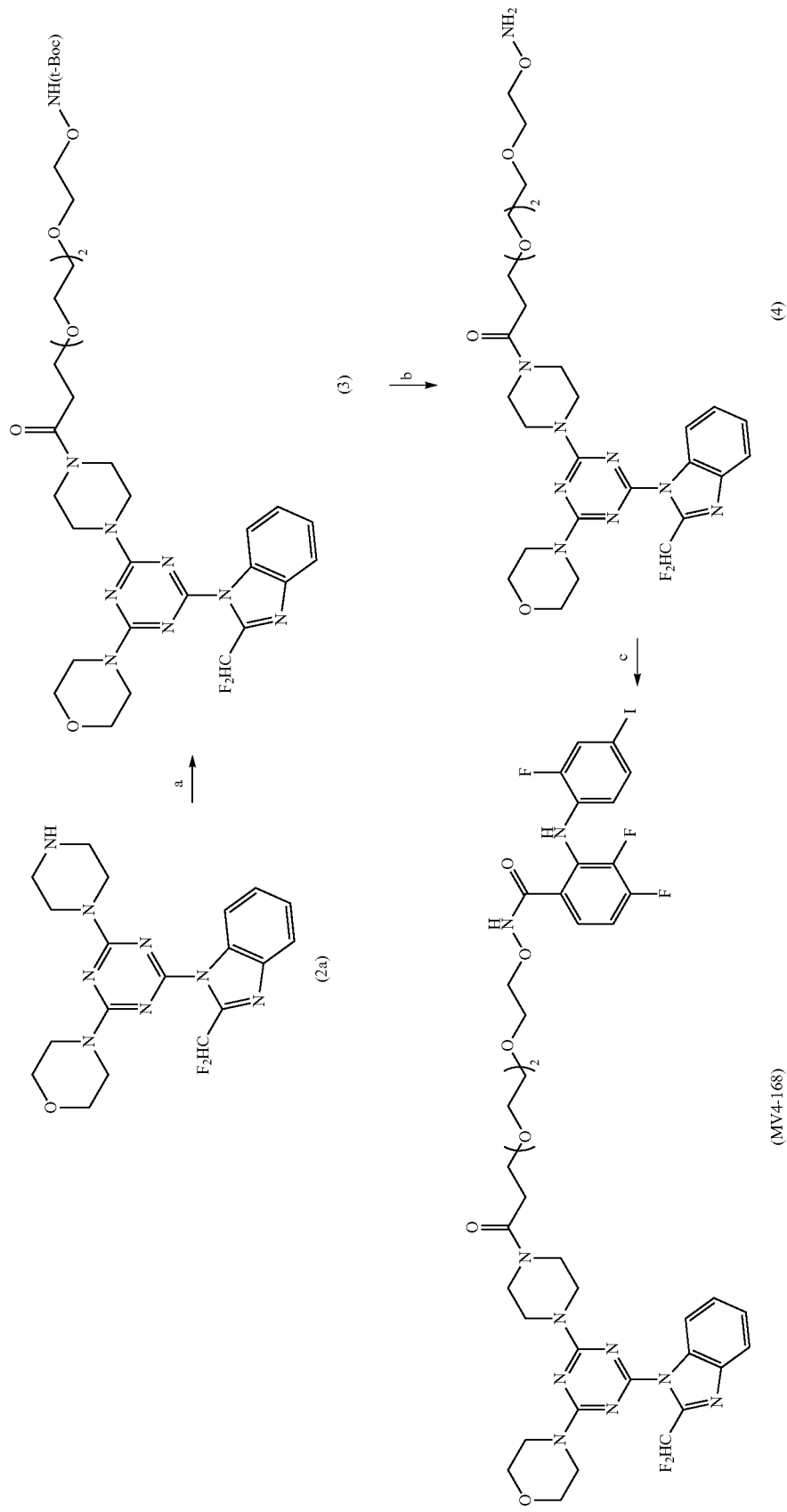
Scheme 4 Synthesis of MV4-168 (ST-168)
Reagents and conditions: (a) (t-Boc)NHO—(CH$_2$CH$_2$O)$_3$CH$_2$CH$_2$COOH, PyBoP, DIEA, THF:DCM, 4 h, 73%; (b) TFA, DCM, 0-5° C., 2 h, 82%; (c) 2, DIEA, PyBop, THF:DCM, 18 h, 54%.
Note: The synthesis of compound intermediate 2 is reported in WO2002/006213A2.

Experimental Details for Synthesis of MV4-168 (ST-168)

Compound intermediates 1,3,5-triazine analog (2a) (2) and 3,4-difluoro-2-(2-fluoro-4-iodophenylamino)-benzoic acid (2) (3) were synthesized as previously reported. 2,2-dimethyl-4-oxo-3,6,9,12,15-pentaoxa-5-azaoctadecan-18-oic acid (t-Boc-aminoxy-PEG3-acid) was purchased from Broadpharm, San Diego, Calif. All biologically tested compounds were demonstrated to have >98% chemical purity by reversed-phase gradient HPLC analysis.

tert-butyl 2-(2-(2-(3-(4-(4-(2-(difluoromethyl)-1H-benzo[d]imidazol-1-yl)-6-morpholino-1,3,5-triazin-2-yl))piperazine-1-yl)-3-oxopropoxy)ethoxy)ethoxy)ethoxycarbamate (3)

A solution of the t-Boc-aminoxy PEGS acid analog (170 mg, 0.50 mmol) in 12 mL of THF:DCM (1:1) was treated with 1,3,5-triazine analog 2a (208 mg, 0.50 mmol), DIEA (142 mg, 192 µL, 1.1 mmol), and PyBop (261 mg, 0.50 mmol) and stirred at room temperature (rt) for 4 h. HPLC analysis (Method 1) and TLC analysis (Analtech silica plates; DCM:CH$_3$OH:NH$_4$OH (95:5:1)) showed completion of reaction at this point. The mixture was concentrated under reduced pressure, diluted with DCM (50 mL) extracted with brine (25 mL), H$_2$O (25 mL) and dried (Na$_2$SO$_4$). The crude product was purified by flash chromatography on silica gel with a gradient of 1%-4% CH$_3$OH in DCM containing 1% NH$_4$OH to give 269 mg (73%) of the title compound 3 as a viscous oil. $^1$H NMR (CDCl$_3$): δ 8.33 (d, 1H, J=7.8 Hz), 7.90 (d, 1H, J=8.0 Hz), 7.72 (br s, 1H), 7.56 (t, 1H, J=53.6 Hz), 7.47-7.39 (m, 2H), 4.00-3.65 (m, 30H), 2.71 (t, 2H, J=6.5 Hz), 1.47 (s, 9H). HRMS (ESI+): m/z calculated for C$_{33}$H$_{48}$N$_9$F$_2$O$_8$[M+H±]: 736.3588. Found: 736.3588; calculated for [M+Na$^+$]: 758.3408. Found: 758.3407 (100%). HPLC (Method I): t$_R$=15.8 min.

3-(2-(2-(2-(aminooxy)ethoxy)ethoxy)ethoxy)-1-(4-(4-(2-(difluoromethyl)-1H-benzo[d]imidazol-1-yl)-6-morpholino-1,3,5-triazin-2-yl)piperazin-1-yl)propan-1-one (4)

A stirred solution of 3 (0.184 g, 0.25 mmol) in DCM (4 mL) was cooled to 0° C. with an ice bath and treated with a solution of TFA (2 mL) in DCM (2 mL). The reaction was stirred at 0-5° C. for an additional 2 h, then treated with ice-cold water (25 mL), and the pH of the aqueous layer was adjusted to pH 8 with saturated aqueous solution of NaHCO$_3$. The mixture was extracted twice with EtOAc (25 mL), and the organic extracts washed successively with brine and H$_2$O, then dried (Na$_2$SO$_4$). Concentration under reduced pressure afforded the product 4 (130 mg; 82%) as a pale-yellow oil which was used directly in the following step. $^1$H NMR (CDCl$_3$): δ 8.33 (d, 1H, J=7.8 Hz), 7.90 (d, 1H, J=8.4 Hz), 7.56 (t, 1H, J=53.6 Hz), 7.47-7.39 (m, 2H), 3.52 (br s, 1H), 3.93-3.65 (m, 30H), 2.70 (t, 2H, J=6.4 Hz), 1.68 (br s, 2H). HRMS (ESI+): m/z calculated for C$_{28}$H$_{40}$N$_9$F$_2$O$_6$[M+1-1±]: 636.3064. Found: 636.3068 (100%). calculated for [M+Na$^+$]: 658.2884. Found: 658.2885. HPLC (Method I): t$_R$=7.7 min.

N-(2-(2-(2-(3-(4-(4-(2-(difluoromethyl)-1H-benzo[d]imidazol-1-yl)-6-morpholino-1,3,5-triazin-2-yl))piperazin-1-yl)-3-oxopropoxy)ethoxy)ethoxy)ethoxy)-3,4-difluoro-2-((2-fluoro-4-iodophenyl)amino)benzamide (ST-168)

A mixture of 4 (127 mg, 0.20 mmol), 3,4-difluoro-2-(2-fluoro-4-iodophenylamino)-benzoic acid 2 (79 mg, 0.20 mmol), and DIEA (57 mg, 77 µL, 0.44 mmol) in a mixture of 4 mL of THF:DCM (1:1) was treated with PyBop (105 mg, 0.20 mmol) and stirred at rt for 18 h. HPLC analysis (Method 1) and TLC analysis (Analtech silica; DCM: CH$_3$OH:NH$_4$OH; 95:5:1; Rf of product ST-168=0.20) showed completion of reaction. The mixture was concentrated under reduced pressure, the residue dissolved in EtOAc (50 mL), washed with aqueous 0.1N HCl, saturated aqueous NaHCO$_3$, brine and dried (Na$_2$SO$_4$). The crude product was purified by flash chromatography on silica gel with a gradient of 1%-6% CH$_3$OH in DCM containing 1% NH$_4$OH to give 110 mg (54%) of the title compound as a white amorphous solid. $^1$H NMR (CDCl$_3$): δ 8.90 (br s, 1H), 8.32 (d, 1H, J=7.8 Hz), 7.88 (d, 1H, J=7.6 Hz), 7.55 (t, 1H, J=53.5 Hz), 7.44-7.28 (m, 5H), 6.83-6.77 (m, 1H), 6.58-6.52 (m, 1H), 4.13 (m, 2H), 3.88-3.50 (m, 28H), 2.62 (m, 2H), 1.89 (br s, 2H). HRMS (ESI+): m/z calculated for O$_{41}$H$_{45}$N$_{10}$F$_5$IO$_7$ [M+H$^+$]: 1011.2432. Found: 1011.2431. calculated for [M+Na$^+$]: 1033.2251. Found: 1033.2247 (100%). HPLC (Method II): t$_R$=17.7 min.

HPLC Analysis Method I.

HPLC analysis was conducted at ambient temperature on a Waters XSELECT CSH C-18 column (4.6×250 mm), 5µ particle, with 0.1% TFA in H$_2$O (A) and 0.1% TFA in CH$_3$CN (B) solvent mixtures at a flow rate of 1 mL/min. Analysis was performed with a solvent gradient from 30% B (initial) to 90% B over a 25 min run time with UV absorbance monitoring at 254 and 280 nm.

HPLC Analysis Method II:

HPLC analysis was performed as above with a solvent gradient from 50% B (initial) to 90% B over a 25 min run time.

Biological Data

The synthesis of a series of single entity, bifunctional MEK1/PI3K inhibitors achieved by covalent linking of structural analogs of the ATP-competitive PI3K inhibitor ZSTK474 and the ATP-noncompetitive MEK inhibitor PD0325901 is described. The biofunctional inhibitors displayed potent in vitro inhibition of MEK1 (0.015<I0$_{50}$ (nM)<500) and PI3K (54<IC$_{50}$ (nM)<341) in enzymatic inhibition assays. Concurrent MEK1 and PI3K inhibition was demonstrated with compound 14 in two tumor cell lines (A549, D54). Inhibitors produced dose-dependent decreased cell viability similar to the combined administration of equivalent doses of ZSTK474 and PD0325901. In vivo efficacy of compound 14 following oral administration was demonstrated in D54 glioma and A549 lung tumor bearing mice. Compound 14 showed a 95% and 67% inhibition of tumor ERK1/2 and Akt phosphorylation, respectively, at 2 h postadministration by Western blot analysis, confirming the bioavailability and efficacy of this bifunctional inhibitor strategy toward combined MEK1/PI3K inhibition.

Figure 4A:
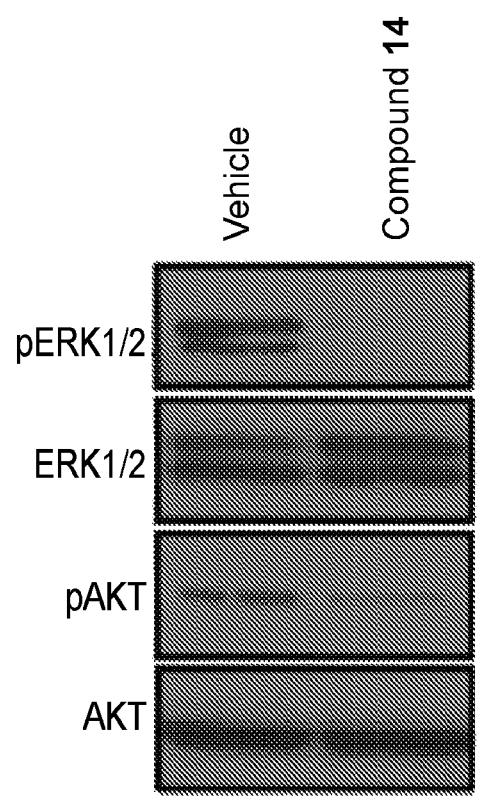
FIG. 4 shows the in vitro MEK1 and PI3K inhibition activity in tumors bearing mice by compound 14.
Figure 4B:
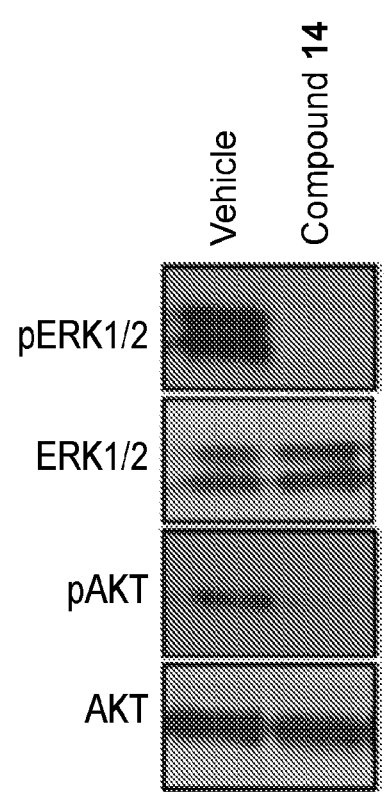

Virtual Docking of Compound 14 at MEK1 and PI3K Binding Pockets. ST-162 is predicted to retain many of the binding interactions displayed by the potent MEK1 inhibitor PD318088 within the MEK1 allosteric binding region including key interactions of both hydroxamate oxygens with Lys97, the 4-fluorine atom on the A ring with the backbone NHs of Val211 and Ser212, and the iodine containing B-ring within the hydrophobic pocket (FIG. 4A). Similarly, ST-162 is also predicted to serve as a PI3K inhibitor, as it retains the hydrogen bonding interaction of the morpholine group oxygen with the valine backbone amide NH group (Val828) and the imidazole nitrogen interaction with the Lys779 side chain amine group (FIG. 4B).

Synthesis of Fatty Acid Ester Analog of PD0316684

Compounds 4 and 9 in the below schemes are known in the literature and are synthesized reported in Nishimura, N. et al. *J. Med Chem.* 54, 4735-4751, 2011.

Compound intermediate 25 in the below schemes is synthesized using the general procedures reported in Venkatesan, A M. et al. *J. Med Chem.* 53, 2636-2645, 2010.

Step 1

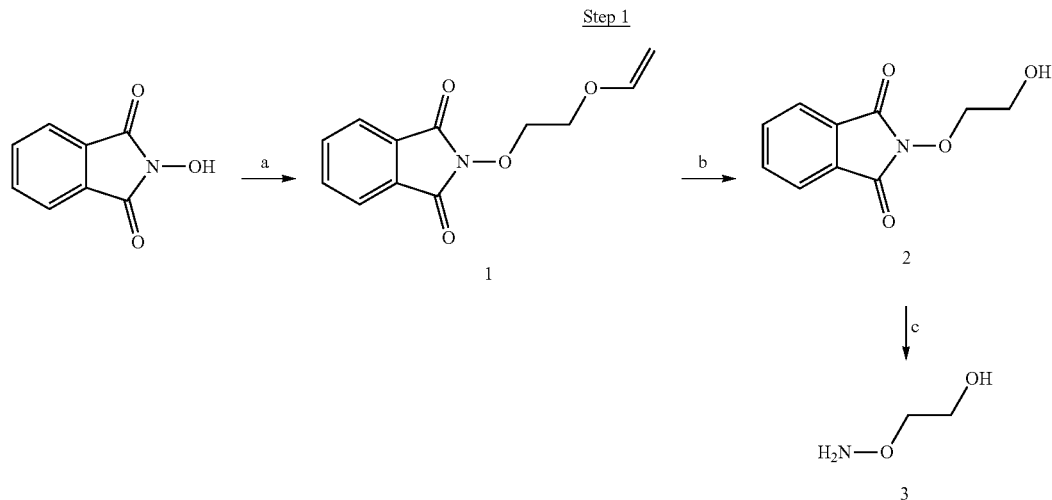

Reagents and conditions: (a) ethylene glycol vinyl ether, P(Ph)₃, DEAD, THF, 0° C.; (b) 0.3N HCl, Dioxane, rt; (c) CH₃NH₂NH₂, DCM.

Step 2

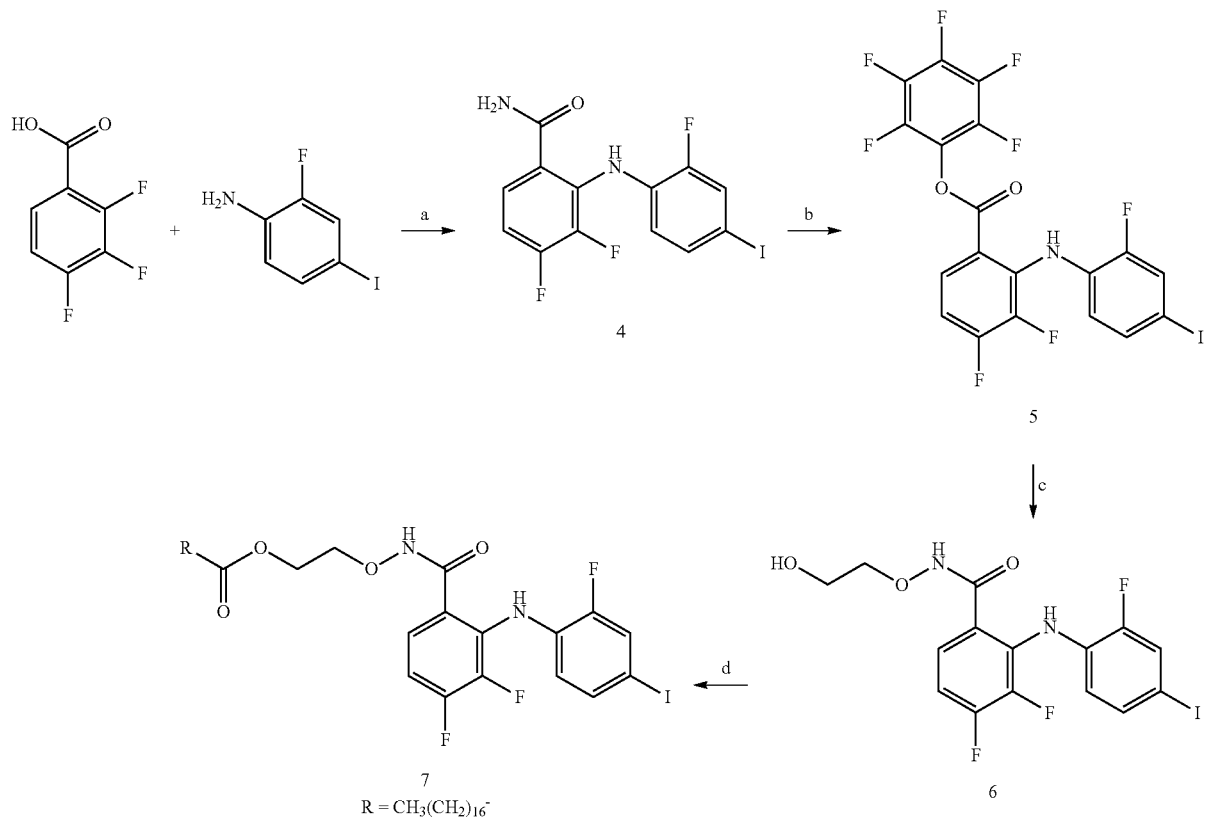

R = CH₃(CH₂)₁₆⁻

Reagents and conditions: (a) LHMDS, THF, -65° C.; (b) pentafluorophenyl trifluoroacetate, pyridine, DMF; (c) 3, DIEA, DMF, rt; (d) acid chloride, Et₃N, DMF.

Synthesis of ST-181
Step 1
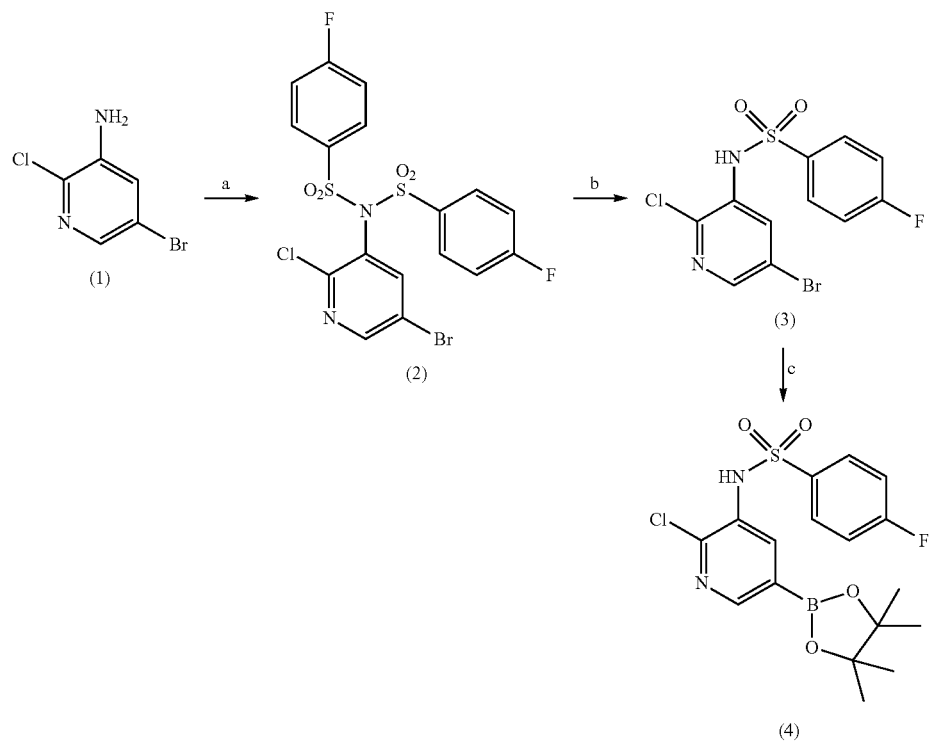
Reagents and conditions:
(a) 4-fluorophenylsulfonyl chloride, pyridine, 100° C.;
(b) $K_2CO_3$, $CH_3OH$, $H_2O$, rt;
(c) bis(pinacolato)diborane, KOAc, $PdCl_2dppf$, dioxane, 120° C.
Step 2
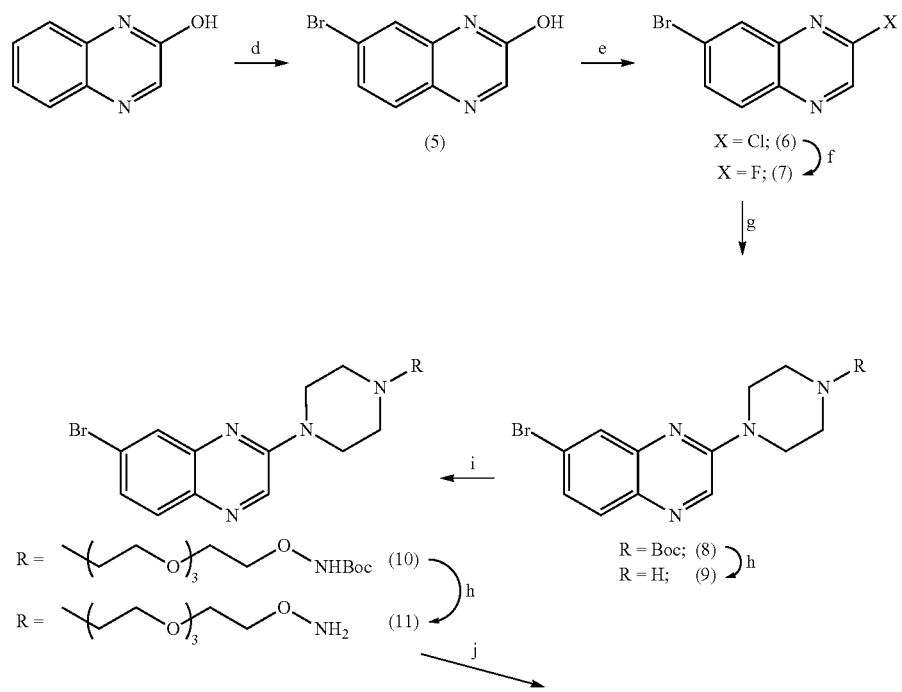

-continued
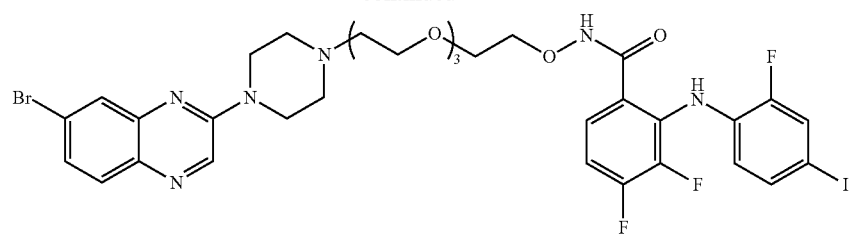
(12)
Reagents and conditions:
(d) Br$_2$, HAc, rt;
(e) POCl$_3$, toluene, rt;
(f) TBAF, DMSO, rt;
(g) NBoc-piperazine;
(h) TFA, DCM, 0-5° C.;
(i) TosO—(CH$_2$CH$_2$O)$_4$NH(Boc), K$_2$CO$_3$, toluene, reflux;
(j) 3,4-difluoro-2-(2-fluoro-4-iodophenylamino)benzoic acid, DIEA, PyBop, THF:DCM.
Step 3
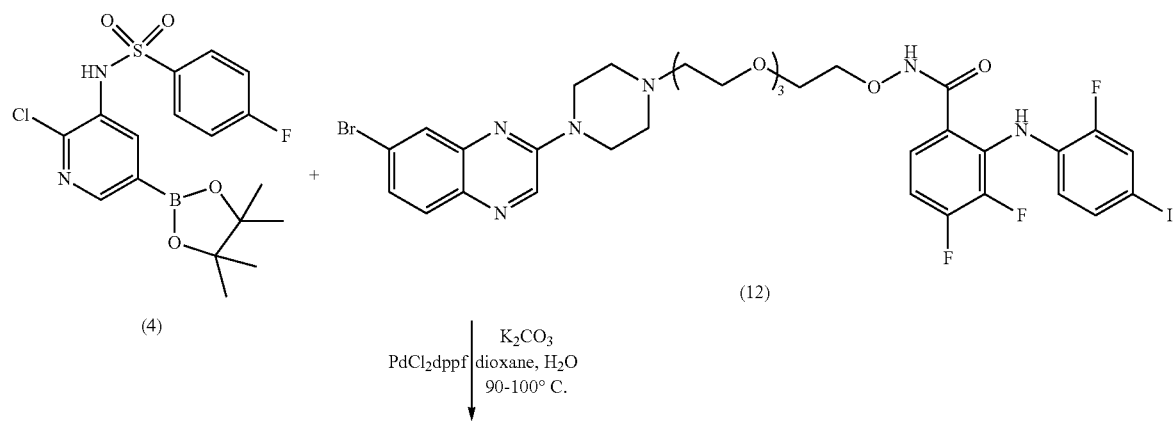
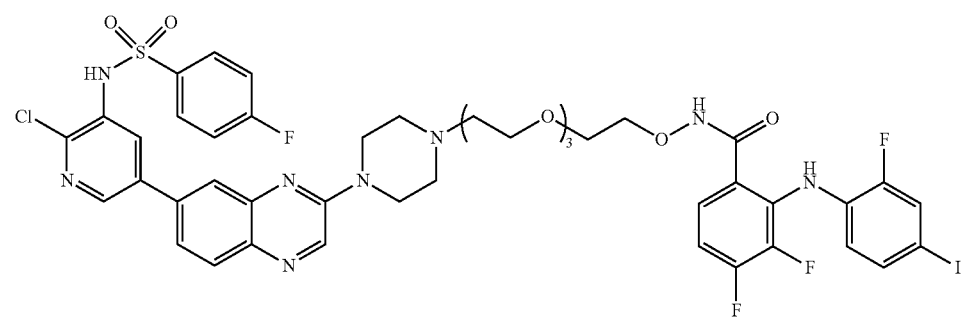
(ST-181)

Synthesis of ST-181 (contd.)
Synthesis of ST-5-35
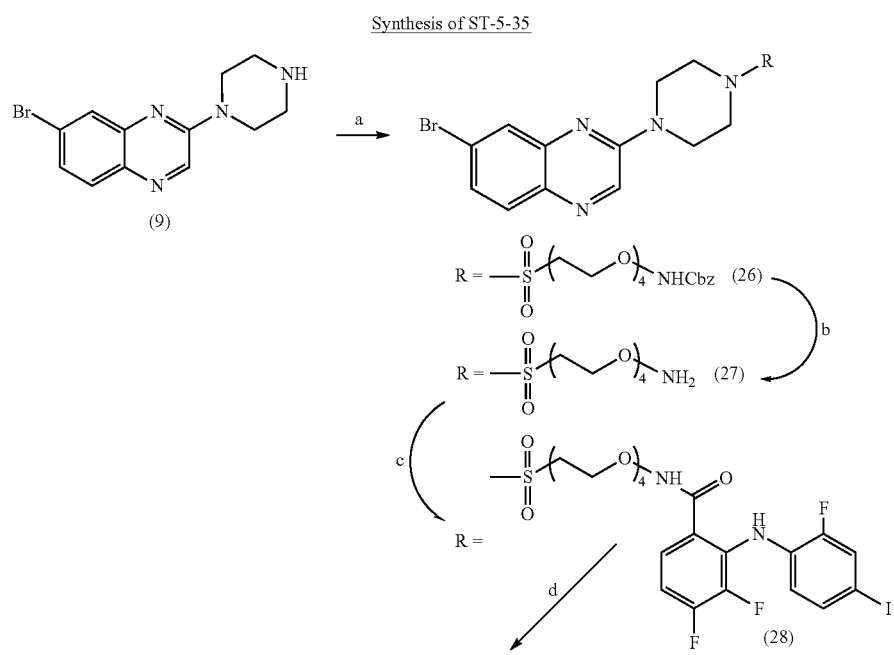
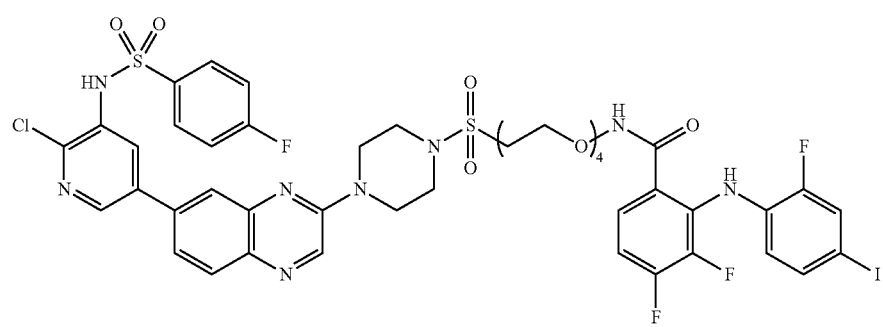
(ST-5-35)
Reagents and conditions: (a) CbzNH(OCH$_2$CH$_2$)$_4$SO$_2$Cl, DIEA, DCM; (b) (CH$_3$)$_3$SiI, CH$_3$CN, 25° C.; (c) 3,4-difluoro-2-(2-fluoro-4-iodophenylamino)benzoic acid, DIEA, PyBop, THF:DCM; (d) 4, PdCl$_2$dppf, K$_2$CO$_3$, dioxane, H$_2$O, 90-100° C.

Synthesis of ST-182
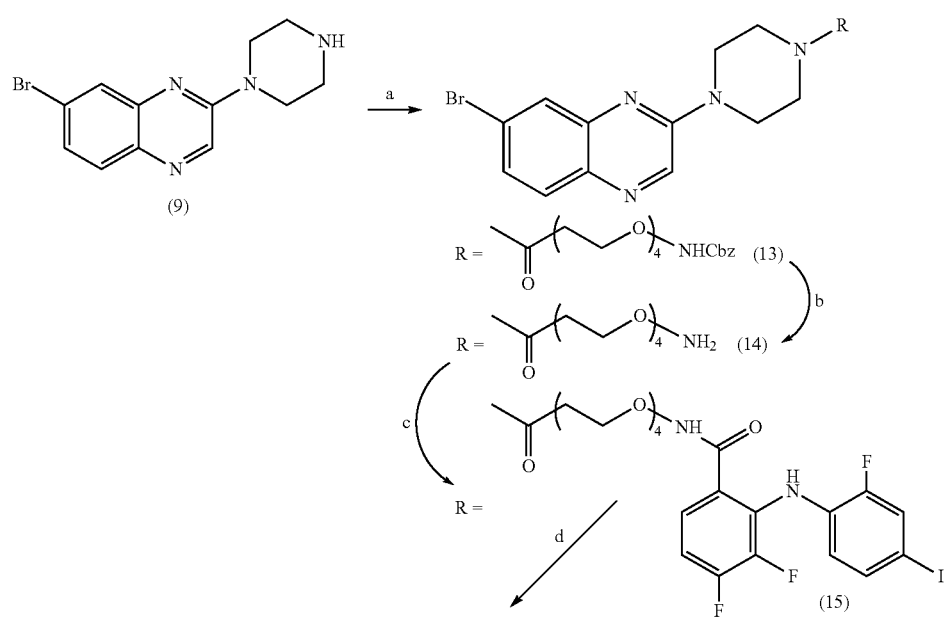
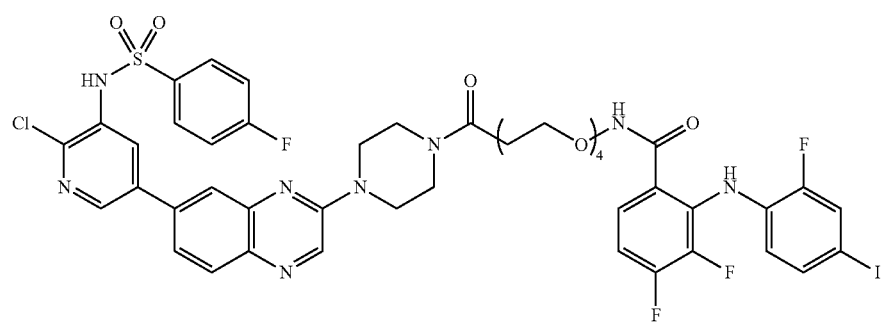
(ST-182)
Reagents and conditions: (a) BocNH(OCH₂CH₂)₄COOH, DIEA, PyBop, THF:DCM; (b) TFA, DCM, 0-5° C.; (c) 3,4-difluoro-2-(2-fluoro-4-iodophenylamino)benzoic acid, DIEA, PyBop, THF:DCM; (d) 4, PdCl₂dppf, K₂CO₃, dioxane, H₂O, 90-100° C.
Synthesis of ST-183
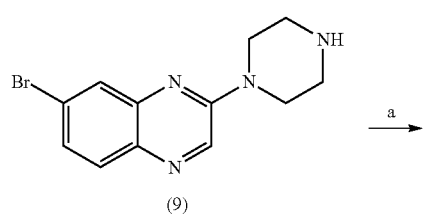

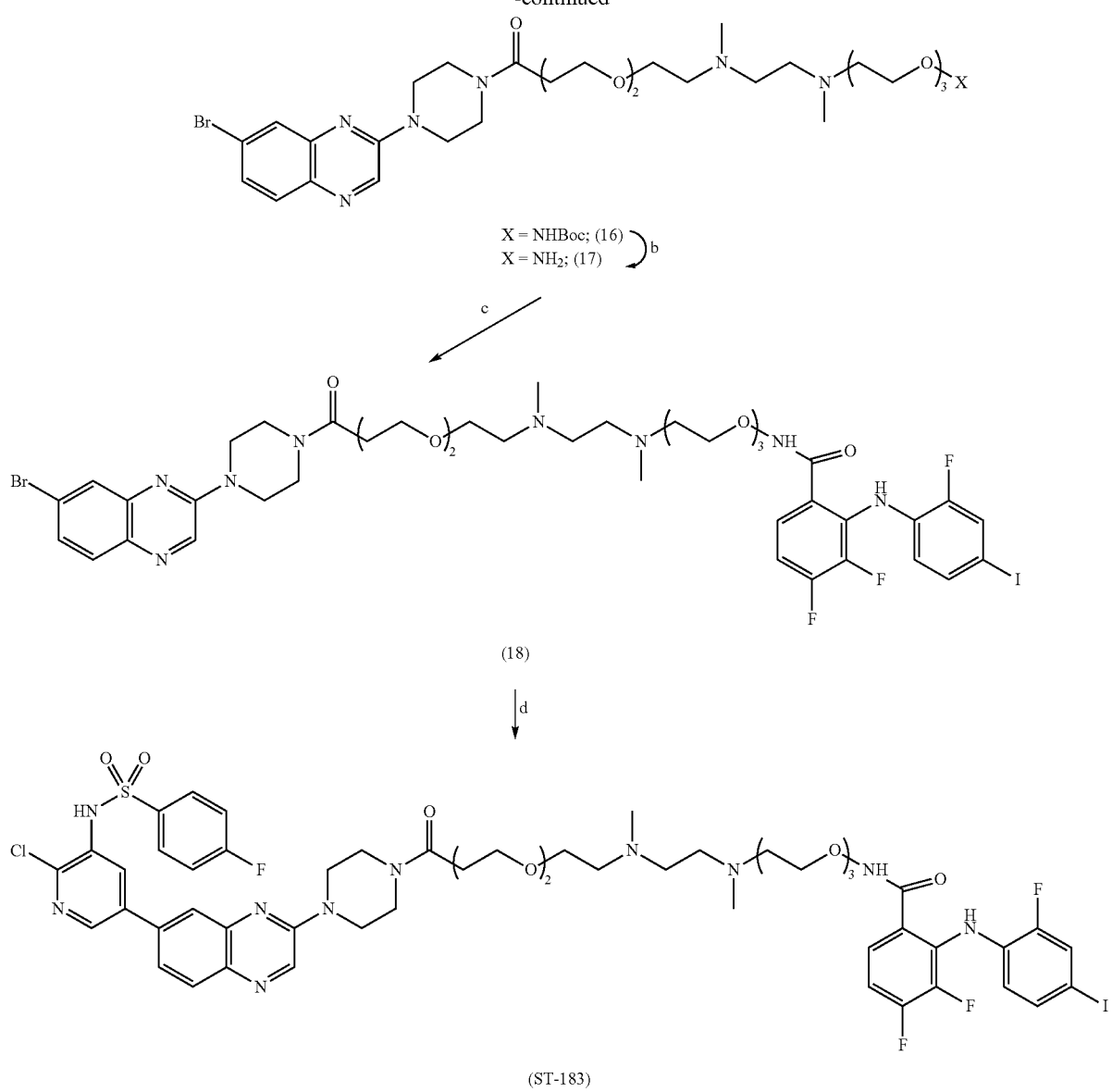
Reagents and conditions: (a) BocNH(OCH$_2$CH$_2$)$_3$N(CH$_3$)CH$_2$CH$_2$N(CH$_3$)(CH$_2$CH$_2$O)$_2$CH$_2$CH$_2$COOH, PyBop, DIEA, THF:DCM; (b) TFA, DCM, 0-5° C; (c) 3,4-difluoro-2-(2-fluoro-4-iodophenylamino)benzoic acid, DIEA, PyBop, THF:DCM; (d) 4, PdCl$_2$dppf, K$_2$CO$_3$, dioxane:H$_2$O, 90-100° C.
Synthesis of ST-184
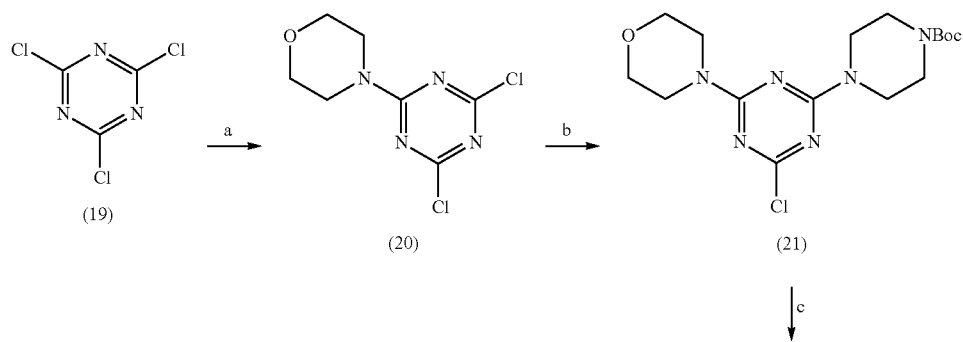

87

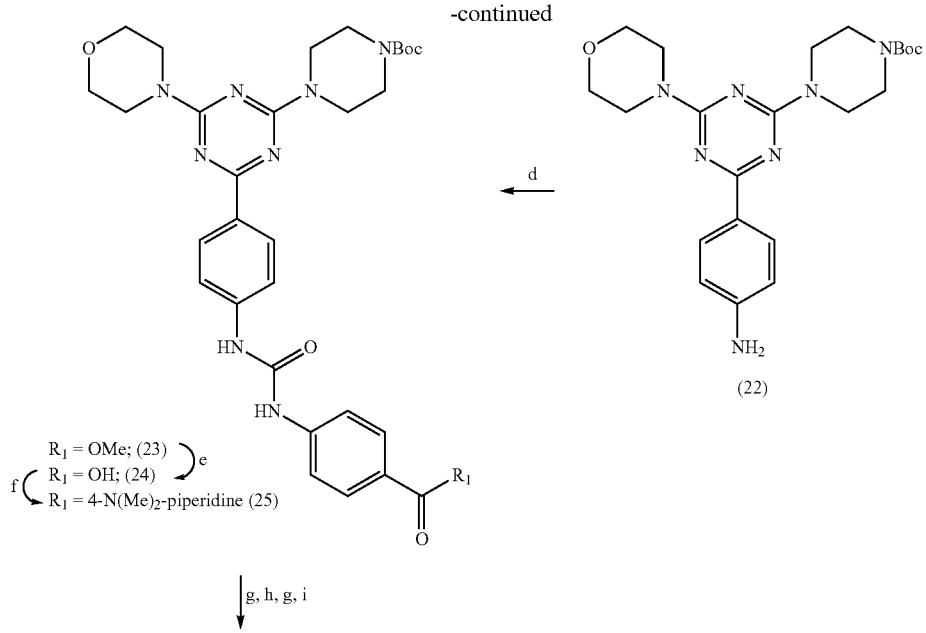

88
-continued (22)

R₁ = OMe; (23)
R₁ = OH; (24)
R₁ = 4-N(Me)₂-piperidine (25)

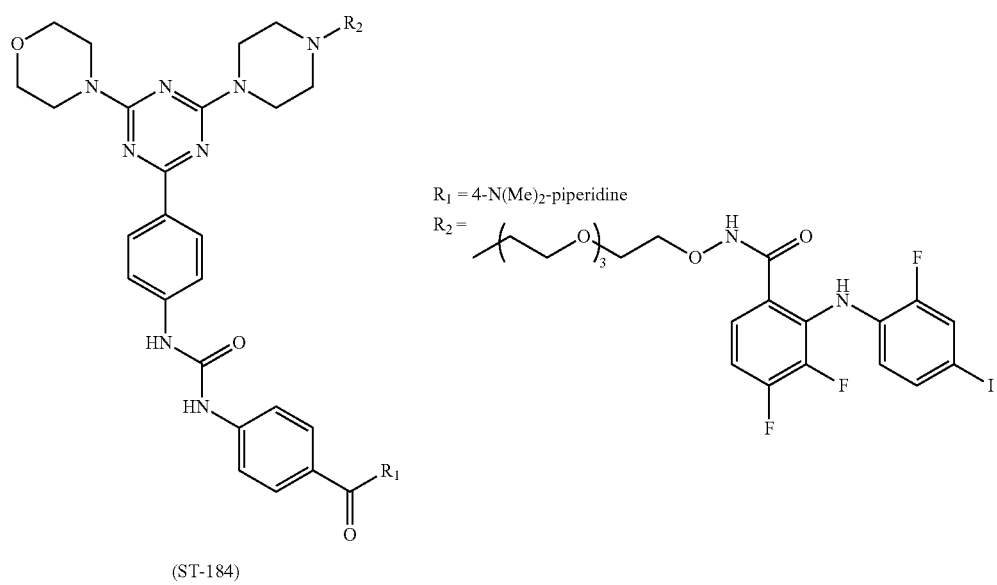

$R_1$ = 4-N(Me)₂-piperidine (ST-184)

Reagents and conditions: (a) morpholine, DIEA, DCM, -78° C.; (b) N-Boc piperazine, K₂CO₃, DMF, rt; (c) 4-aminophenylboronic acid pinacol ester, Pd(PPh₃)₄, DME, 2N Na₂CO₃, reflux; (d) methyl-4-isocyanatobenzoate, DCM, rt; (e) 5N NaOH, MeOH:THF, 70° C.; (f) 4-(N,N-dimethylamino) piperidine, HOBt, EDCI, Et₃N, THF, rt; (g) TFA, DCM, 0-5° C.; (h) Tos-PEG₄NH(t-Boc), K₂CO₃, toluene, reflux; (i) 3,4-difluoro-2-(2-fluoro-4-iodophenylamino)benzoic acid, DIEA, PyBop, THF:DCM.

Synthesis of ST-185 and ST-186

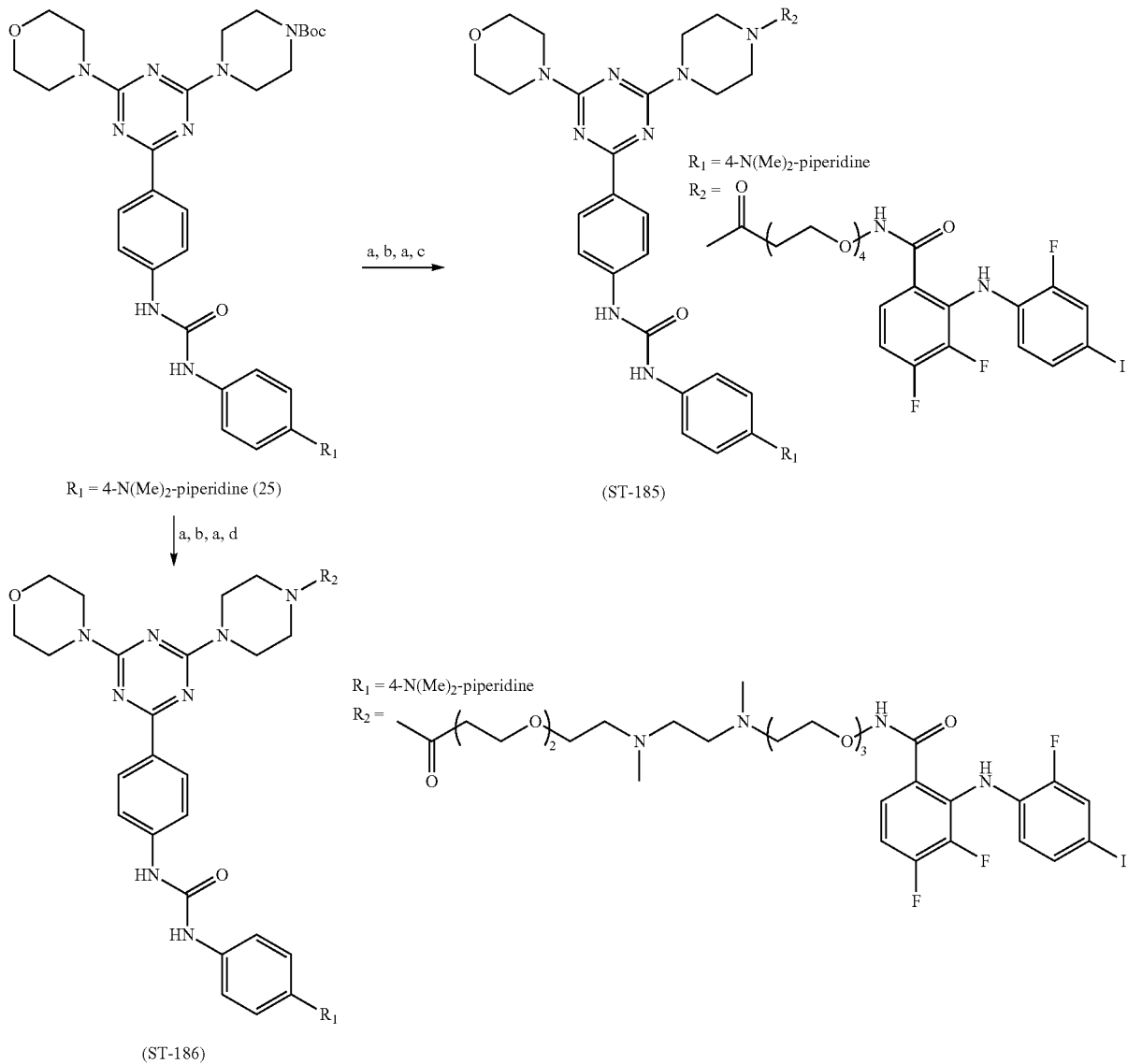

Reagents and conditions: (a) TFA, DCM, 0-5° C.; (b) BocNH(OCH$_2$CH$_2$)$_4$COOH, DIEA, PyBop, THF:DCM; (c) 3,4-difluoro-2-(2-fluoro-4-iodophenylamino)benzoic acid, DIEA, PyBop, THF:DCM; (d) BocNH(OCH$_2$CH$_2$)$_3$N(CH$_3$)CH$_2$CH$_2$N(CH$_3$)(CH$_2$CH$_2$O)$_2$CH$_2$CH$_2$COOH, DIEA, PyBop, THF:DCM.

Biological Data

FIG. 1 shows the docked structures of compound 14 at MEK1 allosteric pocket and PI3Kα. FIG. 1A shows the binding mode of compound 14 within the MEK1 (PDB code 3WIG) allosteric catalytic site. The PI3K portion of compound 14 is out to solvent (left). FIG. 1B shows the binding mode of compound 14 to PI3K (PDB code 2WXK) catalytic site. MEK1 binding portion is out to solvent (left). 7-Orbital stacking interactions are shown as hashed lines, hydrogen bonds also are shown as hashed lines.

SAR of MEK1 and PI3K Inhibition for Bifunctional Inhibitor Analogs.

The in vitro MEK1 and PI3K inhibition data for inhibitor analogs are presented in Table 1. All analogs in the series demonstrated significantly high MEK1 inhibition in the low nanomolar to subnanomolar range (0.015 nM<IC$_{50}$<56.7 nM). The high degree of observed MEK inhibition as exemplified by analogs 9 and 14 could be due to retention of the key hydroxamate side chain structural elements of the potent MEK1 inhibitors PD0316684 and 5 in the linker portion of the inhibitor structures. The corresponding PI3K inhibitory activity for these series of inhibitors was less pronounced (54 nM<IO$_{50}$<341 nM) with compound 7 displaying the highest PI3K inhibition (IO$_{50}$=54 nM) in the series. The improved PI3K inhibition of 7 compared to 9 could be due to its extended linker chain length, although additional electronic interactions attributed to the amide bond in the linker could also play a role. The similar PI3K potency (191 nM<IC$_{50}$<341 nM) displayed by analogs 9, 11, and 14 also suggests that the nature of the linker attachment at the piperazine nitrogen plays a minor role in influencing PI3K inhibition. The calculated lipophilicities (c Log P) for bifunctional inhibitors were in the range of 4.84-5.71 (Table 1) approaching the acceptable threshold (c Log P<5) for oral bioavailability.

which correlates well with the in vitro inhibition data (Table 1). Both MEK and PI3K inhibition was most pronounced in cell lines treated with compounds 9 and 14 compared to compounds 7 and 11.

TABLE 1

In Vitro MEK1 and PI3K Enzyme Inhibition Data[a]

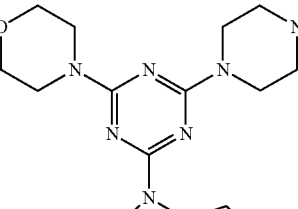

| Compound | Linker (X) | cLogP | $IC_{50}$ (nM)[#] MEK1 | PI3K |
|---|---|---|---|---|
| 7 | —C(=O)—(CH)$_5$NHCOCH$_2$NHCH$_2$CH$_2$— | 4.84 | 0.50 ± 1.2 | 54 ± 25 |
| 9 | —C(=O)—(CH)$_5$NHCH$_2$CH$_2$— | 5.58 | 0.019 ± 3.09 | 341 ± 56 |
| 11 | —S(=O)$_2$—(CH)$_4$NHCH$_2$CH$_2$— | 5.48 | 56.7 ± 1.3 | 285 ± 36 |
| 14 | —(CH$_2$CH$_2$O)$_3$CH$_2$CH$_2$— | 5.71 | 0.15 ± 1.57 | 191 ± 64 |
| 5 | n.a. | 3.75 | 0.00715 ± 1.40 | n.d. |
| PD0316684 | n.a. | 3.68 | 13.0 ± 1.6 | n.d. |
| PD0325901 | n.a. | 2.85 | 15.0 ± 1.3 | n.d. |

[a]Footnotes are the following.
Binding data are the average of three experiments each conducted in duplicate.
†cLogP data were obtained using Chem Draw Professional (version 15.0.0.106).

Cellular Efficacy and Viability Studies.

Figure 2:
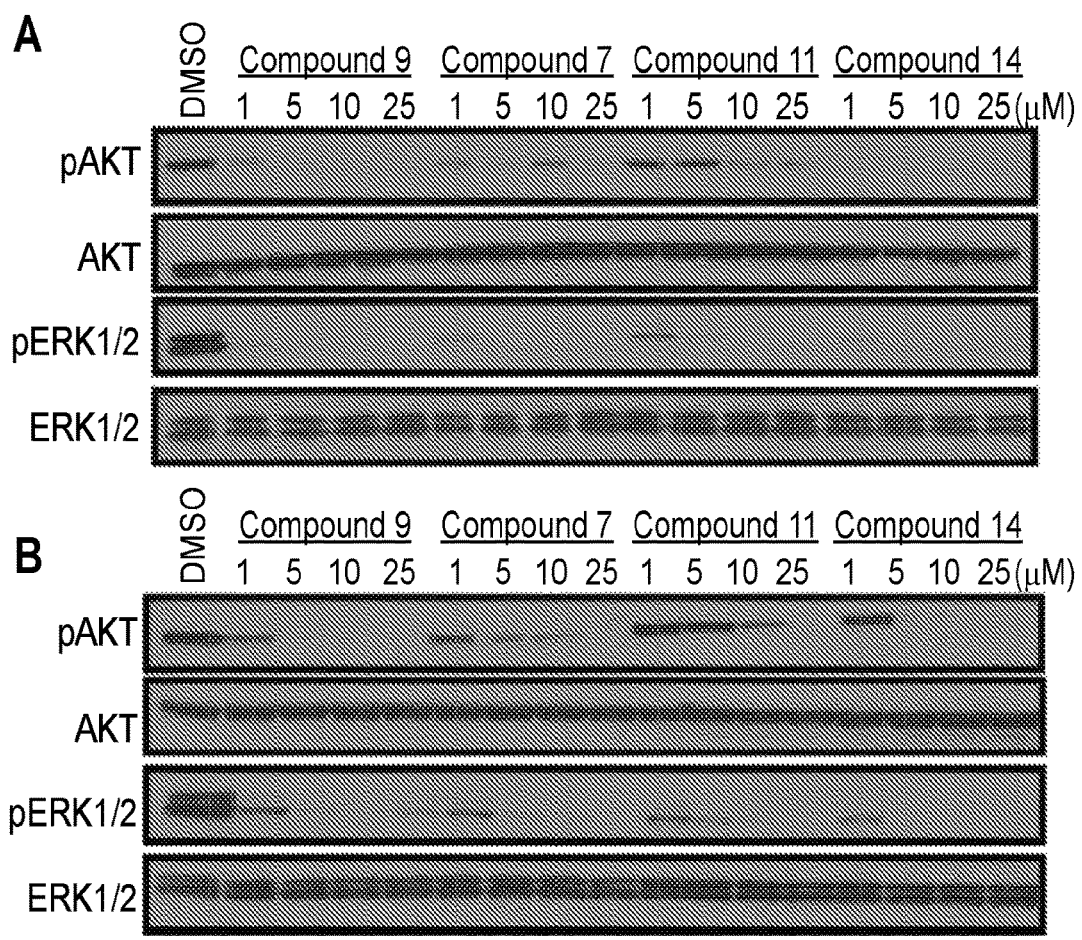
FIG. 2 shows the in vitro activity of compounds 7, 9, 11, and 14 targeting MAPK/ERK and PI3K/AKT pathways from cultured A-549 lung tumor (FIG. 2A) and D54 glioma cells (FIG. 2B)

The in vitro MEK1 and PI3K inhibitory activity of these series of compounds was also assessed in cultured tumor cells (D54, A549). Cellular efficacy of MEK1 and PI3K inhibition by inhibitor compounds was measured by changes in phosphorylation of pErk1/2 and pAkt, respectively. FIG. 2 shows the in vitro activity of compounds 7, 9, 11, and 14, i.e., activity of compounds for in vitro targeting MAPK/ERK and PI3K/AKT pathways by Western blot analysis of protein lysates obtained from cultured A549 lung tumor FIG. 2A and D54 glioma cells FIG. 2B. Cells were incubated in the presence of indicated compounds for 1 hour and lysates probed with specific antibodies against pAKT and pERK 1/2 and compared with vehicle control (DMSO). A549 (FIG. 2A) and D54 (FIG. 2B) cells were treated with inhibitors at the indicated concentrations for 1 hour and subjected to Western blot analysis. As shown in FIG. 2A, in cultured A549 cells, all compounds in this series displayed a decrease of phosphorylation of pERK1/2, demonstrating the potent efficacy of these compounds in inhibiting enzymatic activity of MEK1 kinase. Similarly, compounds 7, 9, and 14 also showed high potency in inhibiting PI3K activity, as indicated by the low level of pAKT in treated cell samples. Noticeably, all inhibitor analogs also demonstrate significant inhibition of MEK activity in both cell lines The effect of the series of novel compounds on cell viability was determined using the AlamarBlue assay. A549 and D54 tumor cells were treated with bifunctional inhibitor analogs (compounds 7, 9, 11, and 14), MEK1 inhibitor (PD0325901), PI3K inhibitor (ZSTK474), and a combination of ZSTK474 and PD0325901 at 48 hours prior to assay analysis. FIG. 3 shows the Quantification of in vitro activity of compounds 7, 9, 11, and 14 by a dose dependence of cell viability following exposure to compounds 7, 9, 11, 14 and the PI3K inhibitor ZSTK474 and MEK inhibitor PD0325901 at the indicated concentrations in (A) A549 lung tumor cells and (B) D54 glioma cells. The percentage of viable tumor cells was determined at 24 hours following exposure.

Figure 3A:
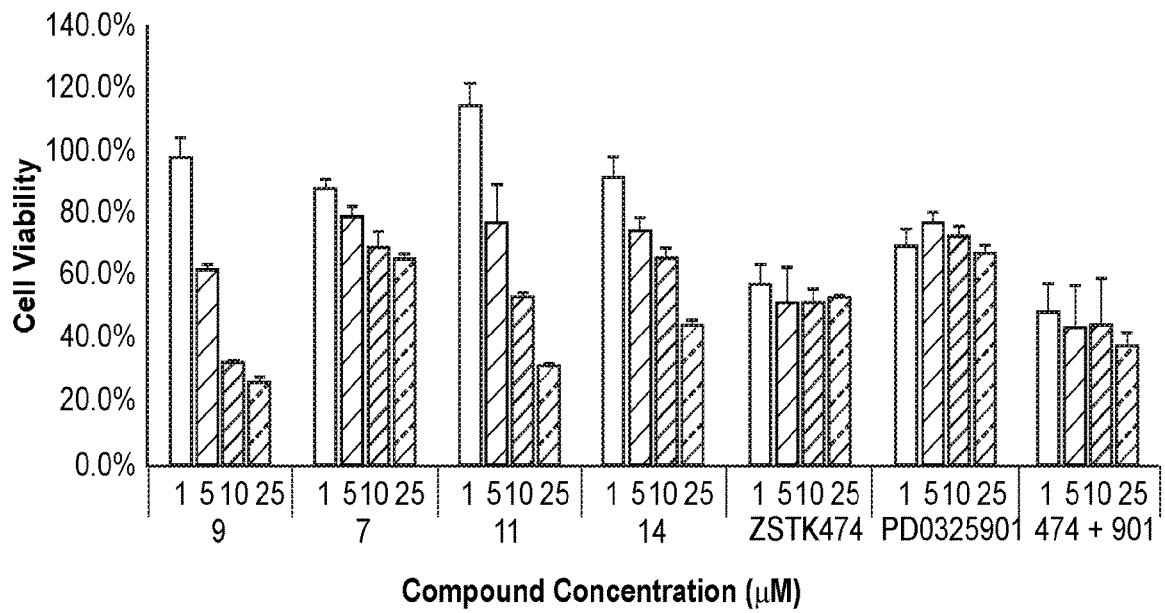
FIG. 3 shows the quantification of in vitro activity of compounds 7, 9, 11, and 14.
Figure 3B:
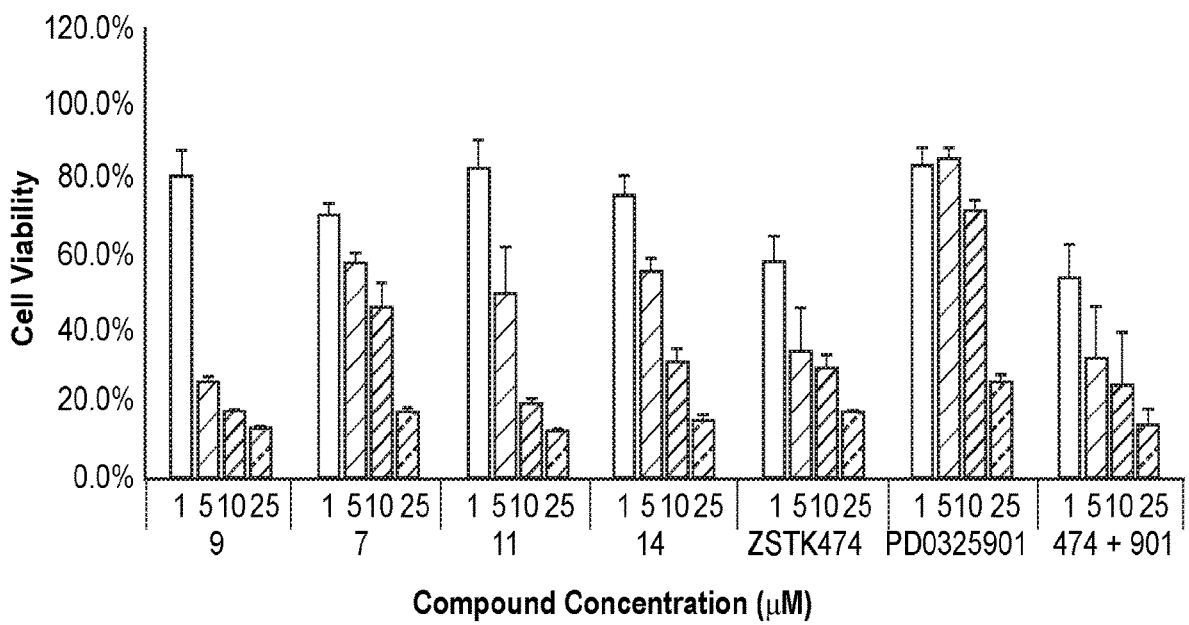

As shown in FIG. 3A and FIG. 3B, all inhibitors produced a dose-dependent decrease in cell viability in both A549 (FIG. 3A) and D54 (FIG. 3B) tumor cell lines. In particular, compounds 9 and 14 were similar to or in some cases exceeded the therapeutic effects of individual monotherapies (e.g., PD0325901) by compromised cell viability in both cell lines. Interestingly, compounds 9 and 14 were found to be as effective as the combination of ZSTK474 and PD0325901 in terms of the loss of cellular viability in both cell lines (FIG. 3A, FIG. 3B). Significantly, compounds 9 and 14 were found to have significant antitumor activity which was similar to that of the combination therapy consisting of co-incubation with ZSTK474 and PD0325901 (FIG. 3A, FIG. 3B).

In Vivo MEK1 and PI3K Inhibition Activity in Tumor Bearing Mice.

On the basis of the combination of the in vitro inhibition data and cellular efficacy/viability studies, compound 14 was used for further in vivo evaluation. Four athymic nude Foxn1nu mice were used to evaluate oncogenic target modulation activity in vivo. Mice bearing flank D54 (n=2) and A549 (n=2) tumors were treated with either vehicle or 375 mg/kg of compound 14 by oral gavage at 2 h prior to sacrifice. FIG. 4A and FIG. 4B show the In vivo MEK1 and PI3K inhibition activity in tumor bearing mice. Mice bearing D54 and A549 subcutaneous tumors were treated with either vehicle or 375 mg/kg of compound 14 by oral gavage at 2 hours prior to sacrifice. In FIG. 4A, Western blot analysis of excised tumor tissue showed that compound 14 successfully modulated both MEK1 and PI3K activities in a D54 tumor relative to vehicle control. In FIG. 4B, Western blot analysis of excised A549 tumor tissue showed that compound 14 successfully modulated both MEK1 and PI3K activities in A549 tumor relative to vehicle control. These data demonstrate in vivo bioavailability and efficacy of compound 14 for suppression of MEK1/PI3K kinase activities in vivo in solid tumors, confirming that simultaneous in vivo inhibition of the Ras/MEK/ERK and PI3K/Akt/mTor pathways using a single chemical entity bifunctional inhibitor (compound 14) could be achieved. Western blot analysis of excised tumor tissue revealed that compound 14 inhibited phosphorylation of ERK1/2 and Akt in both tumor types (FIG. 4A and FIG. 4B). Furthermore, in another preliminary experiment using compound 9 modulation of ERK1/2 and pAkt levels was also achieved in mouse tumors for both A549 and D54 tumors (data not shown). Overall, taken together, these data clearly demonstrate that simultaneous suppression of MEK1/PI3K activity can be achieved both in vitro and in vivo by the bifunctional inhibitor compounds 9 and 14.

Upregulation of the Ras/MEK/ERK and PI3K/Akt/mTor signaling cascades in response to growth factor stimulation has been demonstrated in many human cancers. Studies have also shown that MEK inhibition promotes a compensatory activation of PI3K/Akt kinase activity. Accordingly, co-targeting of these two signaling pathways has been recognized as a promising chemotherapeutic strategy in effective cancer treatment. To address this goal, a series of prototype bifunctional MEK/PI3K inhibitors were developed by the covalent linking of structural analogs of the ATP-competitive inhibitor ZSTK474 with the ATP-noncompetitive class of MEK inhibitors as represented by PD0325901 using a variety of spacer groups. All inhibitors demonstrated nanomolar to submicromolar inhibition of MEK1 as well as PI3K kinase activity in in vitro enzymatic inhibition assays and a dosedependent decrease in cell viability in the A549 lung adenocarcinoma and D54 glioma cell lines. Additionally, all inhibitors demonstrated significant inhibition of MEK1 activity in these two cell lines in correlation with demonstrating in vitro anticancer activity. Preliminary in vivo studies conducted in D54 and A549 tumor-bearing mice with compound 14 after oral administration revealed significant inhibition of MEK1 and PI3K activity at 2 hours postadministration, confirming in vivo efficacy toward target modulation. To the best of our knowledge, this work represents the first demonstration of simultaneous in vivo inhibition of the Ras/MEK/ERK and PI3K/Akt/mTor pathways using a single chemical entity bifunctional inhibitor.

Figure 5:
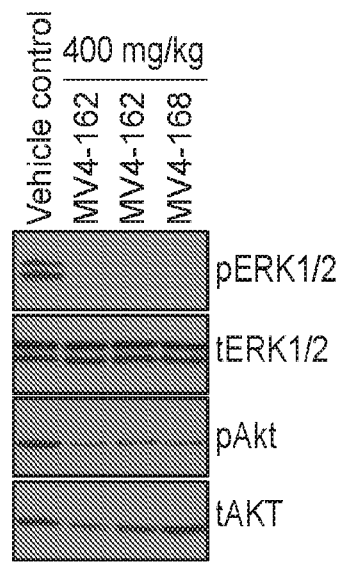
FIG. 5 shows the in vivo MEK1 and PI3K inhibition activity in intracerebral D54 glioma bearing mice by MV4-162 (compound 14) or MB4-168.

FIG. 5 shows the In vivo MEK1 and PI3K inhibition activity in intracerebral D54 glioma bearing mice. Mice bearing i.c. D54 tumors were treated with either vehicle or 400 mg/kg of ST-162 or ST-168 by oral gavage at 2 hours prior to sacrifice. Western blot analysis of excised tumor tissue showed that both compounds successfully modulated both MEK1 and PI3K activities in the intracerebral D54 tumor relative to vehicle control. These data demonstrate in vivo bioavailability and efficacy of ST-162 and ST-168 for suppression of MEK1/PI3K kinase activities in vivo in solid tumors, confirming that simultaneous in vivo inhibition of the Ras/MEK/ERK and PI3K/Akt/mTor pathways using a single chemical entity bifunctional inhibitor (compounds ST-162 and ST-168) could be achieved.

Figure 6:
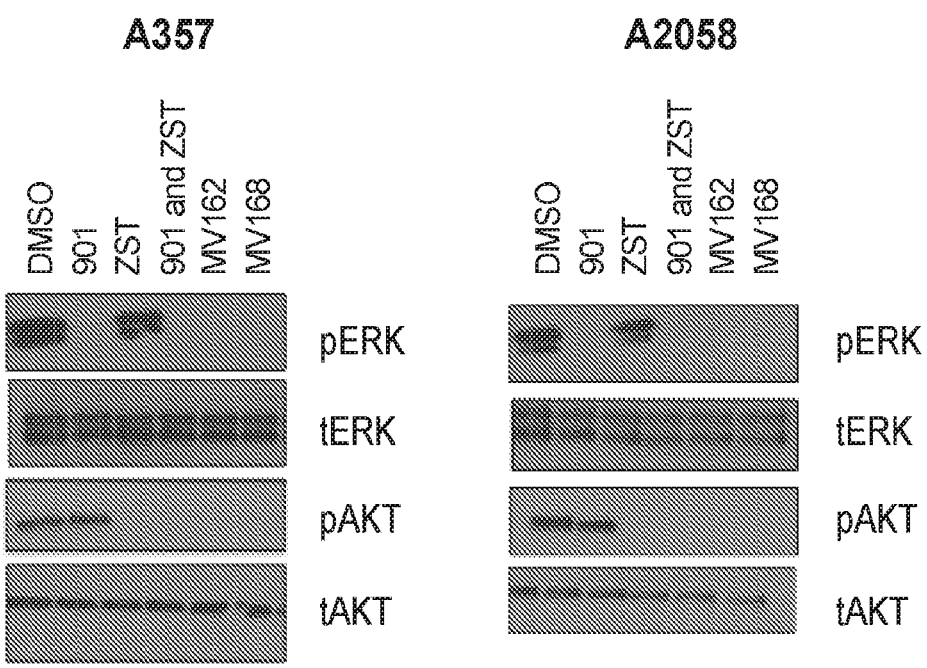
FIG. 6 shows the in vivo MEK1 and PI3K inhibition activity in subcutaneous growing melanoma tumor lines A357 and A2058 in mice.

FIG. 6 shows the in vivo MEK1 and PI3K inhibition activity in subcutaneous growing melanoma tumor lines A357 and A2058 in mice. Mice bearing s.q. melanoma tumors were treated with either vehicle or 400 mg/kg of ST-162 or ST-168 by oral gavage at 2 hours prior to sacrifice. Western blot analysis of excised tumor tissue showed that both compounds successfully modulated both MEK1 and PI3K activities in these human melanoma tumors relative to vehicle control. These data demonstrate in vivo bioavailability and efficacy of ST-162 and ST-168 for suppression of MEK1/PI3K kinase activities in vivo in solid tumors, confirming that simultaneous in vivo inhibition of the Ras/MEK/ERK and PI3K/Akt/mTor pathways using a single chemical entity bifunctional inhibitor (compounds ST-162 and ST-168) could be achieved.

Figure 7:
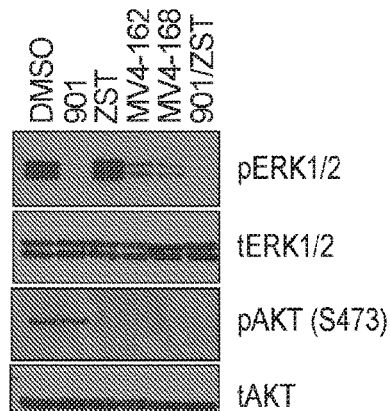
FIG. 7 shows the in vivo MEK1 and PI3K inhibition activity in subcutaneous growing colon cancer tumor line CT26 in mice.

FIG. 7 shows the in vivo MEK1 and PI3K inhibition activity in the subcutaneous growing colon cancer tumor line CT26 in mice. Mice bearing subcutaneous colon tumors were treated with either vehicle or 400 mg/kg of ST-162 or ST-168 by oral gavage at 2 hours prior to sacrifice. The known MEK inhibitor 901 and PI3K inhibitors were also evaluated in this study. Western blot analysis of excised tumor tissue showed that ST-162 and ST-168 successfully modulated MEK1 and PI3K activities in this human colon tumor model relative to vehicle control. These data demonstrate in vivo bioavailability and efficacy of ST-162 and ST-168 for suppression of MEK1/PI3K kinase activities in vivo in solid colon tumors, confirming that simultaneous in vivo inhibition of the Ras/MEK/ERK and PI3K/Akt/mTor pathways using a single chemical entity bifunctional inhibitor (ST-162 and ST-168) could be achieved.

In preliminary studies, several mouse models were tested for therapeutic efficacy using oral administration of ST-162. Athymic nude Foxn1 nu mice were used to evaluate oncogenic target modulation activity in vivo. Mice bearing intracerebral D54 tumors, subcutaneous colon tumors (CT26) and subcutaneous melanoma (A375 and A2058) tumors were treated with either vehicle control or 400 mg/kg of compound ST-162 by oral gavage for 14-30+ days. All studies revealed significant tumor growth delays could be achieved (CT26, A375, and A2058) or improved animal survival (D54).

Figure 8:
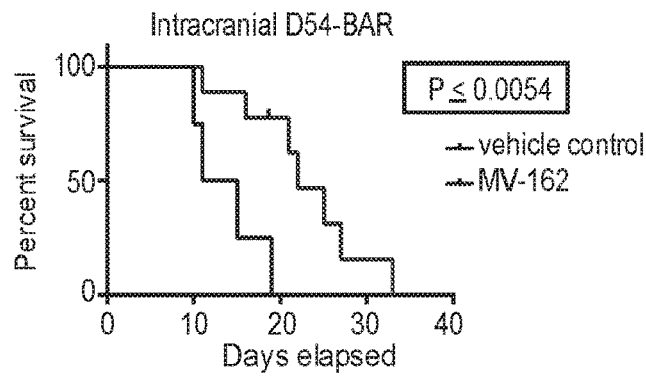
FIG. 8 is a graph showing percent survival vs. days elapsed for animals treated with MV4-162 (compound 14)

FIG. 8 is a study using compound ST-162 administered beginning when intracerebral tumors reached a volume of approximately 20 microliters (measured by MRI), a significant improvement (P=0.0054) in overall survival was found as compared to vehicle control animals. This data clearly demonstrate that simultaneous suppression of MEK1/PI3K activity can be achieved in vivo by the bifunctional inhibitor ST-162 in intracerebral human D54 glioma tumors.

Figure 9:
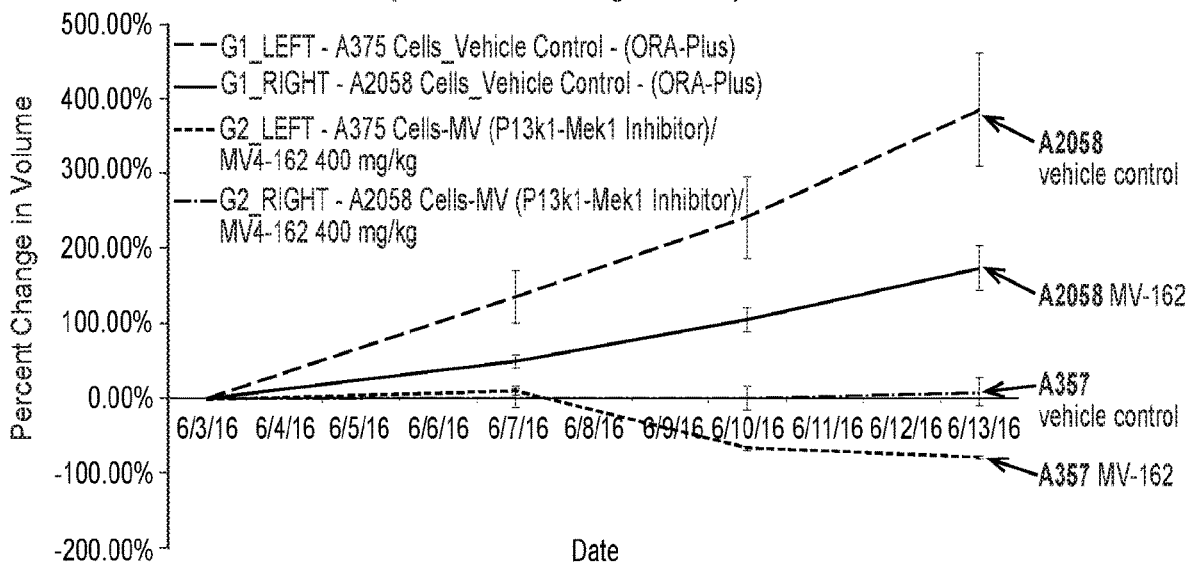
FIG. 9 contains graphs showing tumor volumes of melanoma tumors A2058 and A357 for MV-162 (compound 14) and vehicle control treated animals.

In FIG. 9, compound ST-162 was administered for 14 days beginning when subcutaneous melanoma tumors A2058 and A357 were measurable by caliper and MRI and tumor volumes were measured over time and compared to vehicle controls. A significant reduction of tumor growth was observed for both melanoma tumor models in ST-162 treated animals compared to vehicle control animals. This data clearly demonstrate that simultaneous suppression of MEK1/PI3K activity can impact in vivo growth rates due to treatment with the bifunctional inhibitor ST-162 in human melanoma tumors.

Figure 10:
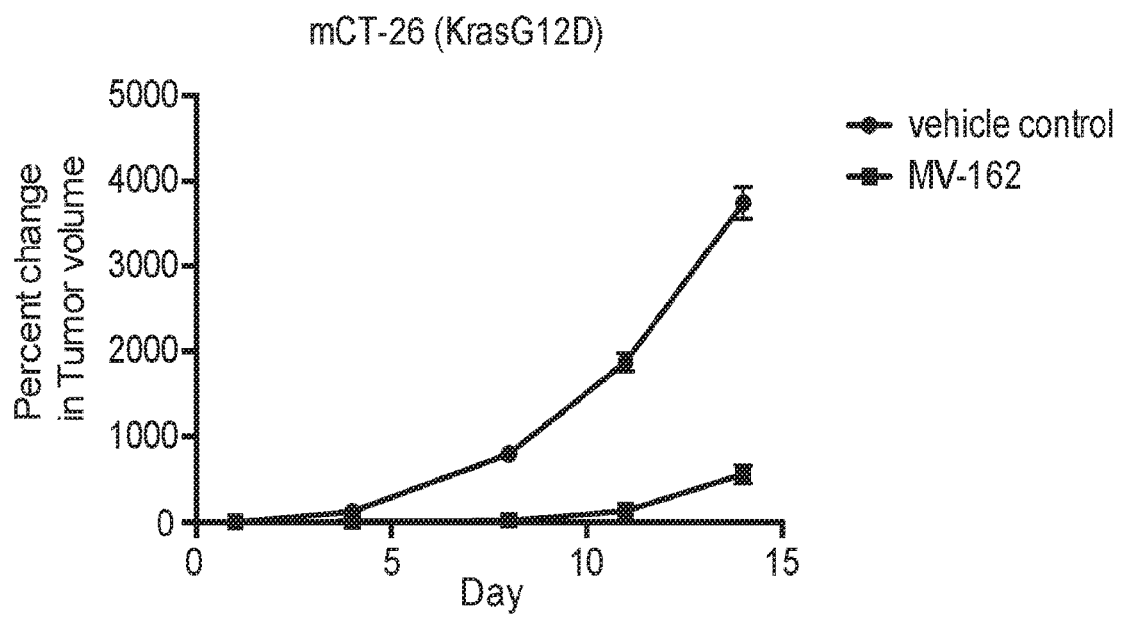
FIG. 10 contains graphs showing percent change in tumor volume vs. days for animals treated with a vehicle control and MV4-162 (compound 14)

In FIG. 10, compound ST-162 was administered for 14 days beginning when subcutaneous colon tumors CT-26 were measurable by caliper and MRI and tumor volumes were measured over time and compared to vehicle controls. A significant reduction of tumor growth was observed for CT-26 tumors in MV4-162 (compound 14) treated animals compared to vehicle control animals. This data clearly demonstrate that simultaneous suppression of MEK1/PI3K activity can impact in vivo growth rates due to treatment with the bifunctional inhibitor ST-162 in human colon tumors.

Figure 11:
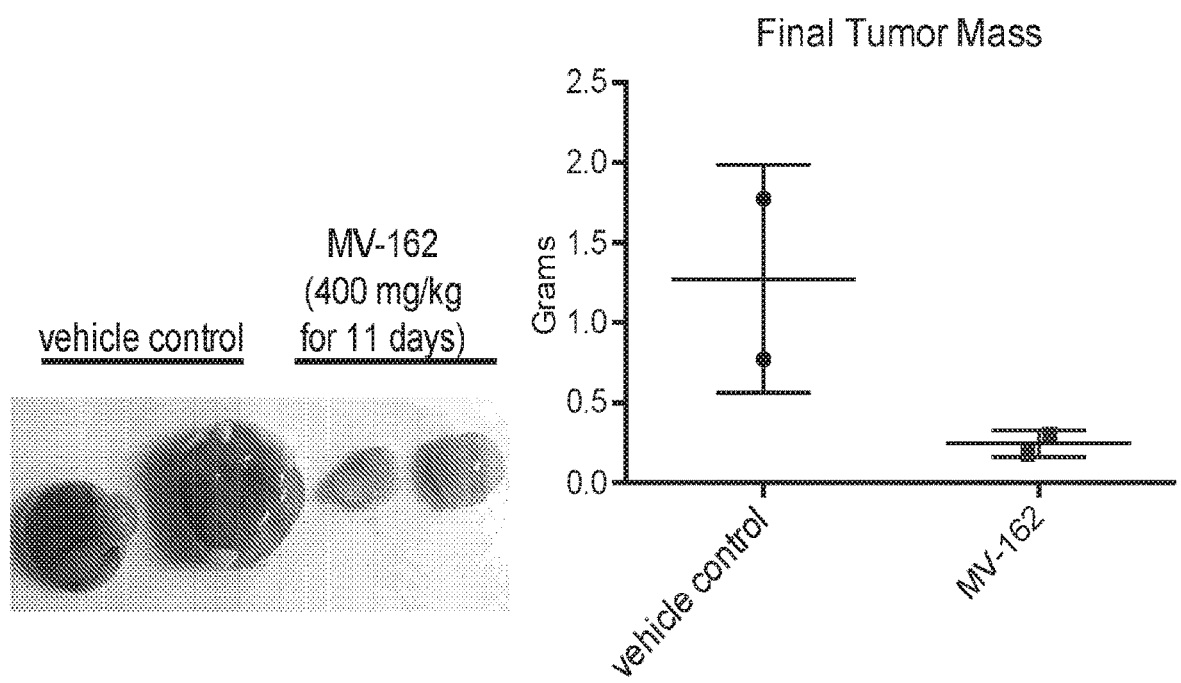
FIG. 11 illustrates and graphs tumor mass for mice treated with compound 14 (MV4-162) and a vehicle control.

In FIG. 11, ST-162 was administered for 14 days beginning when subcutaneous colon tumors CT-26 were measurable by caliper and MRI and tumor volumes were measured over time and compared to vehicle controls. At day 14, two tumors were removed and compared for size and weight. As shown, vehicle control tumors were significantly larger than those harvested from mice treated with ST-162 for 14 days. This data demonstrates that simultaneous suppression of MEK1/PI3K activity can impact in vivo tumor volumes due to treatment with the bifunctional inhibitor ST-162 in human colon tumors as treated tumors were smaller in volume versus vehicle control treated tumors.

In Vitro MEK1 Inhibition Assays.

In vitro MEK1 inhibition activity of inhibitor analogs were determined using Kinase-Glo luminescent kinase assay kits from Promega (WI, USA) per manufacturer's instructions. Purified MEK1 and inactive Erk2 were purchased from Sigma-Aldrich (St. Louis, Mo., USA) and Carna Biosciences (Kobe, Japan), respectively. Briefly, series of compound dilutions were added in 96-well plates, followed by MEK1, Erk2, and ATP solutions. Kinase reactions were run at 30° C. for 30 minutes. Equal volumes of Kinase-Glo solution were then added, and reactions were incubated at room temperature for a further 30 minutes. Bioluminescence signals were acquired with an Envision multilabel reader from Perkin Elmer. Assays were conducted in triplicate with various inhibitor concentrations each run in duplicate. $IC_{50}$ data were calculated using GraphPad Prism software (version 5.0, La Jolla, Calif.).

In Vitro PI3K Inhibition Assays.

Quantitation of PI3K lipid kinase activity was carried out by Life Technologies (Madison, Wis.) with purified enzyme using the fluorescence-based Adapta TR-FRET assay protocol. Assays were conducted in triplicate with various inhibitor concentrations (0.1 nM to 10 µM).

Virtual Docking Models of Bifunctional Inhibitor Analogs.

Docking models of bifunctional inhibitor analogs were obtained using software from Schrödinger Inc. X-ray crystal structures of MEK1 (PDB code 3WIG) and PI3K (PDB code 2WXK) were prepared using the Protein Preparation Wizard in Maestro (Protein Preparation Wizard, Schrödinger, LLC, New York, N.Y.). The protein structure was then used to generate the receptor grids for docking using OPLS2005 with the binding site defined by the native ligand. The bifunctional inhibitor ligands were built and prepared for docking in Maestro using Lig Prep 3.4 (Lig Prep, Schrödinger, LLC, New York, N.Y.). The docking procedures were performed using Glide 6.7 in standard precision mode with default parameters and no constraints (23).

Cell Culture and Cell Death Assays.

A human lung adenocarcinoma epithelial cell line A549 and a glioma cell line D54 were grown in RPMI supplemented with 10% heat-inactivated fetal bovine serum (FBS) and 1% penicillin/streptomycin/glutamine (Gibco, Carlsbad, Calif.). Cells were grown in a humidified incubator at 37° C. with a supply of 5% $CO_2$. Initial testing of the therapeutic effects of inhibitor compounds was accomplished using cell viability assays. Stock solutions of inhibitor compounds (10 mM), ZSTK474 (representative PI3K inhibitor), PD0325901 (representative MEK inhibitor) were prepared in DMSO and used to make final solutions by serial dilution in RPMI media. Control wells were dosed with media containing 1% DMSO carrier solvent. Cell viability was determined 48 hours later using an AlamarBlue assay (Life Technologies, Carlsbad, Calif.) according to the manufacturer's instructions. Fluorescence signals were determined with a PerkinElmer EnVision Xcite multilabel reader (PerkinElmer, Waltham, Mass.).

Western Blot Analysis. Cells were seeded in six-well dishes 24 hours prior to treatment and incubated with the respective inhibitor compound solutions for 1 h. Cells were washed with phosphatebuffered saline (PBS) and lysed with NP-40 lysis buffer (1% $NP_{40}$, 150 mM NaCl, and 25 mM Tris, pH 8.0) supplemented with protease inhibitors (Complete protease inhibitor cocktail, Roche, Basel, Switzerland) and phosphatase inhibitors (PhosSTOP, Roche, Basel, Switzerland). Concentration of protein was determined using Lowry assays (Bio-Rad, Hercules, Calif.), and equal amounts of whole cell protein lysate were loaded in each lane and resolved using 4-12% gradient Bis-Tris gel (Invitrogen, CA). Proteins were transferred to 0.2 µm nitrocellulose membranes (Invitrogen, CA). Membranes were incubated overnight at 4° C. with primary antibodies after blocking, followed by incubation with appropriate horseradish peroxidase (HRP) conjugated secondary antibody at room temperature for 1 hour. ECL-Plus was used to detect the activity of peroxidase according to the manufacturer's protocol (Amersham Pharmacia, Uppsala, Sweden). Antibodies raised against phospho-p44/42 MAPK (Erk1/2) (Thr202/Tyr204), pAKT(5473), phospho-p70 S6K* and total ERK, AKT antibodies were purchased from Cell Signaling Technology (Beverly, Mass., USA), and anti-β actin (conjugated with HRP) was purchased from Abcam (Cambridge, Mass., USA). Secondary HRP antibodies were purchased from Jackson ImmunoResearch (St. Louis, Mo., USA).

In Vivo Evaluation of Inhibitor Efficacy.

All animal experiments were approved by the University Committee on the Use and Care of Animals (UCUCA) at the University of Michigan. Five-week-old athymic nude Foxn1 nu mice were inoculated subcutaneously with $1 \times 10^6$ fully suspended D54 cells into the flanks of two mice, and similarly, two additional mice were inoculated with A549 cells in the flank. Each injectate contained a total volume of 200 µL of cell suspension in 50% RPMI medium mixed with 50% BD Matrigel basement membrane matrix (Becton, Dickinson and Company, East Rutherford, N.J.). When tumor volumes reached approximately 150 $mm^3$ by caliper measurement, mice were deprived of food for 2-4 hours followed by administration with either vehicle (200 µL of DMSO:HPBCD (3:2)) or inhibitor analog ST-162 (375 mg/kg in 200 µL of DMSO/HPBCD (3:2)) orally at 2 hours prior to sacrifice. Tumor tissues were collected from both vehicle and drug-treated groups and subjected to Western blot analysis as previously described.

| PI3K Subtype Inhibition Activity (nM)[+] | | | | |
|---|---|---|---|---|
| Inhibitor | PI3Kα | PI3Kβ | PI3Kγ | PI3Kδ |
| 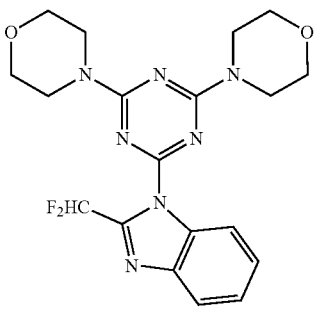<br>(ZSTK474) | 5.0 ± 0.8 | 15.2 ± 1.4 | 20.8 ± 0.6 | 3.9 ± 0.6 |
| 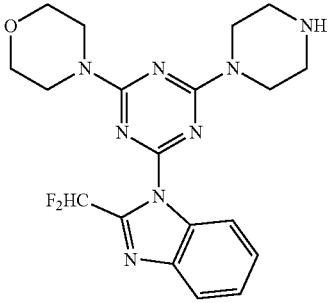<br>(2a) | 180 ± 25 | 1093 ± 168 | 1873 ± 283 | 142 ± 7.5 |
| 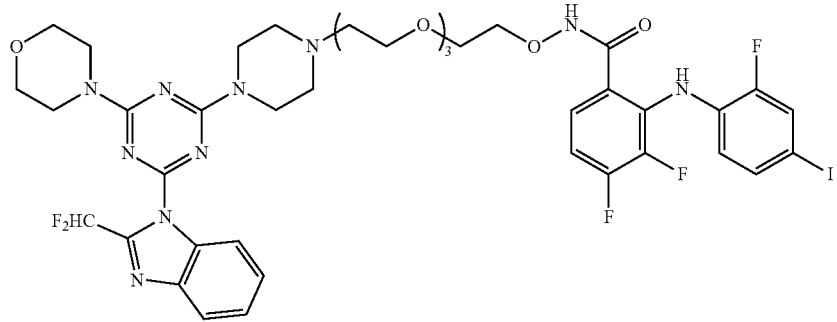<br>ST-162 | 467 ± 9.0 | 4073 ± 290 | 5803 ± 511 | 942 ± 120 |
| 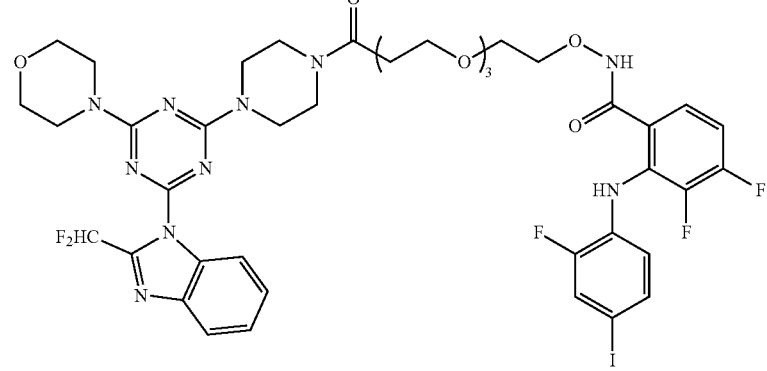<br>ST-168 | 69.2 ± 2.2 | 1482 ± 377 | 2293 ± 241 | 41.7 ± 2.1 |
[+]Data reported as mean ± standard error of the mean (SEM)

The synthesis of another series of single entity, multifunctional inhibitors achieved by covalent linking of structural analogs of a PI3K inhibitor mTOR inhibitor, and an MEK inhibitor is also disclosed. The multifunctional inhibitors displayed potent in vitro inhibition of MEK1 ($182<IC_{50}$ (nM)$<398$), PI3K ($39<IC_{50}$ (nM)$<191$, and mTOR ($50.4<IC_{50}$ (nM)$<53.1$) in enzymatic inhibition assays. Concurrent inhibition was demonstrated by compounds ST-162, ST-168 and ST-180 in tumor cell lines (A375 (melanoma), D54 (glioma), CT26 colorectal cancer), A2058 (melanoma)). Inhibitors produced dose-dependent decreased cell viability similar to the combined administration of ZSTK474 (PI3K inhibition) and PD0325901 (MEK inhibitor). Data obtained from A375 tumor tissue collected from a mouse harboring a solid tumor in the flank showed by Western blot analysis that at 2 hour postadministration of ST-168 orally, a combined inhibition of mTOR/MEK1/PI3K was achieved, confirming the bioavailability and efficacy of the ST-168 multifunctional inhibitor strategy. In vivo efficacy of compound ST-168 following 40 daily oral doses of ST-168 (400 mg/kg) was demonstrated in A375 melanoma tumor bearing mice. In this study ST-168 showed a significant >6-fold reduction in tumor size over vehicle control dosed animals at 35 days post-treatment initiation. A significantly increased lifespan was also observed in these A375 tumor bearing mice treated with ST-168 with no detectable side effects (such as loss in body weight) due to long term drug dosage.

PI3K Subtype Enzyme Inhibition Data

| Compound | Structure | $IC_{50}$ (nM) | | | |
|---|---|---|---|---|---|
| | | PI3Kα | PI3Kβ | PI3Kγ | PI3Kδ |
| ST-177 | morpholine-triazine-(2-aminoethyl)amine with 2-(difluoromethyl)benzimidazole | 292 ± 31 | 2117 ± 444 | 771 ± 63 | 291 ± 32 |
| ST-5-02 | morpholine-triazine-(2-(methylamino)ethyl)amine with 2-(difluoromethyl)benzimidazole | 248 ± 24 | 2900 ± 375 | 681 ± 90 | 135 ± 19 |
| ST-187 | morpholine-triazine-(2-hydroxyethyl)amine with 2-(difluoromethyl)benzimidazole | 9.9 ± 1.2 | 71 ± 8 | 54 ± 1 | 8.1 ± 1.7 |

-continued

PI3K Subtype Enzyme Inhibition Data

| Compound | Structure | IC$_{50}$ (nM) | | | |
|---|---|---|---|---|---|
| | | PI3Kα | PI3Kβ | PI3Kγ | PI3Kδ |
| ST-178 | 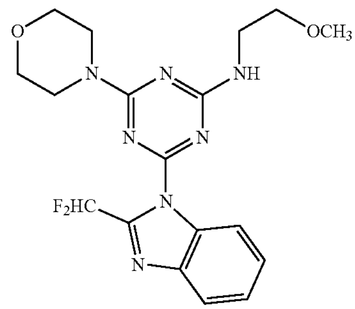 [SMILES: COCCNc1nc(N2CCOCC2)nc(-n2c(C(F)F)nc3ccccc32)n1] | 20 ± 3 | 208 ± 15 | 64 ± 5 | 17 ± 1 |
| ZSTK474 | 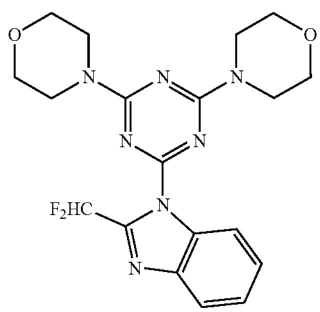 [SMILES: FC(F)c1nc2ccccc2n1-c1nc(N2CCOCC2)nc(N2CCOCC2)n1] | 5.0 ± 0.8 | 15.2 ± 1.4 | 20.8 ± 0.6 | 3.9 ± 0.6 |
| ST-5-03 | 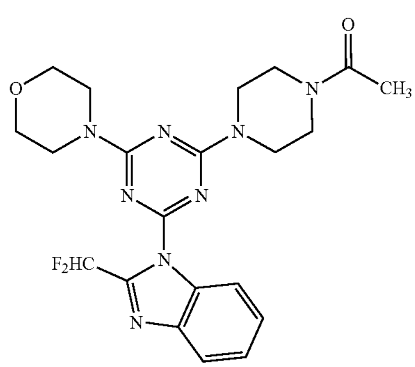 [SMILES: CC(=O)N1CCN(c2nc(N3CCOCC3)nc(-n3c(C(F)F)nc4ccccc43)n2)CC1] | 8.2 ± 0.7 | 14.3 ± 2.5 | 21 ± 1 | 2.9 ± 0.6 |
| ST-5-22 | 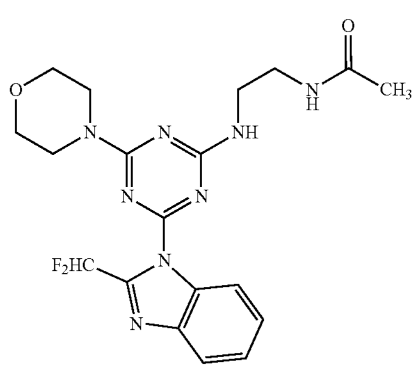 [SMILES: CC(=O)NCCNc1nc(N2CCOCC2)nc(-n2c(C(F)F)nc3ccccc32)n1] | 16.6 ± 1.4 | 199 ± 12 | 54 ± 1.5 | 9.5 ± 2.4 |

-continued
PI3K Subtype Enzyme Inhibition Data
| Compound | Structure | IC$_{50}$ (nM) | | | |
| --- | --- | --- | --- | --- | --- |
| | | PI3Kα | PI3Kβ | PI3Kγ | PI3Kδ |
| ST-5-21 | 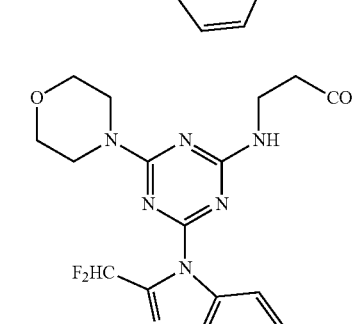 | 20 ± 0.4 | 431 ± 83 | 67 ± 2.8 | 26 ± 4.9 |
| ST-5-25 | 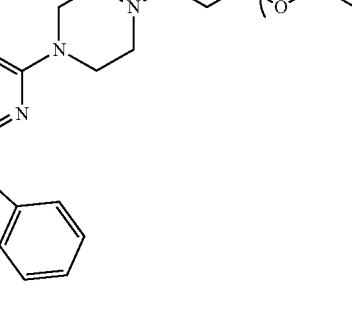 | 12.4 ± 0.7 | 787 ± 106 | 22.3 ± 0.7 | 60 ± 3.4 |
| ST-167 | 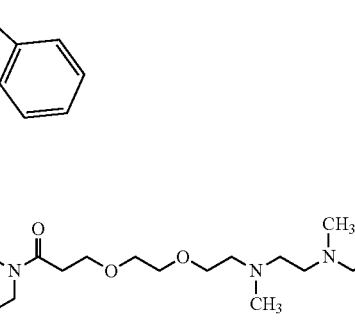 | 11.5 ± 0.1 | 214 ± 49 | 140 ± 6.6 | 1.3 ± 0.2 |
| ST-180 | 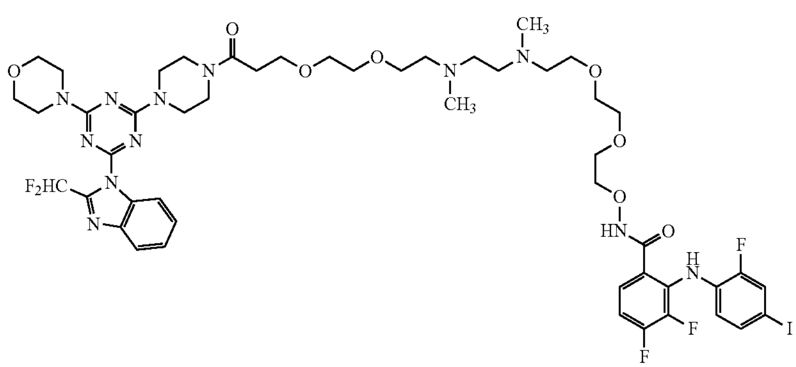 [SMILES: CN(CCOCCOCCONC(=O)c1ccc(F)c(F)c1Nc1ccc(I)cc1F)CCN(C)CCOCCOCCC(=O)N1CCN(c2nc(N3CCOCC3)nc(-n3c(C(F)F)nc4ccccc43)n2)CC1] | 39 ± 9 | 2215 ± 425 | 717 ± 136 | 52 ± 1.4 |

-continued

PI3K Subtype Enzyme Inhibition Data

| Compound | Structure | IC$_{50}$ (nM) | | | |
|---|---|---|---|---|---|
| | | PI3Kα | PI3Kβ | PI3Kγ | PI3Kδ |
| ST-5-05 | 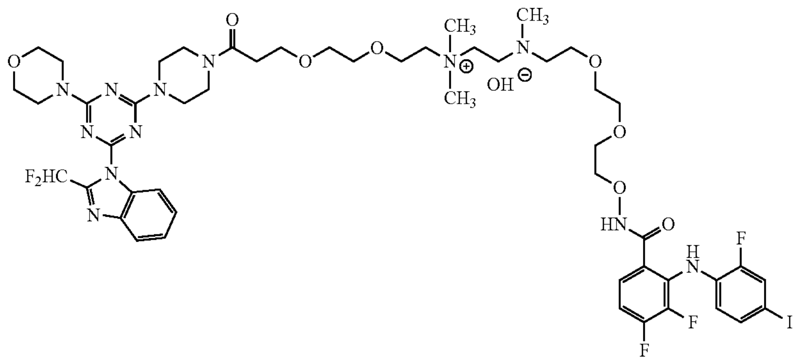 | 39 ± 2 | 2517 ± 557 | 2590 ± 660 | 56 ± 13 |
| ST-162 | 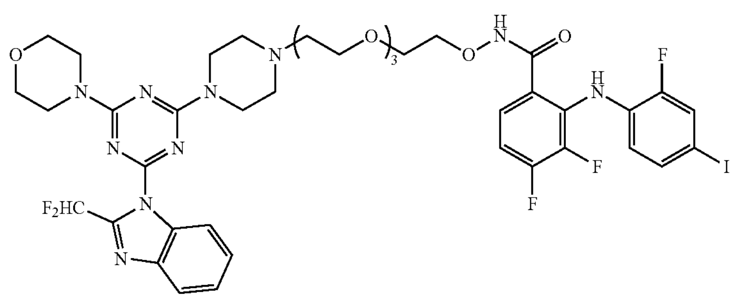 | 191 ± 64 | 4073 ± 290 | 5803 ± 511 | 942 ± 120 |
| ST-168 | | 69.2 ± 2.2 | 1482 ± 377 | 2293 ± 241 | 41.7 ± 2.1 | mTor and PI3K Subtype Inhibition Data for ST-182 and Intermediates

| Compound | Structure | IC$_{50}$ (nM) | | | | |
| --- | --- | --- | --- | --- | --- | --- |
| | | mTOR | PI3Kα | PI3Kβ | PI3Kγ | PI3Kδ |
| GSK 458 | 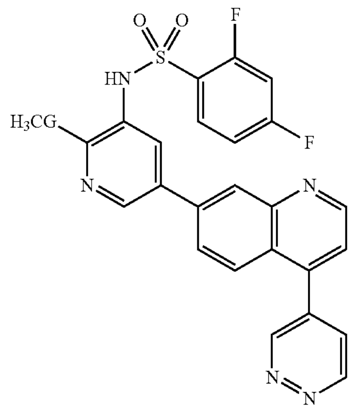 | 4.2 ± 0.1 (0.18/0.3) | < 0.495 (0.02) | 1.2 ± 0.2 (0.13) | 0.83 ± 0.1 (0.06) | < 0.495 (0.02) |
| ST-182 | 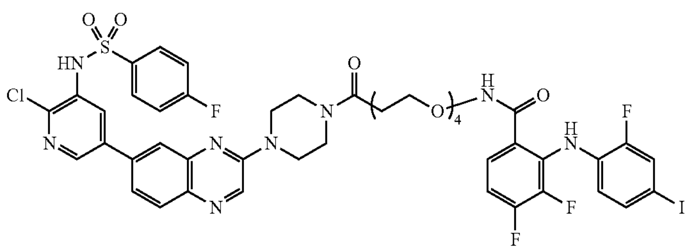 | 53.1 ± 2.5 | 2.0 ± 0.3 | 467 ± 44 | 34.1 ± 3.0 | 4.22 ± 0.64 |
| ST-5-27 | 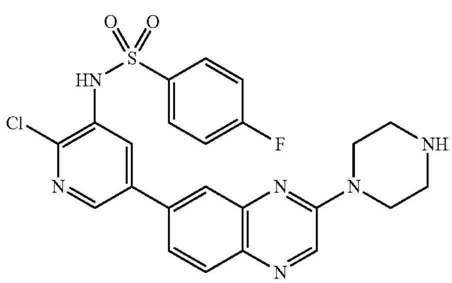 [SMILES: O=S(=O)(Nc1cc(-c2ccc3ncc(N4CCNCC4)nc3c2)cnc1Cl)c1ccc(F)cc1] | 5.97 ± 0.27 | < 0.495 | 477 ± 0.92 | 514 ± 0.23 | 0.83 ± 0.06 |
| ST-5-28 | 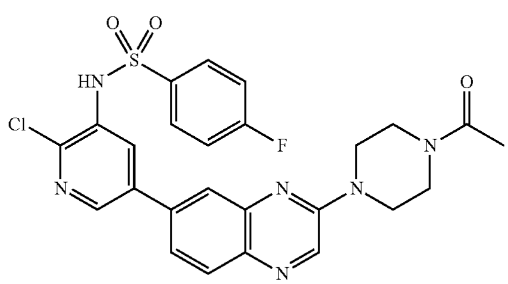 [SMILES: CC(=O)N1CCN(c2cnc3ccc(-c4cnc(Cl)c(NS(=O)(=O)c5ccc(F)cc5)c4)cc3n2)CC1] | 3.13 ± 0.14 | < 0.495 | 5.36 ± 1.10 | 0.71 ± 0.20 | < 0.495 |
| ST-5-29 | 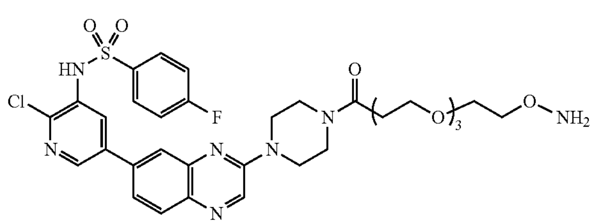 | 6.77 ± 0.43 | < 0.495 | 1.33 ± 0.59 | 30.2 ± 0.14 | < 0.495 |

In Vivo Evaluation of Inhibitor Efficacy.

Five-week-old athymic nude Foxn1nu mice were inoculated subcutaneously with 1×10⁶ fully suspended D54 cells into the flanks of two mice, and similarly, two additional mice were inoculated with A549 cells in the flank. Each injectate contained a total volume of 200 μL of cell suspension in 50% RPMI medium mixed with 50% BD Matrigel basement membrane matrix (Becton, Dickinson and Company, East Rutherford, N.J.). When tumor volumes reached approximately 150 mm³ by caliper measurement, mice were deprived of food for 2-4 hours followed by administration with either vehicle (200 μL of DMSO:HPBCD (3:2)) or inhibitor analog (14) (375 mg/kg in 200 μL of DMSO/HPBCD (3:2)) orally at 2 hours prior to sacrifice. Tumor tissues were collected from both vehicle and drug-treated groups and subjected to Western blot analysis as previously described.

REFERENCES

1. A T Baines et al., *Future Med Chem.* 2011; 3(14):1787-808.
2. A Jemal et al., *CA Cancer J Clin.* 2010; 60(5):277-300.
3. J S Sebolt-Leopold et al., *Nat Rev Cancer.* 2004; 4(12):937-47.
4. E Castellano et al., *Genes Cancer.* 2011; 2(3):261-74.
5. J S Sebolt-Leopold *Clin Cancer Res.* 2008; 14(12):3651-6.
6. C Montagut et al., *Cancer Lett.* 2009; 283(2):125-34.
7. J A McCubrey et al., *Expert Opin Emerg Drugs.* 2009; 14(4):633-48.
8. F A Karreth et al. *Mol Cell.* 2009; 36(3):477-86.
9. P I Poulikakos et al. *Nature.* 2010; 464(7287):427-30.
10. G Hatzivassiliou et al., *Nature.* 2010; 464(7287):431-5.
11. S Wee et al., *Cancer Res.* 2009; 69(10):4286-93.
12. P M Lorusso et al., *J Clin Oncol.* 2005; 23(23):5281-93.
13. J R Infante et al., *Lancet Oncol.* 2012; 13(8):773-81.
14. J A Engelman et al., *Nat Med.* 2008; 14(12):1351-6.
15. K Yu et al., *Cancer Biol Ther.* 2008; 7(2):307-15.
16. O K Mirzoeva et al., *Cancer Res.* 2009; 69(2):565-72.
17. A Carracedo et al., *J Clin Invest.* 2008; 118(9):3065-74.
18. M L Sos et al., *Proc Natl Acad Sci USA.* 2009; 106(43):18351-6.
19. T Shimizu et al., *Clin Cancer Res.* 2012; 18(8):2316-25.
20. C L Sawyers, *J Clin Oncol.* 2002; 20(17):3568-9.
21. K B Kim et al., 2013. *J Clin Oncol.* 2012; 31(4):482-9.
22. G S Falchook, et al., *Lancet Oncol.* 2012; 13(8):782-9.
23. S Bagrodia et al., *Pigment Cell Melanoma Res.* 2012; 25(6):819-31.
24. M E Van Dort et al., *Bioorg. Med. Chem.* 2015; 23:1386-1394.
25. W O 2002/006213A2.
26. EP0629617A1.
27. S Singh et al., *FASEB J.* 2014; 28(1):85-93.
28. L Rand et al., *J. Immunol.* 2009; 182:5865-5872.
29. J A Engelman et al., *Nat. Rev. Genet.* 2006; 7:606-619.
30. P Liu et al., *Nat. Rev. Drug Discov.* 2009; 8:627-644.
31. Y Liu et al., *Cell Mol Immunol.* 2015; 58.
32. J E Cho et al., *Mol. Cells* 2010; 29, 35-39.
33. R A Fratti et al., *J. Cell Biol.* 2001; 154, 631-644.
34. C KuijI et al., *Nature* 2007; 450, 725-730.
35. G Huang et al., *J. Biol. Chem.* 2012; 287, 23196-2202.
36. H Matsuoka et al., *Exp Cell Res.* 2009; 315(12):2022-32.
37. S S Liau et al., *Cancer Res.,* 2006; 66:1613-11622.
38. G W Cole Jr et al., *Anticancer Res.,* 2006; 26:809-821.
39. M R Girotti et al., *Cancer Discov* 2013; 3:158-67.
40. Y Shao et al., *Cell Death Differ* 2012; 19:2029-39.
41. E B Pasquale et al., *Nat Rev Cancer* 2010; 10:165-80.
42. K S Smalley, *Mol Cell Oncol.* 2015; 2(4):e1008291.

What is claimed:
1. A compound having a structure:

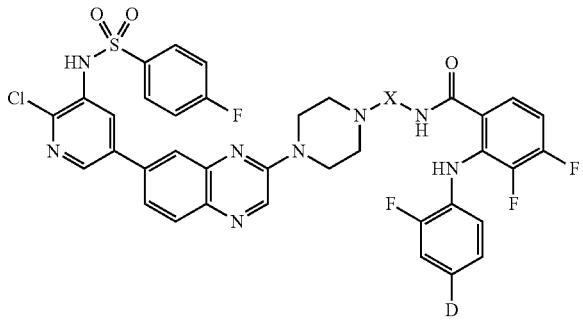

wherein D is I, —C≡CH, or —C≡C—R, R = alkyl or aryl, and X is selected from the group consisting of:

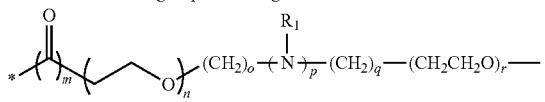

R₁, independently, is H, alkyl, or aryl, wherein, independently,
m = 0, 1; n = 0-6; o = 0-6; p = 0, 1; q = 0-6; r = 2-6,

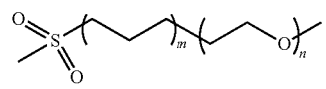

wherein, independently, m = 0-6; n = 2-6,

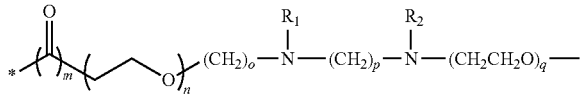

wherein, independently, m = 0, 1; n = 0-6; o = 0-6; p = 1-6; q = 2-6 and R₁, R₂, independently, are H, alkyl, aryl,

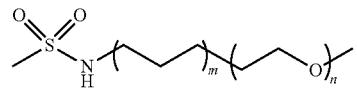

wherein, independently, m = 0-6; n = 2-6,

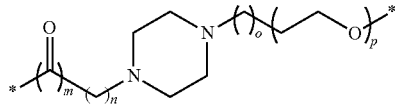

wherein, independently, m = 0, 1; n = 0-6; o = 0-6; p = 2-6,

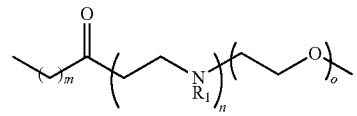

R₁, independently, is H, alkyl, or aryl,
wherein, independently,
m = 0-6; n = 1-6 o = 2-6,

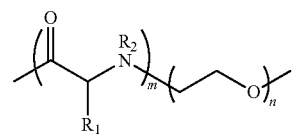

R₁, R₂, independently, are H, alkyl, or aryl
wherein, independently,
m = 1-6; n = 2-6, and -continued

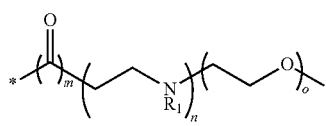

R₁, independently, is H, alkyl, or aryl,
wherein, independently,
m = 0; n = 1-6; o = 2-6.

or a pharmaceutically acceptable salt thereof.

2. A compound having a structure (a)

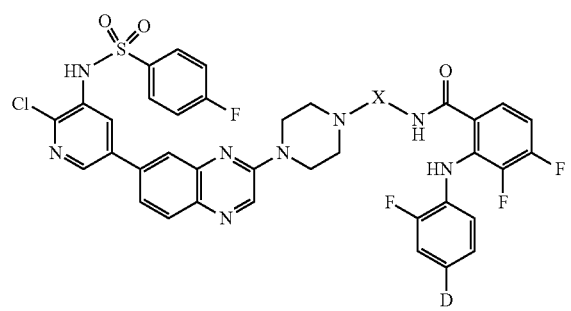

wherein D is I, —C≡CH, or —C≡C—R,
R = alkyl or aryl, and X is selected from the group consisting of:

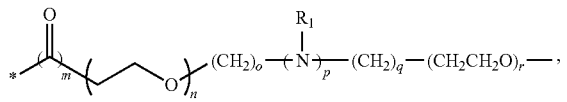

R₁, independently, is H, alkyl, or aryl, wherein, independently,
m = 0, 1; n = 0-6; o = 0-6; p = 0, 1; q = 0-6; r = 2-6

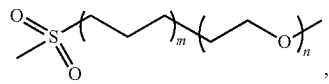

wherein, independently,
m = 0-6; n = 2-6

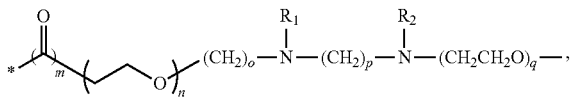

wherein, independently, m = 0, 1; n = 0-6; o = 0-6; p = 1-6;
q = 2-6 and R₁, R₂, independently, are H, arkyl, or aryl

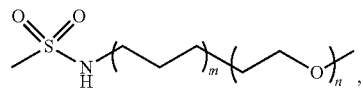

wherein independently,
m = 0-6; n = 2-6

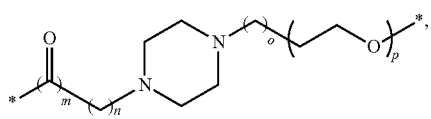

wherein, independently, m = 0, 1; n = 0-6; o = 0-6;
p = 2-6

-continued

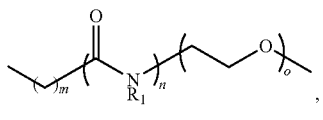

R₁, independently, is H, alkyl, or aryl, wherein,
independently, m = 0-6; n = 1-6 o = 2-6

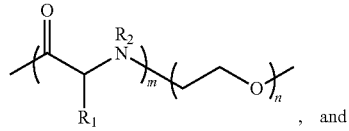
, and

R₁, R₂, independently, are H, alkyl, or aryl
wherein, independently, m = 1-6; n = 2-6

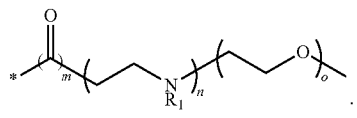

R₁, independently, is H, alkyl, or aryl,
wherein, independently, m = 0, 1; n = 1-6; o = 2-6

(b)

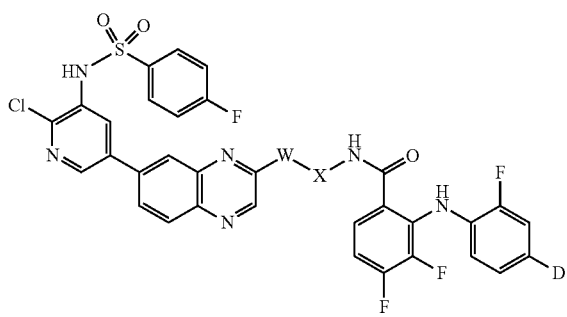

where W is ( —N ) or N-R
and R is H, alkyl or aryl and m = 0, 1-6;
D = I, —C≡CH, —C≡C—R
where R = alkyl or aryl, wherein X is selected from the group consisting of:

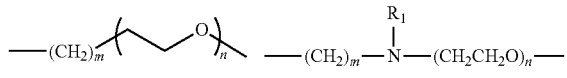

where m = 0, 1-6; n = 1-6;
or any combination of m and n

R₁ = H, alkyl or aryl where
m, n independently are 1-6

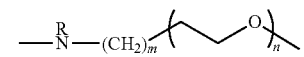

where R is H, alkyl, or aryl and m = 0, 1-6;
n = 1-6; or any combination of m and n

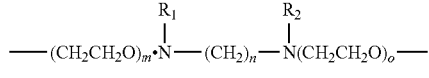

R₁, R₂ are independently H, alkyl or aryl
and m, n, o independently are 1-6 or a pharmaceutically acceptable salt thereof.

3. A compound selected from the group consisting of

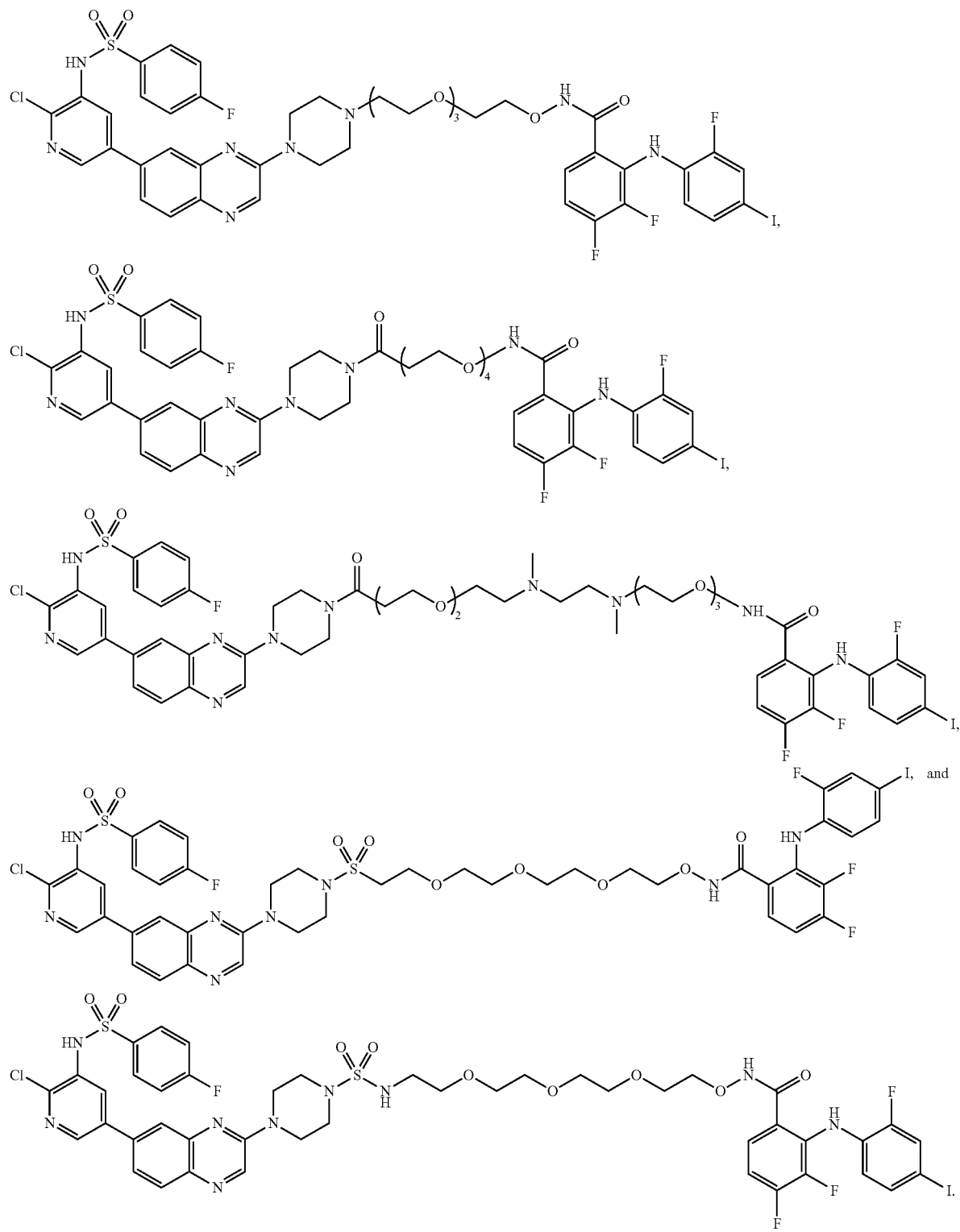

4. A pharmaceutical composition comprising a compound of claim 1 and a pharmaceutically acceptable carrier or vehicle.

5. A method of treating a disease or condition wherein inhibition of at least one of mTOR, MEK, and PI3K provides a benefit comprising administering a therapeutically effective amount of a compound of claim 1 to an individual in need thereof.

6. The method of claim 5 wherein the disease or condition is a cancer.

7. The compound of claim 3 having a structure
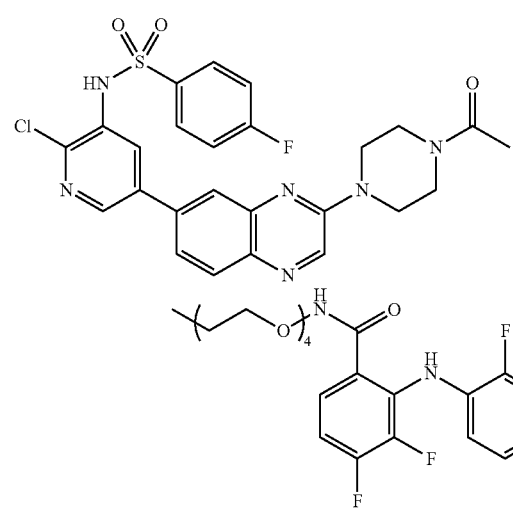
8. The compound of claim 3 having a structure
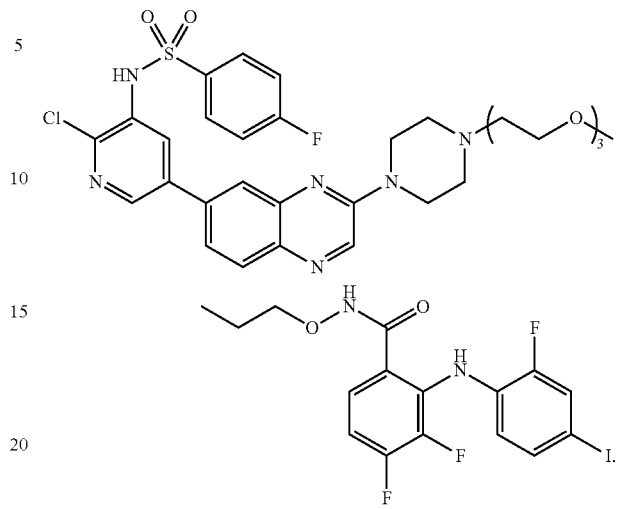
* * * * *

UNITED STATES PATENT AND TRADEMARK OFFICE
CERTIFICATE OF CORRECTION

PATENT NO. : 10,919,877 B2
APPLICATION NO. : 16/313923
DATED : February 16, 2021
INVENTOR(S) : Brian D. Ross et al.

It is certified that error appears in the above-identified patent and that said Letters Patent is hereby corrected as shown below:

In the Claims

At Column 110, Line 29, "q=0-6;" should be -- q=0-6, --.

At Column 111, Line 9, "m=0;" should be -- m=0,1; --.

At Column 111, Line 35, " [chemical structure] " should be -- [chemical structure] --.

At Column 111, Line 37, "q=0-6; r=2-6" should be -- q=0-6, r=2-6, --.

At Column 111, Line 40, " [chemical structure] ," should be -- [chemical structure] --.

At Column 111, Line 44, "n=2-6" should be -- n=2-6, --.

At Column 111, Line 45, " [chemical structure] " should be

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,919,877 B2

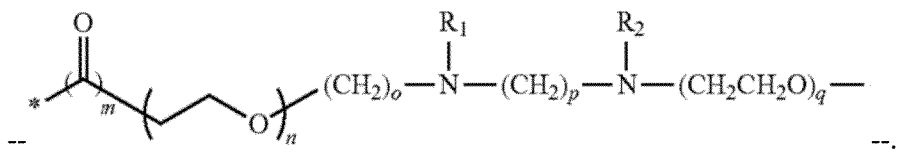

At Column 111, Line 50, "arkyl, or aryl" should be -- alkyl, or aryl, --.

At Column 111, Lines 51-54, " 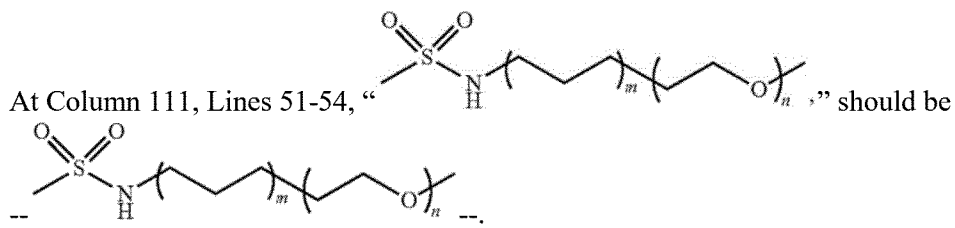 ," should be

-- [structure] --.

At Column 111, Lines 59-64, " 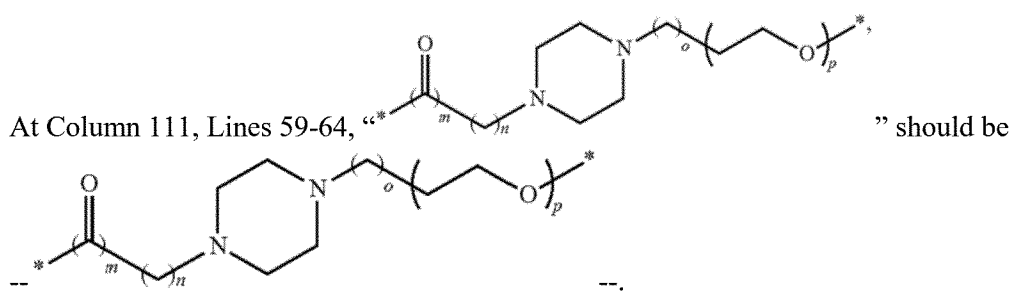 " should be

-- [structure] --.

At Column 111, Line 66, "p=2-6" should be -- p=2-6, --.

At Column 112, Lines 1-5, " 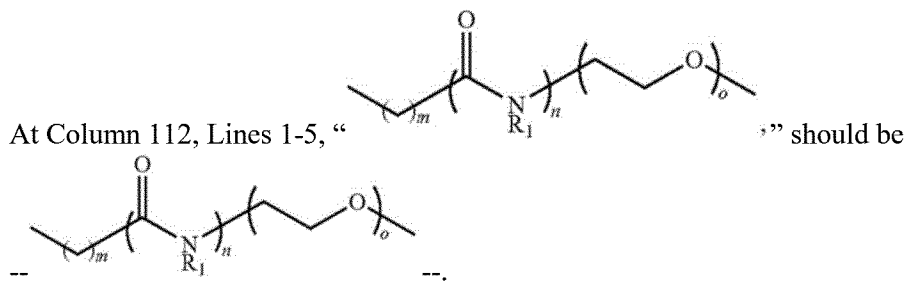 ," should be

-- [structure] --.

At Column 112, Line 7, "o=2-6" should be -- o=2-6, --.

At Column 112, Lines 9-13, " 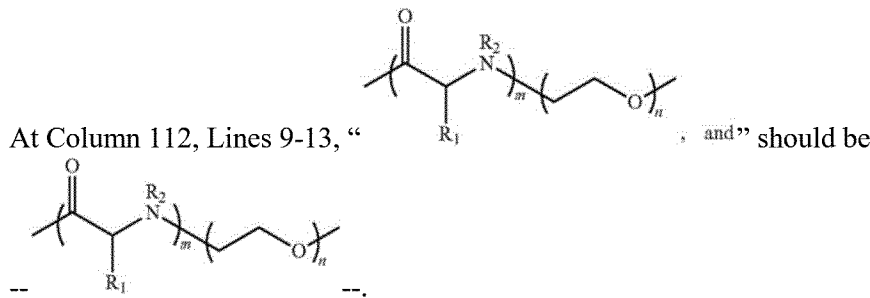 , and" should be

-- [structure] --.

At Column 112, Line 15, "n=2-6" should be -- n=2-6, --.

CERTIFICATE OF CORRECTION (continued)
U.S. Pat. No. 10,919,877 B2

At Column 112, Lines 16-21, " 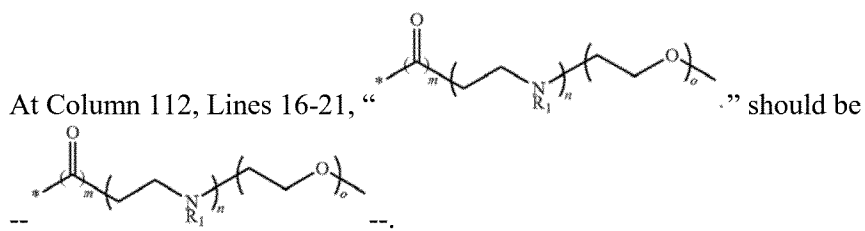 ." should be -- 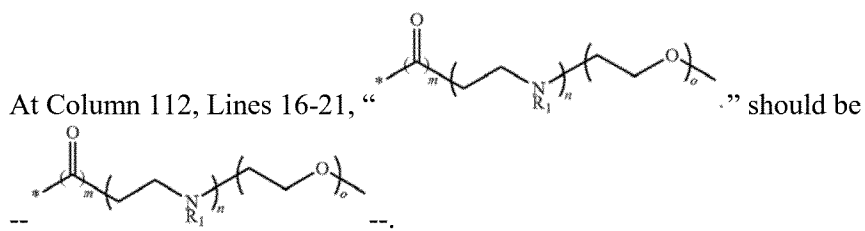 --.

At Column 112, Line 22, "o=2-6" should be -- o=2-6, --.